United States Patent
Clements et al.

(10) Patent No.: US 8,278,304 B2
(45) Date of Patent: Oct. 2, 2012

(54) SUBSTITUTED 4-HYDROXYPYRIMIDINE-5-CARBOXAMIDES

(75) Inventors: Matthew J. Clements, Old Bridge, NJ (US); John S. Debenham, Scotch Plains, NJ (US); Jeffrey J. Hale, Westfield, NJ (US); Christina B. Madsen-Duggan, Scotch Plains, NJ (US); Thomas F. Walsh, Watchung, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 665 days.

(21) Appl. No.: 12/381,468

(22) Filed: Mar. 12, 2009

(65) Prior Publication Data

US 2009/0239876 A1 Sep. 24, 2009

Related U.S. Application Data

(60) Provisional application No. 61/192,918, filed on Sep. 23, 2008, provisional application No. 61/069,864, filed on Mar. 18, 2008.

(51) Int. Cl.
*A61K 31/501* (2006.01)
*A61K 31/4965* (2006.01)
*C07D 401/06* (2006.01)
*C07D 239/02* (2006.01)

(52) U.S. Cl. ............. 514/252.02; 514/255.05; 544/238; 544/319

(58) Field of Classification Search ............. 514/252.02, 514/255.05; 544/238, 319
See application file for complete search history.

(56) References Cited

U.S. PATENT DOCUMENTS

| | | | |
|---|---|---|---|
| 7,056,942 B2 * | 6/2006 | Hildesheim et al. | 514/411 |
| 2004/0142930 A1 | 7/2004 | Yamada et al. | |

FOREIGN PATENT DOCUMENTS

| | | |
|---|---|---|
| EP | 0 012 361 A1 | 6/1980 |
| EP | 0 557 879 A1 | 9/1993 |
| EP | 1 219 609 A1 | 7/2002 |
| EP | 1 223 170 A1 | 7/2002 |
| EP | 1 366 760 A | 12/2003 |
| WO | WO 02 066036 A1 | 8/2002 |
| WO | WO 2005 042519 A1 | 5/2005 |
| WO | WO 2006 033844 A2 | 3/2006 |
| WO | WO 2007 031829 A2 | 3/2007 |
| WO | WO 2007 070606 A2 | 6/2007 |
| WO | WO 2007 150011 A2 | 12/2007 |
| WO | 2008/028937 * | 3/2008 |

OTHER PUBLICATIONS

Yurugi, S., et al., "Studies on the Syntheses of N-Heterocyclic Compounds. I. On the Syntheses of 2,4,5-Trisubstitutedpyrimidine Derivatives" Ann. Rept. Takeda Res. Lab. 28 (1969) 1-11.
Weimin, C., et al., "Synthesis and Antitumor Activities of Novel 2-Substituted Pyrimidinone-5-carboxylic Acid Benzylamides" Chemical Bulletin 69:8 (2006) 623-626.
Semenza, G.L., "Hypoxia-inducible factor 1:oxygen homeostasis and disease pathophysiology" Elsevier Science Ltd., Trends in Molecular Medicine 7:8 (2001) 345-350.

* cited by examiner

*Primary Examiner* — James O Wilson
*Assistant Examiner* — Ebenezer O Sackey
(74) *Attorney, Agent, or Firm* — Patricia A. Shatynski; Valerie J. Camara

(57) ABSTRACT

The present invention relates to substituted 4-hydroxypyrimidine-5-carboxamides useful as HIF prolyl hydroxylase inhibitors to treat anemia and like conditions.

17 Claims, No Drawings

SUBSTITUTED 4-HYDROXYPYRIMIDINE-5-CARBOXAMIDES

CROSS REFERENCE TO RELATED APPLICATIONS

This application claims the benefit of U.S. Provisional Application Ser. No. 61/192,918 filed Sep. 23, 2008 and U.S. Provisional Application Ser. No. 61/069,864 filed Mar. 18, 2008.

BACKGROUND OF THE INVENTION

The insufficient delivery of oxygen to cells and tissues is associated with anemia, which is defined as a deficiency in the blood's oxygen-carrying capacity, and ischemia, in which restrictions in blood supply are caused by a constriction or blockage of blood vessels. Anemia can be caused by the loss of red blood cells (hemorrhage), excessive red blood cell destruction (hemolysis) or deficiencies in erythropoiesis (production of red blood cells from precursors found in the bone marrow). The symptoms of anemia can include weakness, dizziness, fatigue, pallor, impairment of cognitive function and a general reduction in quality of life. Chronic and/or severe anemia can lead to the exacerbation of myocardial, cerebral or peripheral ischemia and to heart failure. Ischemia is defined as an absolute or relative shortage of oxygen to a tissue or organ and can result from disorders such as atherosclerosis, diabetes, thromboembolisms, hypotension, etc. The heart, brain and kidney are especially sensitive to ischemic stress caused by low blood supply.

The primary pharmacological treatment for anemia is administration of some variant of recombinant human erythropoietin (EPO). For anemias associated with kidney disease, chemotherapy-induced anemia, anemia from HIV-therapy or anemia due to blood loss, recombinant EPO is administered to enhance the supply of the hormone, correct the shortage of red blood cells and increase the blood's oxygen-carrying capacity. EPO replacement is not always sufficient to stimulate optimal erythropoiesis (e.g., in patients with iron processing deficiencies) and has associated risks.

Hypoxia-inducible factor (HIF) has been identified as a primary regulator of the cellular response to low oxygen. HIF is a heterodimeric gene transcription factor consisting of a highly regulated α-subunit (HIF-α) and a constitutively expressed β-subunit (HIF-β, also known as ARNT, or aryl hydrocarbon receptor nuclear transporter). HIF target genes are reported to be associated with various aspects of erythropoiesis (e.g., erythropoietin (EPO) and EPO receptor), glycolysis and angiogenesis (e.g., vascular endothelial growth factor (VEGF)). Genes for proteins involved in iron absorption, transport and utilization as well as heme synthesis are also targets of HIF.

Under normal oxygenation, HIF-α is a substrate in a reaction with molecular oxygen, which is catalyzed by a family of iron(II)-, 2-ketoglutarate- and ascorbate-dependent dioxygenase enzymes called PHD-1 (EGLN2, or egg laying abnormal 9 homolog 2, PHD2 (EGLN1), and PHD3 (EGLN3). Proline residues of HIF-α are hydroxylated (e.g., Pro-402 and Pro-564 of HIF-1α) and the resulting product is a target of the tumor suppressor protein von-Hippel Lindau, a component of an E3 ubiquitin ligase multiprotein complex involved in protein ubiquitination. Under low oxygenation, the HIF-α hydroxylation reaction is less efficient and HIF-α is available to dimerize with HIF-β. HIF dimers are translocated to the cell nucleus where they bind to a hypoxia-responsive enhancer element of HIF target genes.

Cellular levels of HIF are known to increase under conditions of hypoxia and after exposure to hypoxia mimetic agents. The latter includes, but is not limited to, specific metal ions (e.g., cobalt, nickel, manganese), iron chelators (e.g., desferrioxamine) and analogs of 2-ketoglurate (e.g., N-oxalyl glycine). The compounds of the present invention inhibit the HIF prolyl hydroxylases (PHD-1, PHD-2, PHD-3) and can also serve to modulate HIF levels. These compounds therefore have utility for the treatment and/or prevention of disorders or conditions where HIF modulation is desirable, such as anemia and ischemia. As an alternative to recombinant erythropoietin therapy, the compounds of the present invention provide a simpler and broader method for the management of anemia.

SUMMARY OF THE INVENTION

The present invention concerns compounds of formula I

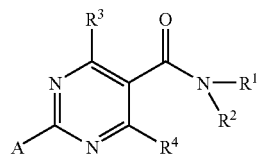

which inhibit HIF prolyl hydroxylase, their use for enhancing endogenous production of erythropoietin, and for treating conditions associated with reduced endogenous production of erythropoietin such as anemia and like conditions, as well as pharmaceutical compositions comprising such a compound and a pharmaceutical carrier.

DETAILED DESCRIPTION OF THE INVENTION

The present invention provides compounds of formula I and pharmaceutically acceptable salts and solvates thereof:

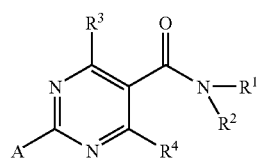

A is a heterocyclyl, optionally substituted by one or more $R^9$ substituents;

$R^1$ is selected from —$C_{1-10}$ alkyl, —$C_{0-10}$ alkyl-$C_{3-10}$ cycloalkyl, —$C_{2-10}$ alkenyl, —$C_{0-10}$ alkyl-$C_{5-10}$ cycloalkenyl, —$C_{2-10}$ alkynyl, —$C_{0-10}$ alkylaryl, —$C_{0-10}$ alkylheterocyclyl; —$NR^bR^c$, and —$C_{0-10}$ alkyl $C_{3-10}$ heterocycloalkyl, wherein in $R^1$ said alkyl, alkenyl, alkynyl, cycloalkenyl, aryl, heterocycloalkyl, heterocyclyl, and cycloalkyl are each optionally substituted with one or more $R^8$ substituents and optionally two $R^8$ may join together to form a 3 to 8 member ring;

$R^2$ is selected from hydrogen, —$C_{1-10}$ alkyl, aryl, —$C_3$-$C_{10}$ cycloalkyl, and heterocyclyl, wherein $C_{1-10}$ alkyl, —$C_3$-$C_{10}$ cycloalkyl, aryl, and heterocyclyl are unsubstituted or substituted with one or more substituents selected from halo, hydroxyl, $C_{1-10}$ alkyl, and —$OC_{1-10}$ alkyl;

$R^3$ is selected from hydrogen, halogen, hydroxy, —$C_{1-6}$ alkyl, —$C_{1-6}$ alkoxy, heterocyclyl, —$NR^bR^c$, and —$SC_{0-6}$ alkyl, wherein said alkyl, and alkoxy, are optionally substituted by one or more substituents $R^{10}$;

$R^4$ is selected from hydrogen, $-C_1$-$C_{10}$ alkyl, $-C_{2-10}$ alkenyl, $-C_{2-10}$ alkynyl, $-C_{3-10}$ cycloalkyl, $C_{3-10}$ heterocycloalkyl, $-(C_{0-10}$ alkyl)aryl, $(C_{0-10}$ alkyl)heterocyclyl, $-C_{5-10}$ cycloalkenyl, and $-NR^bR^c$, wherein said alkyl, alkenyl, alkynyl, cycloalkyl, cycloalkenyl, aryl, and heterocyclyl are optionally substituted by one or more substituents $R^9$;

or $R^1$ and $R^2$, are linked together to form a ring of 5 to 8 atoms optionally substituted with one or more substituents $R^9$;

$R^8$ is selected from halogen, hydroxyl, $-C_{1-10}$ alkyl, $-C_{1-10}$ alkenyl, $-C_{1-10}$ alkynyl, $-OC_{1-10}$ alkylaryl, aryl, heterocyclyl, $-C_{3-10}$ cycloalkyl, $-C_{3-10}$ heterocycloalkyl, cyano, oxo, $-OC_{1-10}$ alkyl, $C_{2-6}$ alkylaminocarbonylamino, $C_{0-10}$ alkyloxycarbonylamino$C_{0-6}$ alkyl, $C_{0-10}$ alkylcarbonylamino$C_{0-6}$ alkyl, $C_{2-6}$ alkylaminosulfonylamino$C_{0-4}$ alkyl, $-C_{2-6}$ alkylsulfonylamino$C_{0-4}$ alkyl, $-C_{1-4}$ alkylsulfonyl, arylsulfonyl, $-C_{1-10}$ alkylaminosulfonyl, $C_{1-10}$ alkylaminocarbonyl, $-(C=O)N(C_{0-6}$ alkyl$)_2$, difluoromethoxy, trifluoromethoxy, trifluoroethoxy, $-SR^a$, and $NR^bR^c$, wherein said alkyl, alkenyl, alkynyl, aryl, heterocyclyl, cycloalkyl, heterocycloalkyl may optionally be substituted with one or more groups selected from hydroxyl, $-CO_2H$, halogen, $-OC_{1-10}$ alkyl, and $C_{1-6}$ alkyl;

$R^9$ is selected from halogen, hydroxy, oxo, aryl, heterocyclyl, $-C_{1-6}$ alkyl, $-C_{3-10}$ cycloalkyl, $-C_{3-10}$ heterocycloalkyl, $-(C_{1-10}$ alkyl)aryl, $-(C_{0-10}$ alkyl)heterocyclyl, $-C_{5-10}$ cycloalkenyl, $-C_{2-10}$ alkynyl, $-C_{1-6}$ alkoxy, aryloxy, heterocyclyloxy, $-CO_2R^a$, $-NR^bR^c$, $-CONR^bR^c$, $-OCO_2R^a$, $-OCONR^bR^c$, $-NR^dCO_2R^a$, $-NR^d$-$CONR^bR^c$, $-SR^a$ and $-S(O)_nR^d$, wherein said aryl, heterocyclyl, alkoxy, aryloxy, heterocyclyloxy are optionally substituted by one or more substituents $R^{10}$;

$R^{10}$ is selected from aryl, heterocyclyl, halogen, $-C_{1-6}$ alkyl, $-C_{1-6}$ alkoxy, $CO_2R^a$, cyano, $O(C=O)$ $C_{1-6}$ alkyl, $NO_2$, difluoromethoxy, trifluoromethoxy, trifluoroethoxy, $-O_{(0-1)}(C_{1-10})$perfluoroalkyl, $C_{0-10}$ alkylaminocarbonylamino, $C_{0-10}$ alkyloxycarbonylamino$C_{0-10}$ alkyl, $C_{0-10}$ alkylcarbonylamino$C_{0-10}$ alkyl, $C_{0-10}$ alkylaminocarbonyl, $C_{0-10}$ alkylaminosulfonylamino$C_{0-10}$ alkyl, $C_{0-10}$ alkylsulfonylamino$C_{0-10}$ alkyl, $C_{0-10}$ alkylsulfonyl, $C_{0-10}$ alkylaminosulfonyl, $-(C=O)N(C_{0-6}$ alkyl$)_2$, $-S(C_{0-6}$ alkyl), and $NH_2$;

n is 1 or 2;

$R^a$ is chosen from hydrogen; $-C_{1-10}$ alkyl, $-(C_{1-6}$ alkyl)$C_{3-8}$ cycloalkyl; and $-(C_{1-6}$ alkyl)phenyl; and $R^b$, $R^c$, and $R^d$ are each independently chosen from hydrogen, $-C_{1-10}$ alkyl, $-C_{3-10}$ cycloalkyl, $-C_{3-10}$ heterocycloalkyl, aryl, and heterocyclyl, wherein said alkyl, cycloalkyl, aryl and heterocyclyl are optionally substituted by one or more substituents $R^{10}$.

Illustrative but nonlimiting examples of compounds of the invention are the following:

2-(4-Bromopyridin-2-yl)4-hydroxy-N-(1-methyl-1-phenylethyl)pyrimidine-5-carboxamide;

2-(4-Hydroxy-5-{[(1-methyl-1-phenylethyl)amino]carbonyl}pyrimidin-2-yl)isonicotinic acid;

6-(5-{[(4-Fluorobenzyl)amino]carbonyl}4-hydroxypyrimidin-2-yl)nicotinic acid;

4-Hydroxy-N-(1-methyl-1-phenylethyl)-2-pyridazin-3-ylpyrimidine-5-carboxamide;

N-[bis(4-methoxyphenyl)methyl]4-hydroxy-2-pyridazin-3-ylpyrimidine-5-carboxamide;

N-[bis(4-methoxyphenyl)methyl]4-hydroxy-2-pyridazin-3-ylpyrimidine-5-carboxamide 1,3-dihydroxy-2-(hydroxymethyl)propan-2-ammonium salt;

N-[bis(4-methoxyphenyl)methyl]-4-hydroxy-2-pyridazin-3-ylpyrimidine-5-carboxamide potassium salt;

N-[bis(4-hydroxyphenyl)methyl]-4-hydroxy-2-pyridazin-3-ylpyrimidine-5-carboxamide;

N-(4-fluorobenzyl)-4-hydroxy-2-pyridin-2-ylpyrimidine-5-carboxamide;

4-Hydroxy-N-(1-methyl-1-phenylethyl)-2-(1H-pyrazol-1-yl)pyrimidine-5-carboxamide;

N-(4-bromobenzyl)-4-hydroxy-2-(1H-pyrazol-1-yl)pyrimidine-5-carboxamide;

4-Hydroxy-2-(1H-pyrazol-1-yl)-N-{[6-(trifluoromethyl)pyridin-3-yl]methyl}pyrimidine-5-carboxamide;

N-(4-fluorobenzyl)-4-hydroxy-2-[5-(trifluoromethyl)pyridin-2-yl]pyrimidine-5-carboxamide;

N-[1-(4-fluorophenyl)ethyl]-4-hydroxy-2-pyridin-2-ylpyrimidine-5-carboxamide;

4-Hydroxy-N-(1-methyl-1-phenylethyl)-2-pyridin-2-ylpyrimidine-5-carboxamide;

N-[bis(4-methoxyphenyl)methyl]-4-hydroxy-2-pyridin-2-ylpyrimidine-5-carboxamide;

N-(biphenyl-4-ylmethyl)-4-hydroxy-2-(6-methylpyridin-2-yl)pyrimidine-5-carboxamide;

N-(2-chloro-4-fluorophenyl)-4-hydroxy-2-(6-methylpyridin-2-yl)pyrimidine-5-carboxamide;

N-(2,4-dichlorobenzyl)-4-hydroxy-2-(6-methylpyridin-2-yl)pyrimidine-5-carboxamide;

N-(4-fluorobenzyl)-4-hydroxy-2-pyrazin-2-ylpyrimidine-5-carboxamide;

4-Hydroxy-N-(1-methyl-1-phenylethyl)-2-pyrazin-2-ylpyrimidine-5-carboxamide;

4-Hydroxy-2-pyrazin-2-yl-N-[4-(trifluoromethyl)benzyl]pyrimidine-5-carboxamide;

N-(4-fluorobenzyl)-4-hydroxy-2,2'-bipyrimidine-5-carboxamide;

4-Hydroxy-N-(1-methyl-1-phenylethyl)-2,2'-bipyrimidine-5-carboxamide;

4-Hydroxy-N-[4-(trifluoromethyl)benzyl]-2,2'-bipyrimidine-5-carboxamide;

N-(2-chlorobenzyl)-4-hydroxy-2-pyridazin-3-ylpyrimidine-5-carboxamide;

N-[(1S)-1-(4-bromophenyl)ethyl]-4-hydroxy-2-pyridazin-3-ylpyrimidine-5-carboxamide;

N-(diphenylmethyl)-4-hydroxy-2-pyridazin-3-ylpyrimidine-5-carboxamide;

4-hydroxy-N-(1-phenylcyclohexyl)-2-pyridazin-3-ylpyrimidine-5-carboxamide;

N-(biphenyl-4-ylmethyl)-4-hydroxy-2-pyridazin-3-ylpyrimidine-5-carboxamide;

4-Hydroxy-2-(2-methyl-1,3-thiazol-4-yl)-N-[4-(trifluoromethyl)benzyl]pyrimidine-5-carboxamide;

N-(biphenyl-4-ylmethyl)-4-hydroxy-2-(2-methyl-1,3-thiazol-4-yl)pyrimidine-5-carboxamide;

4-Hydroxy-2-(2-methyl-1,3-thiazol-4-yl)-N-[4-(trifluoromethoxy)benzyl]pyrimidine-5-carboxamide;

N-[2-(4-fluorophenyl)ethyl]-4-hydroxy-2-(2-methyl-1,3-thiazol-4-yl)pyrimidine-5-carboxamide;

4-Hydroxy-N-(1-methyl-1-phenylethyl)-2-(2-methyl-1,3-thiazol-4-yl)pyrimidine-5-carboxamide;

4-Hydroxy-2-(2-methyl-1,3-thiazol-4-yl)-N-[4-(trifluoromethyl)phenyl]pyrimidine-5-carboxamide;

4-Hydroxy-2-(2-methyl-1,3-thiazol-4-yl)-N-[(1S)-1-phenylpropyl]pyrimidine-5-carboxamide;

4-Hydroxy-2-(2-methyl-1,3-thiazol-4-yl)-N-[(1R)-1-phenylpropyl]pyrimidine-5-carboxamide;

N-(2,4-dichlorobenzyl)-4-hydroxy-2-(2-methyl-1,3-thiazol-4-yl)pyrimidine-5-carboxamide;
N-(2-chloro-4-fluorophenyl)-4-hydroxy-2-(2-methyl-1,3-thiazol-4-yl)-pyrimidine-5-carboxamide;
N-(diphenylmethyl)-4-hydroxy-2-(2-methyl-1,3-thiazol-4-yl)pyrimidine-5-carboxamide;
N-(tert-butyl)-4-hydroxy-2-(2-methyl-1,3-thiazol-4-yl)pyrimidine-5-carboxamide;
4-Hydroxy-2-(4-methyl-1,3-thiazol-2-yl)-N-[(1S)-1-phenylpropyl]pyrimidine-5-carboxamide;
N-(biphenyl-3-ylmethyl)-4-hydroxy-2-(2-methyl-1,3-thiazol-4-yl)-pyrimidine-5-carboxamide;
4-Hydroxy-N-(1-methyl-1-phenylethyl)-2-(1,3-thiazol-4-yl)pyrimidine-5-carboxamide;
2-(3,5-Dimethyl-1H-pyrazol-1-yl)-4-hydroxy-N-[4-(trifluoromethoxy)benzyl]pyrimidine-5-carboxamide;
N-(diphenylmethyl)-4-hydroxy-2-(1H-pyrrol-2-yl)pyrimidine-5-carboxamide;
N-(diphenylmethyl)-4-hydroxy-2-(1H-1,2,4-triazol-1-yl)pyrimidine-5-carboxamide;
4-Hydroxy-N-(1-methyl-1-phenylethyl)-2-(1-methyl-1H-pyrazol-3-yl)pyrimidine-5-carboxamide;
4-Hydroxy-N-[(1S)-1-phenylpropyl]-2-(1H-pyrazol-1-yl)pyrimidine-5-carboxamide;
N-(biphenyl-4-ylmethyl)-4-hydroxy-2-(1H-pyrazol-1-yl)pyrimidine-5-carboxamide;
4-Hydroxy-2-(1H-pyrazol-1-yl)-N-[4-(trifluoromethoxy)benzyl]pyrimidine-5-carboxamide;
N-(2,4-dichlorobenzyl)-4-hydroxy-2-(1H-pyrazol-1-yl)pyrimidine-5-carboxamide;
N-(diphenylmethyl)-4-hydroxy-2-(1H-pyrazol-1-yl)pyrimidine-5-carboxamide;
N-(biphenyl-3-ylmethyl)-4-hydroxy-2-(1H-pyrazol-1-yl)pyrimidine-5-carboxamide;
4-Hydroxy-2-(1H-pyrazol-1-yl)-N-[4-(trifluoromethyl)benzyl]pyrimidine-5-carboxamide;
N-(1,3-benzothiazol-2-ylmethyl)-4-hydroxy-2-(1H-pyrazol-1-yl)pyrimidine-5-carboxamide;
4-Hydroxy-N-(1-naphthylmethyl)-2-(1H-pyrazol-1-yl)pyrimidine-5-carboxamide;
N-(2,3-dihydro-1H-inden-1-yl)-4-hydroxy-2-(1H-pyrazol-1-yl)pyrimidine-5-carboxamide;
4-Hydroxy-N-[phenyl(pyridin-4-yl)methyl]-2-(1H-pyrazol-1-yl)pyrimidine-5-carboxamide;
N-[(6-chloropyridin-3-yl)methyl]-4-hydroxy-2-(1H-pyrazol-1-yl)pyrimidine-5-carboxamide;
4-Hydroxy-N-[(1S)-1-phenylethyl]-2-(1H-pyrazol-1-yl)pyrimidine-5-carboxamide;
4-hydroxy-N-[(1R)-1-phenylethyl]-2-(1H-pyrazol-1-yl)pyrimidine-5-carboxamide;
N-[(2'-chlorobiphenyl-4-yl)methyl]-4-hydroxy-2-(1H-pyrazol-1-yl)pyrimidine-5-carboxamide;
N-[(4'-fluorobiphenyl-4-yl)methyl]-4-hydroxy-2-(1H-pyrazol-1-yl)pyrimidine-5-carboxamide;
N-[(5-chloropyrazin-2-yl)methyl]-4-hydroxy-2-(1H-pyrazol-1-yl)pyrimidine-5-carboxamide;
N-[3,5-bis(trifluoromethyl)benzyl]-4-hydroxy-2-(1H-pyrazol-1-yl)pyrimidine-5-carboxamide;
4-Hydroxy-N-[(5-methylpyrazin-2-yl)methyl]-2-(1H-pyrazol-1-yl)pyrimidine-5-carboxamide;
N-(1,2-diphenylethyl)-4-hydroxy-2-(1H-pyrazol-1-yl)pyrimidine-5-carboxamide;
N-[2-fluoro-4-(trifluoromethyl)benzyl]-4-hydroxy-2-(1H-pyrazol-1-yl)pyrimidine-5-carboxamide;
N-(cyclopropylmethyl)-4-hydroxy-2-(1H-pyrazol-1-yl)pyrimidine-5-carboxamide;
N-[1-(4-fluorophenyl)ethyl]-4-hydroxy-2-(1H-pyrazol-1-yl)pyrimidine-5-carboxamide;
N-[(1S)-1-(4-fluorophenyl)ethyl]-4-hydroxy-2-(1H-pyrazol-1-yl)pyrimidine-5-carboxamide;
N-[(1R)-1-(4-fluorophenyl)ethyl]-4-hydroxy-2-(1H-pyrazol-1-yl)pyrimidine-5-carboxamide;
N-[1-(4-fluorophenyl)-1-methylethyl]-4-hydroxy-2-(1H-pyrazol-1-yl)pyrimidine-5-carboxamide;
4-Hydroxy-N-{1-methyl-1-[6-(trifluoromethyl)pyridin-3-yl]ethyl}-2-(1H-pyrazol-1-yl)pyrimidine-carboxamide;
N-(4-chlorobenzyl)-4-hydroxy-2-(1H-pyrazol-1-yl)pyrimidine-5-carboxamide;
N'-Ethyl-4-hydroxy-N'-phenyl-2-(1H-pyrazol-1-yl)pyrimidine-5-carbohydrazide trifluoroacetate;
4-Hydroxy-N-(4-methylbenzyl)-2-(1H-pyrazol-1-yl)pyrimidine-5-carboxamide;
4-Hydroxy-N-[(1R)-1-(4-methylphenyl)ethyl]-2-(1H-pyrazol-1-yl)pyrimidine-5-carboxamide;
4-Hydroxy-N-[(1S)-1-(4-methylphenyl)ethyl]-2-(1H-pyrazol-1-yl)pyrimidine-5-carboxamide;
4-hydroxy-N-piperidin-1-yl-2-(1H-pyrazol-1-yl)pyrimidine-5-carboxamide trifluoroacetate;
5-(Piperidin-1-ylcarbonyl)-2-(1H-pyrazol-1-yl)pyrimidin-4-ol;
N-(4-tert-butylcyclohexyl)-4-hydroxy-2-(1H-pyrazol-1-yl)pyrimidine-5-carboxamide;
4-Hydroxy-N-[(4R)-3-oxoisoxazolidin-4-yl]-2-(1H-pyrazol-1-yl)pyrimidine-5-carboxamide;
N-[(1R)-1-cyclohexylethyl]-4-hydroxy-2-(1H-pyrazol-1-yl)pyrimidine-5-carboxamide;
N-[(1S)-1-cyclohexylethyl]-4-hydroxy-2-(1H-pyrazol-1-yl)pyrimidine-5-carboxamide;
4-hydroxy-2-(1H-pyrazol-1-yl)-N-(1-pyridin4-ylethyl)pyrimidine-5-carboxamide trifluoroacetate;
4-Hydroxy-N-(1-phenylcyclopropyl)-2-(1H-pyrazol-1-yl)pyrimidine-5-carboxamide;
4-hydroxy-N',N'-diphenyl-2-(1H-pyrazol-1-yl)pyrimidine-5-carbohydrazide trifluoroacetate;
N-[1-(3,4-difluorophenyl)-1-methylethyl]-4-hydroxy-2-(1H-pyrazol-1-yl)pyrimidine-5-carboxamide;
N-{(1R)-1-[(3S,5S,7S)-1-adamantyl]ethyl}4-hydroxy-2-(1H-pyrazol-1-yl)pyrimidine-5-carboxamide;
N-[(1S)-1-(4-bromophenyl)ethyl]-4-hydroxy-2-(1H-pyrazol-1-yl)pyrimidine-5-carboxamide;
N-{[4-hydroxy-2-(1H-pyrazol-1-yl)pyrimidin-5-yl]carbonyl}glycine;
4-Hydroxy-N-[(6-phenylpyridin-3-yl)methyl]-2-(1H-pyrazol-1-yl)pyrimidine-5-carboxamide;
N-{[6-(2-fluorophenyl)pyridin-3-yl]methyl}-4-hydroxy-2-(1H-pyrazol-1-yl)pyrimidine-5-carboxamide;
N-{[6-(3-fluorophenyl)pyridin-3-yl]methyl}-4-hydroxy-2-(1H-pyrazol-1-yl)pyrimidine-5-carboxamide trifluoroacetate;
N-{[6-(4-fluorophenyl)pyridin-3-yl]methyl}-4-hydroxy-2-(1H-pyrazol-1-yl)pyrimidine-5-carboxamide;
N-{[5-(4-fluorophenyl)pyrazin-2-yl]methyl}4-hydroxy-2-(1H-pyrazol-1-yl)pyrimidine-5-carboxamide;
N-[(6-cyanopyridin-3-yl)methyl]-4-hydroxy-2-(1H-pyrazol-1-yl)pyrimidine-5-carboxamide;
1-(4-Hydroxy-5-{[(1-methyl-1-phenylethyl)amino]carbonyl}pyrimidin-2-yl)-1H-pyrazole-4-carboxylic acid;
N-[1-(4-bromophenyl)-1-methylethyl]-4-hydroxy-2-(1H-pyrazol-1-yl)pyrimidine-5-carboxamide
4-hydroxy-N-(4-phenoxybenzyl)-2-(1H-pyrazol-1-yl)pyrimidine-5-carboxamide;
4-hydroxy-N-(1-phenylcyclohexyl)-2-(1H-pyrazol-1-yl)pyrimidine-5-carboxamide;

N-(4-benzoylbenzyl)-4-hydroxy-2-(1H-pyrazol-1-yl)pyrimidine-5-carboxamide;
N-[bis(4-methoxyphenyl)methyl]-4-hydroxy-2-(1H-pyrazol-1-yl)pyrimidine-5-carboxamide;
4-hydroxy-N-[4-(4-methylphenoxy)benzyl]-2-(1H-pyrazol-1-yl)pyrimidine-5-carboxamide;
N-(1-ethyl-1-phenylpropyl)-4-hydroxy-2-(1H-pyrazol-1-yl)pyrimidine-5-carboxamide;
N-[4-(4-fluorophenoxy)benzyl]-4-hydroxy-2-(1H-pyrazol-1-yl)pyrimidine-5-carboxamide;
4-hydroxy-N-[4-(2-methylphenoxy)benzyl]-2-(1H-pyrazol-1-yl)pyrimidine-5-carboxamide;
N-(2,3-dihydro-1-benzofuran-5-ylmethyl)-4-hydroxy-2-(1H-pyrazol-1-yl)pyrimidine-5-carboxamide;
N-9H-fluoren-9-yl-4-hydroxy-2-(1H-pyrazol-1-yl)pyrimidine-5-carboxamide;
methyl 4-[({[4-hydroxy-2-(1H-pyrazol-1-yl)pyrimidin-5-yl]carbonyl}amino)methyl]benzoate;
N-[(6-cyanopyridin-3-yl)(4-methoxyphenyl)methyl]-4-hydroxy-2-pyridazin-3-ylpyrimidine-5-carboxamide;
N-[(1S)-1-(4-cyanophenyl)ethyl]-4-hydroxy-2-(1H-pyrazol-1-yl)pyrimidine-5-carboxamide;
4-Hydroxy-N-[(4-methoxyphenyl)(6-methylpyridin-3-yl)methyl]-2-pyridazin-3-ylpyrimidine-5-carboxamide;
N-[(2,4-Dimethoxyphenyl)(6-methylpyridin-2-yl)methyl]-4-hydroxy-2-pyridazin-3-ylpyrimidine-5-carboxamide;
4-hydroxy-N-[(1S)-1-(4-methoxyphenyl)ethyl]-2-(1H-pyrazol-1-yl)pyrimidine-5-carboxamide;
4-hydroxy-N-[1-(4-methyl-1,3-thiazol-2-yl)ethyl]-2-(1H-pyrazol-1-yl)pyrimidine-5-carboxamide hydrochloride;
4-hydroxy-2-(1H-pyrazol-1-yl)-N-[1-(pyridin-2-yl)ethyl]pyrimidine-5-carboxamide;
N-[(1S)-2,3-dihydro-1H-inden-1-yl]-4-hydroxy-2-(1H-pyrazol-1-yl)pyrimidine-5-carboxamide;
4-hydroxy-N-[(1R,2S)-2-hydroxy-1,2-diphenylethyl]-2-(1H-pyrazol-1-yl)pyrimidine-5-carboxamide;
4-hydroxy-N-[(1S)-1-(naphthalen-2-yl)ethyl]-2-(1H-pyrazol-1-yl)pyrimidine-5-carboxamide;
4-hydroxy-N-[(1S)-2-hydroxy-1-phenylethyl]-2-(1H-pyrazol-1-yl)pyrimidine-5-carboxamide;
4-hydroxy-N-[(1R)-2-hydroxy-1-phenylethyl]-2-(1H-pyrazol-1-yl)pyrimidine-5-carboxamide;
(2R)-({[4-hydroxy-2-(1H-pyrazol-1-yl)pyrimidin-5-yl]carbonyl}amino)(phenyl)ethanoic acid;
4-hydroxy-N-[phenyl(pyridin-2-yl)methyl]-2-(1H-pyrazol-1-yl)pyrimidine-5-carboxamide trifluoroacetate;
4-hydroxy-N-[(1S)-1-(3-methoxyphenyl)ethyl]-2-(1H-pyrazol-1-yl)pyrimidine-5-carboxamide;
4-hydroxy-N-[(1R,2R)-2-hydroxy-1,2-diphenylethyl]-2-(1H-pyrazol-1-yl)pyrimidine-5-carboxamide;
4-hydroxy-N-[(1R)-2-hydroxy-2-methyl-1-phenylpropyl]-2-(1H-pyrazol-1-yl)pyrimidine-5-carboxamide;
4-hydroxy-N-[(1S)-1-(4-phenoxyphenyl)ethyl]-2-(1H-pyrazol-1-yl)pyrimidine-5-carboxamide;
4-hydroxy-2-(1H-pyrazol-1-yl)-N-{[5-(trifluoromethyl)pyridin-2-yl]methyl}pyrimidine-5-carboxamide;
4-hydroxy-N-(2-methyl-1-phenylpropyl)-2-(1H-pyrazol-1-yl)pyrimidine-5-carboxamide;
N-[(1S)-1-(2,3-dihydro-1,4-benzodioxin-6-yl)ethyl]-4-hydroxy-2-(1H-pyrazol-1-yl)pyrimidine-5-carboxamide;
4-hydroxy-2-(4-methyl-1H-pyrazol-1-yl)-N-[(1S)-1-phenylpropyl]pyrimidine-5-carboxamide;
4-hydroxy-N-[(1S)-1-(4-methoxyphenyl)ethyl]-2-(4-methyl-1H-pyrazol-1-yl)pyrimidine-5-carboxamide;
N-cyclohexyl-4-hydroxy-2-(pyridazin-3-yl)pyrimidine-5-carboxamide;
4-hydroxy-N-[phenyl(pyridin-2-yl)methyl]-2-pyridazin-3-ylpyrimidine-5-carboxamide trifluoroacetate;
4-hydroxy-N-[(1S)-1-(4-phenoxyphenyl)ethyl]-2-(pyridazin-3-yl)pyrimidine-5-carboxamide;
4-hydroxy-N-[(1R,2S)-2-hydroxy-1,2-diphenylethyl]-2-(pyridazin-3-yl)pyrimidine-5-carboxamide;
4-hydroxy-N-[(1R,2R)-2-hydroxy-1,2-diphenylethyl]-2-(pyridazin-3-yl)pyrimidine-5-carboxamide;
N-[(1S)-1-(2,3-dihydro-1,4-benzodioxin-6-yl)ethyl]-4-hydroxy-2-(pyridazin-3-yl)pyrimidine-5-carboxamide;
4-hydroxy-2-(1H-pyrazol-1-yl)-N-{(1S)-1-[6-(trifluoromethyl)pyridin-3-yl]ethyl}pyrimidine-5-carboxamide;
4-hydroxy-2-(1H-pyrazol-1-yl)-N-{(1R)-1-[6-(trifluoromethyl)pyridin-3-yl]ethyl}pyrimidine-5-carboxamide;
4-hydroxy-2-(1H-pyrazol-1-yl)-N-{1-[6-(trifluoromethyl)pyridin-3-yl]ethyl}pyrimidine-5-carboxamide;
4-hydroxy-N-{phenyl[6-(trifluoromethyl)pyridin-3-yl]methyl}-2-(1H-pyrazol-1-yl)pyrimidine-5-carboxamide;
4-hydroxy-N-{(S)-phenyl[6-(trifluoromethyl)pyridin-3-yl]methyl}-2-(1H-pyrazol-1-yl)pyrimidine-5-carboxamide;
4-hydroxy-N-{(R)-phenyl[6-(trifluoromethyl)pyridin-3-yl]methyl}-2-(1H-pyrazol-1-yl)pyrimidine-5-carboxamide;
4-hydroxy-N-[(4-methoxyphenyl)(4-methyl-1,3-thiazol-2-yl)methyl]-2-(pyridazin-3-yl)pyrimidine-5-carboxamide;
4-hydroxy-N-[(S)-(4-methoxyphenyl)(4-methyl-1,3-thiazol-2-yl)methyl]-2-(pyridazin-3-yl)pyrimidine-5-carboxamide;
4-hydroxy-N-[(R)-(4-methoxyphenyl)(4-methyl-1,3-thiazol-2-yl)methyl]-2-(pyridazin-3-yl)pyrimidine-5-carboxamide;
4-hydroxy-N-[(4-methoxyphenyl)(6-methylpyridin-3-yl)methyl]-2-(pyridazin-3-yl)pyrimidine-5-carboxamide;
4-hydroxy-N-[(S)-(4-methoxyphenyl)(6-methylpyridin-3-yl)methyl]-2-(pyridazin-3-yl)pyrimidine-5-carboxamide;
4-hydroxy-N-[(R)-(4-methoxyphenyl)(6-methylpyridin-3-yl)methyl]-2-(pyridazin-3-yl)pyrimidine-5-carboxamide;
N-[(3-cyanophenyl)(4-methoxyphenyl)methyl]-4-hydroxy-2-(pyridazin-3-yl)pyrimidine-5-carboxamide;
N-[(S)-(3-cyanophenyl)(4-methoxyphenyl)methyl]-4-hydroxy-2-(pyridazin-3-yl)pyrimidine-5-carboxamide;
N-[(R)-(3-cyanophenyl)(4-methoxyphenyl)methyl]-4-hydroxy-2-(pyridazin-3-yl)pyrimidine-5-carboxamide;
N-[(2,4-dimethoxyphenyl)(6-methylpyridin-2-yl)methyl]-4-hydroxy-2-(pyridazin-3-yl)pyrimidine-5-carboxamide;
N-[(S)-(2,4-dimethoxyphenyl)(6-methylpyridin-2-yl)methyl]-4-hydroxy-2-(pyridazin-3-yl)pyrimidine-5-carboxamide;
N-[(R)-(2,4-dimethoxyphenyl)(6-methylpyridin-2-yl)methyl]-4-hydroxy-2-(pyridazin-3-yl)pyrimidine-5-carboxamide;
N-[(4-cyanophenyl)(4-methoxyphenyl)methyl]-4-hydroxy-2-(pyridazin-3-yl)pyrimidine-5-carboxamide;
N-[(S)-(4-cyanophenyl)(4-methoxyphenyl)methyl]-4-hydroxy-2-(pyridazin-3-yl)pyrimidine-5-carboxamide;
N-[(R)-(4-cyanophenyl)(4-methoxyphenyl)methyl]-4-hydroxy-2-(pyridazin-3-yl)pyrimidine-5-carboxamide;
4-hydroxy-N-{(4-methoxyphenyl)[4-(trifluoromethoxy)phenyl]methyl}-2-(pyridazin-3-yl)pyrimidine-5-carboxamide;
4-hydroxy-N-{(S)-(4-methoxyphenyl)[4-(trifluoromethoxy)phenyl]methyl}-2-(pyridazin-3-yl)pyrimidine-5-carboxamide;
4-hydroxy-N-{(R)-(4-methoxyphenyl)[4-(trifluoromethoxy)phenyl]methyl}-2-(pyridazin-3-yl)pyrimidine-5-carboxamide;
N-[(4-cyanophenyl)(2,4-dimethoxyphenyl)methyl]-4-hydroxy-2-(pyridazin-3-yl)pyrimidine-5-carboxamide;

N-[(S)-(4-cyanophenyl)(2,4-dimethoxyphenyl)methyl]-4-hydroxy-2-(pyridazin-3-yl)pyrimidine-5-carboxamide;
N-[(R)-(4-cyanophenyl)(2,4-dimethoxyphenyl)methyl]-4-hydroxy-2-(pyridazin-3-yl)pyrimidine-5-carboxamide;
4-hydroxy-N-[(4-hydroxyphenyl)(4-methoxyphenyl)methyl]-2-(pyridazin-3-yl)pyrimidine-5-carboxamide;
4-hydroxy-N-[(S)-(4-hydroxyphenyl)(4-methoxyphenyl)methyl]-2-(pyridazin-3-yl)pyrimidine-5-carboxamide;
4-hydroxy-N-[(R)-(4-hydroxyphenyl)(4-methoxyphenyl)methyl]-2-(pyridazin-3-yl)pyrimidine-5-carboxamide;
N-[1-(4-cyanophenyl)-3-methylbutyl]-4-hydroxy-2-(pyridazin-3-yl)pyrimidine-5-carboxamide;
N-[(S)-1-(4-cyanophenyl)-3-methylbutyl]-4-hydroxy-2-(pyridazin-3-yl)pyrimidine-5-carboxamide;
N-[(R)-1-(4-cyanophenyl)-3-methylbutyl]-4-hydroxy-2-(pyridazin-3-yl)pyrimidine-5-carboxamide;
N-[1-(4-cyanophenyl)-2-(4-methoxyphenyl)ethyl]-4-hydroxy-2-(pyridazin-3-yl)pyrimidine-5-carboxamide;
N-[(S)-1-(4-cyanophenyl)-2-(4-methoxyphenyl)ethyl]-4-hydroxy-2-(pyridazin-3-yl)pyrimidine-5-carboxamide;
N-[(R)-1-(4-cyanophenyl)-2-(4-methoxyphenyl)ethyl]-4-hydroxy-2-(pyridazin-3-yl)pyrimidine-5-carboxamide;
N-[(4-cyanophenyl)(cyclohexyl)methyl]-4-hydroxy-2-(pyridazin-3-yl)pyrimidine-5-carboxamide;
N-[(S)-(4-cyanophenyl)(cyclohexyl)methyl]-4-hydroxy-2-(pyridazin-3-yl)pyrimidine-5-carboxamide;
N-[(R)-(4-cyanophenyl)(cyclohexyl)methyl]-4-hydroxy-2-(pyridazin-3-yl)pyrimidine-5-carboxamide;
N-[2,3-dihydro-1-benzofuran-5-yl(4-methoxyphenyl)methyl]-4-hydroxy-2-(pyridazin-3-yl)pyrimidine-5-carboxamide;
N-[(S)-2,3-dihydro-1-benzofuran-5-yl(4-methoxyphenyl)methyl]-4-hydroxy-2-(pyridazin-3-yl)pyrimidine-5-carboxamide;
N-[(R)-2,3-dihydro-1-benzofuran-5-yl(4-methoxyphenyl)methyl]-4-hydroxy-2-(pyridazin-3-yl)pyrimidine-5-carboxamide;
N-[1-(biphenyl-4-yl)butyl]-4-hydroxy-2-(1H-pyrazol-1-yl)pyrimidine-5-carboxamide;
4-hydroxy-N-[(4-methoxyphenyl)(pyrazin-2-yl)methyl]-2-(1H-pyrazol-1-yl)pyrimidine-5-carboxamide;
4-hydroxy-N-[(4-methoxyphenyl)(6-methoxypyridin-3-yl)methyl]-2-(1H-pyrazol-1-yl)pyrimidine-5-carboxamide trifluoroacetate;
4-hydroxy-N-{(4-methoxyphenyl)[4-(methylsulfanyl)phenyl]methyl}-2-(1H-pyrazol-1-yl)pyrimidine-5-carboxamide;
N-[(6-chloropyridin-3-yl)(4-methoxyphenyl)methyl]-4-hydroxy-2-(pyridazin-3-yl)pyrimidine-5-carboxamide;
4-hydroxy-N-[(4-methoxyphenyl)(6-methoxypyridin-3-yl)methyl]-2-(pyridazin-3-yl)pyrimidine-5-carboxamide;
4-hydroxy-N-[(4-methoxyphenyl)(quinolin-2-yl)methyl]-2-(pyridazin-3-yl)pyrimidine-5-carboxamide;
4-hydroxy-N-[(4-methoxyphenyl)(6-methoxyquinolin-2-yl)methyl]-2-(pyridazin-3-yl)pyrimidine-5-carboxamide;
N-[1,3-benzothiazol-2-yl(4-methoxyphenyl)methyl]-4-hydroxy-2-(pyridazin-3-yl)pyrimidine-5-carboxamide;
N-[bis(2,4-dimethoxyphenyl)methyl]-4-hydroxy-2-(pyridazin-3-yl)pyrimidine-5-carboxamide;
N-[bis(4-methoxy-2-methylphenyl)methyl]-4-hydroxy-2-(pyridazin-3-yl)pyrimidine-5-carboxamide;
N-[(2,4-dimethoxyphenyl)(4-fluorophenyl)methyl]-4-hydroxy-2-(pyridazin-3-yl)pyrimidine-5-carboxamide;
N-[(2,6-dimethoxypyridin-3-yl)(4-fluorophenyl)methyl]-4-hydroxy-2-(pyridazin-3-yl)pyrimidine-5-carboxamide;
4-hydroxy-N-{(4-methoxyphenyl)[4-(methylsulfanyl)phenyl]methyl}-2-(pyridazin-3-yl)pyrimidine-5-carboxamide;
N-{(4-chlorophenyl)[4-(1-hydroxyethyl)phenyl]methyl}-4-hydroxy-2-(pyridazin-3-yl)pyrimidine-5-carboxamide;
4-Hydroxy-N-((1R)-2-oxo-1-phenyl-2-{[(1R)-1-phenylethyl]amino}ethyl)-2-(1H-pyrazol-1-yl)pyrimidine-5-carboxamide;
4-Hydroxy-N-[[4-(methoxymethyl)phenyl](4-methoxyphenyl)methyl]-2-pyridazin-3-ylpyrimidine-5-carboxamide;
4-Hydroxy-N-[[(S)-4-(methoxymethyl)phenyl](4-methoxyphenyl)methyl]-2-pyridazin-3-ylpyrimidine-5-carboxamide;
4-Hydroxy-N-[[(R)-4-(methoxymethyl)phenyl](4-methoxyphenyl)methyl]-2-pyridazin-3-ylpyrimidine-5-carboxamide;
N-{bis[4-(methoxymethyl)phenyl]methyl}4-hydroxy-2-pyridazin-3-ylpyrimidine-5-carboxamide;
4-hydroxy-N-[(1S)-1-(4-isoquinolin-5-ylphenyl)ethyl]-2-pyridazin-3-ylpyrimidine-5-carboxamide;
N-{(1S)-1-[4-(6-fluoropyridin-3-yl)phenyl]ethyl}4-hydroxy-2-pyridazin-3-ylpyrimidine-5-carboxamide trifluoroacetate;
4-hydroxy-2-pyridazin-3-yl-N-[(1S)-1-(4-pyridin-3-ylphenyl)ethyl]pyrimidine-5-carboxamide trifluoroacetate;
N-{[4-hydroxy-2-(1H-pyrazol-1-yl)pyrimidin-5-yl]carbonyl}-2-methylalanine;
N-[1-(2,3-dihydro-1H-indol-1-yl)-2-methyl-1-oxopropan-2-yl]-4-hydroxy-2-(1H-pyrazol-1-yl)pyrimidine-5-carboxamide;
4-hydroxy-N-[(S-(4-methoxyphenyl)(6-methoxypyridin-3-yl)methyl]-2-(pyridazin-3-yl)pyrimidine-5-carboxamide;
4-hydroxy-N-[(R)-(4-methoxyphenyl)(6-methoxypyridin-3-yl)methyl]-2-(pyridazin-3-yl)pyrimidine-5-carboxamide;
N-[bis(6-methoxypyridin-3-yl)methyl]-4-hydroxy-2-(pyridazin-3-yl)pyrimidine-5-carboxamide;
and pharmaceutically acceptable salts and solvates thereof.

One embodiment of the invention provides compounds of formula II and pharmaceutically acceptable salts and solvates thereof:

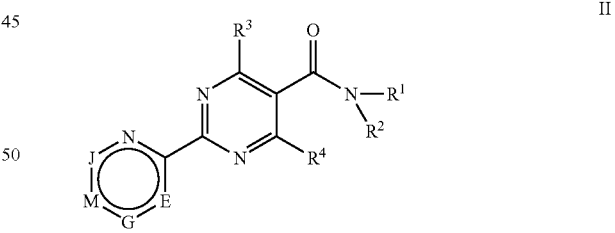

E, G, M, and J are each independently chosen from N and C, provided that at least one of E, G, M, and J is C, optionally, E, G, M, and J are each independently substituted by one or more $R^9$;

$R^1$ is selected from —$C_{1-10}$ alkyl, —$CO_{1-10}$ alkyl-$C_{3-10}$ cycloalkyl, —$C_{2-10}$ alkenyl, —$C_{0-10}$ alkyl-$C_{5-10}$ cycloalkenyl, —$C_{2-10}$ alkynyl, —$C_{1-10}$ alkylaryl, —$C_{1-10}$ alkylheterocyclyl, —$NR^bR^c$, and —$C_{0-10}$ alkyl $C_{3-10}$ heterocycloalkyl, wherein in $R^1$ said alkyl, alkenyl, alkynyl, cycloalkenyl, aryl, heterocycloalkyl, heterocyclyl, and cycloalkyl are each optionally substituted with one or more $R^8$ substituents, and optionally two $R^8$ may join together to form a 3 to 8 member ring;

R² is selected from hydrogen, —C₁₋₁₀ alkyl, aryl, —C₃-C₁₀ cycloalkyl, and heterocyclyl, wherein C₁₋₁₀ alkyl, —C₃-C₁₀ cycloalkyl, aryl, and heterocyclyl is unsubstituted or substituted with one or more substituents selected from halo, hydroxyl, C₁₋₁₀ alkyl, and —OC₁₋₁₀ alkyl;

R³ is selected from hydrogen, halogen, hydroxy, —C₁₋₆ alkyl, —C₁₋₆ alkoxy, heterocyclyl, —NR^b R^c, and —SC₀₋₆ alkyl, wherein said alkyl, and alkoxy, are optionally substituted by one or more substituents R¹⁰;

R⁴ is selected from hydrogen, —C₁₋₁₀ alkyl, —C₂₋₁₀ alkenyl, —C₂₋₁₀ alkynyl, —C₃₋₁₀ heterocycloalkyl, —(C₀₋₁₀ alkyl)aryl, (C₀₋₁₀ alkyl)heterocyclyl, —C₅₋₁₀ cycloalkenyl, and —NR^b R^c, wherein said alkyl, alkenyl, alkynyl, cycloalkyl, cycloalkenyl, aryl, and heterocyclyl are optionally substituted by one or more substituents R⁹;

optionally R¹ and R², are linked together to form a ring of 5 to 8 atoms optionally substituted with one or more substituents R⁹;

R⁸ is selected from halogen, hydroxyl, —C₁₋₁₀ alkyl, —C₁₋₁₀ alkenyl, —C₁₋₁₀ alkynyl, —OC₁₋₁₀ alkylaryl, aryl, heterocyclyl, —C₃₋₁₀ cycloalkyl, —C₃₋₁₀ heterocycloalkyl, cyano, oxo, —OC₁₋₁₀ alkyl, C₂₋₆ alkylaminocarbonylamino, C₀₋₁₀ alkyloxycarbonylaminoC₀₋₆ alkyl, C₀₋₁₀ alkylcarbonylaminoC₀₋₆ alkyl, C₂₋₆ alkylaminosulfonylaminoC₀₋₄ alkyl, —C₂₋₆ alkylsulfonylaminoC₀₋₄ alkyl, —C₁₋₄ alkylsulfonyl, arylsulfonyl, —C₁₋₁₀ alkylamninosulfonyl, C₁₋₁₀ alkylaminocarbonyl, —(C=O)N(C₀₋₆ alkyl)₂, difluoromethoxy, trifluoromethoxy, trifluoroethoxy, —SR^a, and NR^b R^c, wherein said alkyl, alkenyl, alkynyl, aryl, heterocyclyl, cycloalkyl, heterocycloalkyl may optionally be substituted with one or more groups selected from hydroxyl, —CO₂H, halogen, —OC₁₋₁₀ alkyl, and C₁₋₆ alkyl;

R⁹ is selected from halogen, hydroxy, oxo, aryl, heterocyclyl, —C₁₋₆ alkyl, —C₃₋₁₀ cycloalkyl, —C₃₋₁₀ heterocycloalkyl, —(C₁₋₁₀ alkyl)aryl, —(C₀₋₁₀ alkyl)heterocyclyl, —C₅₋₁₀ cycloalkenyl, —C₂₋₁₀ alkynyl, —C₁₋₆ alkoxy, aryloxy, heterocyclyloxy, —CO₂R^a, —NR^b R^c, —CONR^b R^c, —OCO₂R^a, —OCONR^b R^c, —NR^d CO₂R^a, —NR^d CONR^b R^c, —SR^a and —S(O)ₙR^d, wherein said aryl, heterocyclyl, alkoxy, aryloxy, heterocyclyloxy are optionally substituted by one or more substituents R¹⁰;

R¹⁰ is selected from aryl, heterocyclyl, halogen, —C₁₋₆ alkyl, —C₁₋₆ alkoxy, CO₂R^a, cyano, O(C=O) C₁₋₆ alkyl, NO₂, difluoromethoxy, trifluoromethoxy, trifluoroethoxy, —O₍₀₋₁₎(C₁₋₁₀)perfluoroalkyl, C₀₋₁₀ alkylaminocarbonylamino, C₀₋₁₀ alkyloxycarbonylaminoC₀₋₁₀ alkyl, C₀₋₁₀ alkylcarbonylaminoC₀₋₁₀ alkyl, C₀₋₁₀ alkylaminocarbonyl, C₀₋₁₀ alkylaminosulfonylaminoC₀₋₁₀ alkyl, C₀₋₁₀ alkylsulfonylaminoC₀₋₁₀ alkyl, C₀₋₁₀ alkylsulfonyl, C₀₋₁₀ alkylaminosulfonyl, —(C=O)N(C₀₋₆ alkyl)₂, —S(C₀₋₆ alkyl), and NH₂;

n is 1 or 2;

R^a is chosen from hydrogen; —C₁₋₁₀ alkyl, —(C₁₋₆ alkyl)C₃₋₈ cycloalkyl; and —(C₁₋₆ alkyl)phenyl; and R^b, R^c, and R^d are each independently chosen from hydrogen, —C₁₋₁₀ alkyl, —C₃₋₁₀ cycloalkyl, —C₃₋₁₀ heterocycloalkyl, aryl, and heterocyclyl, wherein said alkyl, cycloalkyl, aryl and heterocyclyl are optionally substituted by one or more substituents R¹⁰.

Another embodiment of the invention provides compounds of formula III

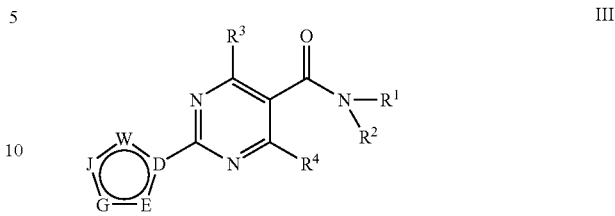

III

D is C or N;

W is N, O, or S;

E, G, and J are each independently chosen from N, C, O, and S, provided that at least one of E, G, and J is C, optionally, E, G, and J are each independently substituted by one or more R⁹;

R¹ is selected from —C₁₋₁₀ alkyl, —C₀₋₁₀ alkyl-C₃₋₁₀ cycloalkyl, —C₂₋₁₀ alkenyl, —C₀₋₁₀ alkyl-C₅₋₁₀ cycloalkenyl, —C₂₋₁₀ alkynyl, —C₀₋₁₀ alkylaryl, —C₀₋₁₀ alkylheterocyclyl, —NR^b R^c, and —C₀₋₁₀ alkyl C₃₋₁₀ heterocycloalkyl, wherein in R¹ said alkyl, alkenyl, alkynyl, cycloalkenyl, aryl, heterocycloalkyl, heterocyclyl, and cycloalkyl are each optionally substituted with one or more R⁸ substituents, and optionally two R⁸ may join together to form a 3 to 8 member ring;

R² is selected from hydrogen, —C₁₋₁₀ alkyl, aryl, —C₃-C₁₀ cycloalkyl, and heterocyclyl, wherein C₁₋₁₀ alkyl, —C₃-C₁₀ cycloalkyl, aryl, and heterocyclyl is unsubstituted or substituted with one or more substituents selected from halo, hydroxyl, C₁₋₁₀ alkyl, and —OC₁₋₁₀ alkyl;

R³ is selected from hydrogen, halogen, hydroxy, —C₁₋₆ alkyl, —C₁₋₆ alkoxy, heterocyclyl, —NR^b R^c, and —S C₀₋₆ alkyl, wherein said alkyl, and alkoxy, are optionally substituted by one or more substituents R¹⁰;

R⁴ is selected from hydrogen, -C₁-C₁₀ alkyl, —C₂₋₁₀ alkenyl, —C₂₋₁₀ alkynyl, —C₃₋₁₀ cycloalkyl, —C₃₋₁₀ heterocycloalkyl, —(C₀₋₁₀ alkyl)aryl, (C₀₋₁₀ alkyl)heterocyclyl, —C₅₋₁₀ cycloalkenyl, and —NR^b R^c, wherein said alkyl, alkenyl, alkynyl, cycloalkyl, cycloalkenyl, aryl, and heterocyclyl are optionally substituted by one or more substituents R⁹;

optionally R¹ and R², are linked together to form a ring of 5 to 8 atoms optionally substituted with one or more substituents R⁹;

R⁸ is selected from halogen, hydroxyl, —C₁₋₁₀ alkyl, —C₁₋₁₀ alkenyl, —C₁₋₁₀ alkynyl, —OC₁₋₁₀ alkylaryl, aryl, heterocyclyl, —C₃₋₁₀ cycloalkyl, —C₃₋₁₀ heterocycloalkyl, cyano, oxo, —OC₁₋₁₀ alkyl, C₂₋₆ alkylaminocarbonylamino, C₀₋₁₀ alkyloxycarbonylamninoC₀₋₆ alkyl, C₀₋₁₀ alkylcarbonylaminoC₀₋₆ alkyl, C₂₋₆ alkylaminosulfonylaminoC₀₋₄ alkyl, —C₂₋₆ alkylsulfonylaminoC₀₋₄ alkyl, —C₁₋₄ alkylsulfonyl, arylsulfonyl, —C₁₋₁₀ alkylaminosulfonyl, C₁₋₁₀ alkylaminocarbonyl, —(C=O)N(C₀₋₆ alkyl)₂, difluoromethoxy, trifluoromethoxy, trifluoroethoxy, —SR^a, and NR^b R^c wherein said alkyl, alkenyl, alkynyl, aryl, heterocyclyl, cycloalkyl, heterocycloalkyl may optionally be substituted with one or more groups selected from hydroxyl, —CO₂H, halogen, —OC₁₋₁₀ alkyl, and C₁₋₆ alkyl;

R⁹ is selected from halogen, hydroxy, oxo, aryl, heterocyclyl, —C₁₋₆ alkyl, —C₃₋₁₀ cycloalkyl, —C₃₋₁₀ heterocycloalkyl, —(C₁₋₁₀ alkyl)aryl, —(C₀₋₁₀ alkyl)heterocyclyl, —C₅₋₁₀ cycloalkenyl, —C₂₋₁₀ alkynyl, —C₁₋₆ alkoxy, aryloxy, heterocyclyloxy, —CO₂Rᵃ, —NRᵇRᶜ, —CONRᵇRᶜ, —OCO₂Rᵃ, —OCONRᵇRᶜ, —NRᵈCO₂Rᵃ, —NRᵈ-CONRᵇRᶜ, —SRᵃ and —S(O)ₙRᵈ, wherein said aryl, heterocyclyl, alkoxy, aryloxy, heterocyclyloxy are optionally substituted by one or more substituents R¹⁰;

R¹⁰ is selected from aryl, heterocyclyl, halogen, —C₁₋₆ alkyl, —C₁₋₆ alkoxy, CO₂Rᵃ, cyano, O(C=O) C₁₋₆ alkyl, NO₂, difluoromethoxy, trifluoromethoxy, trifluoroethoxy, —O₍₀₋₁₎(C₁₋₁₀)perfluoroalkyl, C₀₋₁₀ alkylaminocarbonylamino, C₀₋₁₀ alkyloxycarbonylaminoC₀₋₁₀ alkyl, C₀₋₁₀ alkylcarbonylaminoC₀₋₁₀ alkyl, C₀₋₁₀ alkylaminocarbonyl, C₀₋₁₀ alkylaminosulfonylaminoC₀₋₁₀ alkyl, C₀₋₁₀ alkylsulfonylaminoC₀₋₁₀ alkyl, C₀₋₁₀ alkylsulfonyl, C₀₋₁₀ alkylamninosulfonyl, —(C=O)N(C₀₋₆ alkyl)₂, —S(C₀₋₆ alkyl), and NH₂;

n is 1 or 2;

Rᵃ is chosen from hydrogen; —C₁₋₁₀ alkyl, —(C₁₋₆ alkyl)C₃₋₈ cycloalkyl; and —(C₁₋₆ alkyl)phenyl; and Rᵇ, Rᶜ, and Rᵈ are each independently chosen from hydrogen, —C₁₋₁₀ alkyl, —C₃₋₁₀ cycloalkyl, —C₃₋₁₀ heterocycloalkyl, aryl, and heterocyclyl, wherein said alkyl, cycloalkyl, aryl and heterocyclyl are optionally substituted by one or more substituents R¹⁰.

As used herein except where noted, "alkyl" is intended to include both branched- and straight-chain saturated aliphatic hydrocarbon groups, including all isomers, having the specified number of carbon atoms. Commonly used abbreviations for alkyl groups are used throughout the specification, e.g. methyl may be represented by "Me" or CH₃, ethyl may be represented by "Et" or CH₂CH₃, propyl may be represented by "Pr" or CH₂CH₂CH₃, butyl may be represented by "Bu" or CH₂CH₂CH₂CH₃, etc. "C₁₋₆ alkyl" (or "C₁-C₆ alkyl") for example, means linear or branched chain alkyl groups, including all isomers, having the specified number of carbon atoms. C₁₋₆ alkyl includes all of the hexyl alkyl and pentyl alkyl isomers as well as n-, iso-, sec- and t-butyl, n- and isopropyl, ethyl and methyl. "C₁₋₄ alkyl" means n-, iso-, sec- and t-butyl, n- and isopropyl, ethyl and methyl. The term "alkylene" refers to both branched- and straight-chain saturated aliphatic hydrocarbon groups, including all isomers, having the specified number of carbons, and having two terminal end chain attachments. For illustration, the term "unsubstituted A-C₄alkylene-B" represents A-CH₂—CH₂—CH₂—CH₂—B. The term "alkoxy" represents a linear or branched alkyl group of indicated number of carbon atoms attached through an oxygen bridge.

Unless otherwise specifically noted as only "unsubstituted" or only "substituted", or when substituents are enumerated, alkyl (either as a stand alone radical or as part of a radical such as alkoxy, alkylthio and aralkyl) groups are unsubstituted or substituted with 1 to 3 substituents on each carbon atom, with halo, C₁-C₂₀ alkyl, CF₃, NH₂, N(C₁-C₆ alkyl)₂, NO₂, oxo, CN, N₃, —OH, —O(C₁-C₆ alkyl), C₃-C₁₀ cycloalkyl, C₂-C₆ alkenyl, C₂-C₆ alkynyl, (C₀-C₆ alkyl)S(O)₀₋₂—, (C₀-C₆ alkyl)S(O)₀₋₂(C₀-C₆ alkyl)-, (C₀-C₆ alkyl)C(O)NH—, H₂N—C(NH)—, —O(C₁-C₆ alkyl)CF₃, (C₀-C₆ alkyl)C(O)—, (C₀-C₆ alkyl)OC(O)—, (C₀-C₆ alkyl)O(C₁-C₆ alkyl)-, (C₀-C₆ alkyl)C(O)₁₋₂(C₀-C₆ alkyl)-, (C₀-C₆ alkyl)OC(O)NH—, —NH(C₁-C₆ alkyl)NHC(O)NH(C₁-C₆ alkyl), NHC(O)OC₁-C₆ alkyl, —NH(C₁-C₆ alkyl)NHSO₂(C₁-C₆ alkyl), —(C₀-C₆ alkyl)NHSO₂(C₁-C₆ alkyl), aryl, aralkyl, heterocycle, heterocyclylalkyl, halo-aryl, halo-aralkyl, haloheterocycle, halo-heterocyclylalkyl, cyano-aryl, cyanoaralkyl, cyano-heterocycle and cyano-heterocyclylalkyl.

The term "C₀" as employed in expressions such as "C₀₋₆ alkyl" means a direct covalent bond; or when the term appears at the terminus of a substituent, C₀₋₆ alkyl means hydrogen or C1-6alkyl. Similarly, when an integer defining the presence of a certain number of atoms in a group is equal to zero, it means that the atoms adjacent thereto are connected directly by a bond. For example, in the structure

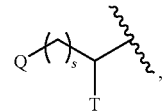

wherein s is an integer equal to zero, 1 or 2, the structure is

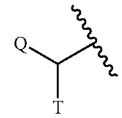

when s is zero.

The term "C₃₋₈ cycloalkyl" (or "C₃-C₈ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "C₃₋₇ cycloalkyl", "C₃₋₆ cycloalkyl", "C₅₋₇ cycloalkyl" and the like have analogous meanings.

The term "halogen" (or "halo") refers to fluorine, chlorine, bromine and iodine (alternatively referred to as fluoro (F), chloro (Cl), bromo (Br), and iodo (I)).

The term "aryl" refers to aromatic mono- and poly-carbocyclic ring systems, wherein the individual carbocyclic rings in the polyring systems are fused or attached to each other via a single bond. Suitable aryl groups include phenyl, naphthyl, and biphenylenyl.

The term "carbocycle" (and variations thereof such as "carbocyclic" or "carbocyclyl") as used herein, unless otherwise indicated, refers to (i) a C₃ to C₈ monocyclic, saturated or unsaturated ring or (ii) a C₇ to C₁₂ bicyclic saturated or unsaturated ring system. Each ring in (ii) is either independent of, or fused to, the other ring, and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a C₇ to C₁₀ bicyclic ring system in which each ring is saturated or unsaturated and two adjacent carbon atoms are shared by each of the rings in the ring system. A fused bicyclic carbocycle in which one ring is saturated and the other is saturated is a saturated bicyclic ring system. A fused bicyclic carbocycle in which one ring is benzene and the other is saturated is an unsaturated bicyclic ring system. A fused bicyclic carbocycle in which one ring is benzene and the other is unsaturated is an unsaturated ring system. Saturated carbocyclic rings are also referred to as cycloalkyl rings, e.g., cyclopropyl, cyclobutyl, etc. Unless otherwise noted, carbocycle is unsubstituted or substituted with C₁₋₆ alkyl, C₁₋₆ alkenyl, C₁₋₆ alkynyl, aryl, halogen, NH₂ or OH. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

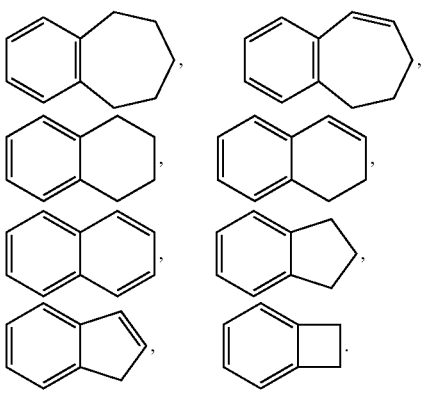

The term "heterocycle" (and variations thereof such as "heterocyclic" or "heterocyclyl") broadly refers to (i) a stable 4- to 8-membered, saturated or unsaturated monocyclic ring, or (ii) a stable 7- to 12-membered bicyclic ring system, wherein each ring in (ii) is independent of, or fused to, the other ring or rings and each ring is saturated or unsaturated, and the monocyclic ring or bicyclic ring system contains one or more heteroatoms (e.g., from 1 to 6 heteroatoms, or from 1 to 4 heteroatoms) selected from N, O and S and a balance of carbon atoms (the monocyclic ring typically contains at least one carbon atom and the ring systems typically contain at least two carbon atoms); and wherein any one or more of the nitrogen and sulfur heteroatoms is optionally oxidized, and any one or more of the nitrogen heteroatoms is optionally quaternized. Unless otherwise specified, the heterocyclic ring may be attached at any heteroatom or carbon atom, provided that attachment results in the creation of a stable structure. Unless otherwise specified, when the heterocyclic ring has substituents, it is understood that the substituents may be attached to any atom in the ring, whether a heteroatom or a carbon atom, provided that a stable chemical structure results.

Non limiting examples of heterocyclylic moieties include, but are not limited to, the following: azabenzimidazole, benzoimidazolyl, benzofuryl, benzofurazanyl, benzopyrazolyl, benzothiazolyl, benzothienyl, benzotriazolyl, benzothiophenyl, benzoxazolyl, carbazolyl, carbolinyl, chromanyl, cinnolinyl, furanyl, imidazolyl, indolinyl, indolyl, indolazinyl, indazolyl, isobenzofuryl, isochromanyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridinyl, pyrimidyl, pyrrolyl, quinazolinyl, quinolyl, quinoxalinyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuryl, dihydrobenzothiophenyl, dihydrobenzoxazolyl, dihydrofuryl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, tetrahydroquinolinyl, tetrahydroisoquinolinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuryl, tetrahydrothienyl, tetrahydroquinolinyl, 2,3-dihydrobenzofuryl, 2,3-dihydrobenzo-1,4-dioxinyl, imidazo(2,1-b)(1,3)thiazole, and benzo-1,3-dioxolyl.

Saturated heterocyclics form a subset of the heterocycles; i.e., the term "saturated heterocyclic" generally refers to a heterocycle as defined above in which the entire ring system (whether mono- or poly-cyclic) is saturated. The term "saturated heterocyclic ring" refers to a 4- to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic which consists of carbon atoms and one or more heteroatoms selected from N, O and S. In the case of substituted heteroaryl rings containing at least one nitrogen atom (e.g., pyridine), such substitutions can be those resulting in N-oxide formation. Representative examples of heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuryl, 2,3-dihydrobenzo-1,4-dioxinyl

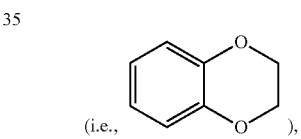

(i.e., ), imidazo(2,1-b)(1,3)thiazole,

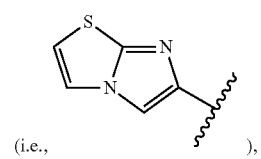

(i.e., ), and benzo-1,3-dioxolyl

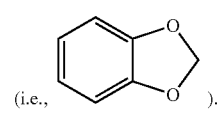

(i.e., ).

In certain contexts herein,

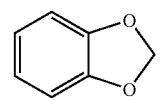

is alternatively referred to as phenyl having as a substituent methylenedioxy attached to two adjacent carbon atoms.

The terms "arylalkyl" and "alkylaryl" include an alkyl portion where alkyl is as defined above and include an aryl portion where aryl is as defined above. Examples of arylalkyl include, but are not limited to, benzyl, phenylethyl, phenylpropyl, naphthylmethyl, and naphthylethyl. Examples of alkylaryl include, but are not limited to, toluene, ethylbenzene, propylbenzene, methylpyridine, ethylpyridine, propylpyridine and butylpyridine.

Unless otherwise specifically noted as only "unsubstituted" or only "substituted", or when substituents are specifically enumerated, cycloalkyl, aryl (including phenyl) and heterocycle (including heteroaryl) groups are unsubstituted or substituted. As used herein, the terms "substituted $C_3$-$C_{10}$ cycloalkyl", "substituted aryl (including phenyl)" and "substituted heterocycle" are intended to include the cyclic group containing from 1 to 3 substituents in addition to the point of attachment to the rest of the compound. Preferably, the substituents are selected from the group which includes, but are not limited to, halo, $C_1$-$C_{20}$ alkyl, $CF_3$, $NH_2$, $N(C_1$-$C_6$ alkyl$)_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl)S(O)$_{0-2}$—, aryl-S(O)$_{0-2}$—, ($C_0$-$C_6$ alkyl)S(O)$_{0-2}$($C_0$-$C_6$ alkyl)-, ($C_0$-$C_6$ alkyl)C(O)NH—, $H_2$N—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$ alkyl)$_2$NC(O)— ($C_0$-$C_6$alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, aryl, aralkyl, heteroaryl, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed.

The term "oxy" means an oxygen (O) atom. The term "thio" means a sulfur (S) atom. The term "oxo" means "=O". The term "carbonyl" means "C=O."

When any variable (e.g., $R^2$, $R^3$, etc.) occurs more than one time in any substituent or in formulas I-III, its definition in each occurrence is independent of its definition at every other occurrence. Also, combinations of substituents and/or variables are permissible only if such combinations result in stable compounds.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to

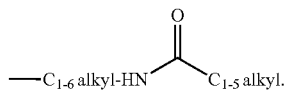

In choosing compounds of the present invention, one of ordinary skill in the art will recognize that the various substituents, i.e. $R^1$, $R^2$, $R^3$, etc., are to be chosen in conformity with well-known principles of chemical structure connectivity.

Lines drawn into the ring systems from substituents indicate that the indicated bond can be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups can be on the same carbon or on different carbons, so long as a stable structure results. The phrase "optionally substituted with one or more substituents" should be taken to be equivalent to the phrase "optionally substituted with at least one substituent" and in such cases one embodiment will have from zero to three substituents.

In one embodiment, A, includes, but is not limited to, the following: azabenzimidazole, benzoimidazolyl, benzofuryl, benzofurazanyl, benzopyrazolyl, benzothiazolyl, benzothienyl, benzotriazolyl, benzothiophenyl, benzoxazolyl, carbazolyl, carbolinyl, chromanyl, cinnolinyl, furanyl, imidazolyl, indolinyl, indolyl, indolazinyl, indazolyl, isobenzofuryl, isochromanyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridinyl, pyrimidyl, pyrrolyl, quinazolinyl, quinolyl, quinoxalinyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuryl, dihydrobenzothiophenyl, dihydrobenzoxazolyl, dihydrofuryl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, tetrahydroquinolinyl, tetrahydroisoquinolinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuryl, tetrahydrothienyl, tetrahydroquinolinyl, 2,3-dihydrobenzofuryl, 2,3-dihydrobenzo-1,4-dioxinyl, imidazo(2,1-b)(1,3)thiazole, and benzo-1,3-dioxolyl.

In a variant of this embodiment, the heterocyclyl moiety in A includes azabenzimidazolyl, benzoimidazolyl, benzofuryl, benzopyrazolyl, benzotriazolyl, benzothiophenyl, benzothiazolyl, benzothienyl, benzoxazolyl, carbazolyl, carbolinyl, furanyl, imidazolyl, indolinyl, indolyl, indolazinyl, indazolyl, isobenzofuryl, isoindolyl, isoquinolyl, isothiazolyl, isoxazolyl, naphthpyridinyl, oxadiazolyl, oxazolyl, oxazolinyl, isoxazolinyl, oxetanyl, pyranyl, pyrazinyl, pyrazolyl, pyridazinyl, pyridazinyl, pyridinyl, pyrimidyl, pyrrolyl, quinazolinyl, quinolyl, tetrahydropyranyl, tetrazolyl, thiadiazolyl, thiazolyl, thienyl, triazolyl, azetidinyl, piperazinyl, piperidinyl, pyrrolidinyl, morpholinyl, thiomorpholinyl, dihydrobenzoimidazolyl, methylenedioxybenzyl, tetrahydrofuryl, tetrahydrothienyl, tetrahydroquinolinyl, pyrimidinylphenyl, and pyridinylphenyl, wherein A is optionally substituted with one or more $R^9$ substituents.

In another embodiment, A is selected from: pyridazinyl, pyrimidyl, pyrrolyl, thiazolyl, triazolyl, oxadiazolyl, benzothiazolyl, oxazolyl, quinolyl, benzothienyl, pyrazolyl, pyrazinyl, and pyridinyl, wherein A is optionally substituted with one or more $R^9$ substituents. In a variant of this embodiment, A is selected from: pyrazinyl, pyrazolyl, pyridazinyl, pyridinyl, pyrimidyl, pyrrolyl, thiazolyl, and triazolyl, wherein A is optionally substituted with one or more $R^9$ substituents.

In one embodiment of the invention, $R^1$, in the compounds of formulae I, II, and III, is selected from —$C_{1-10}$ alkyl, —$C_{0-10}$ alkyl-$C_{3-10}$ cycloalkyl, $C_{0-10}$ alkylaryl, —$C_{0-10}$ alkylheterocyclyl; —$NR^bR^c$, and —$C_{0-10}$ alkyl $C_{3-10}$ heterocycloalkyl, wherein $R^1$ is optionally substituted with one or more $R^8$ substituents, and optionally two $R^8$ may join together to form a 3 to 8 member ring.

In one embodiment of the invention, $R^1$, in the compounds of formulae I, II, and III, is selected from —$C_{1-10}$ alkyl, $C_{0-10}$ alkylaryl, —$C_{0-10}$ alkylheterocyclyl; and —$C_{0-10}$ alkyl $C_{3-10}$ heterocycloalkyl, wherein $R^1$ is optionally substituted with one or more $R^8$ substituents, optionally two $R^8$ may join together to form a 3 to 8 member ring.

In one embodiment, $R^1$ in the compounds of formulae I, II, and III, is selected from —$C_{0-10}$ alkylphenyl, —$C_{1-10}$ alkylbiphenyl, $C_{1-10}$ alkyl, —($C_{0-10}$ alkyl)1,3-benzothiazolyl, —($C_{0-10}$ alkyl)napthyl, —($C_{0-10}$ alkyl)2,3-dihydro-1H-indenyl, —($C_{0-10}$ alkyl)pyridinyl, —($C_{0-10}$ alkyl)pyrazinyl, —($C_{0-10}$ alkyl)cyclopropyl, —($C_{0-10}$ alkyl)1,3-benzothiazolyl, —($C_{0-10}$ alkyl)benzofuranyl, —($C_{0-10}$ alkyl)fluorenyl, —($C_{0-10}$ alkyl)thiazolyl, —($C_{0-10}$ alkyl)(2,3,-dihydro-1,4-benzodioxinyl), —($C_{0-10}$ alkyl) $C_{3-10}$ cycloalkyl, —$C_{0-10}$ alkyl(2,3,-dihydrobenzofuranyl), —($C_{0-10}$ alkyl)quinolinyl, benzylamino, aminobenzyl, aminopiperidinyl, piperidinylamino, —($C_{0-10}$ alkyl)cyclohexyl, oxoisoxazolidinyl, diphenylamino, —($C_{0-10}$ alkyl)(3S,5S,7S)-1adamantyl), —($C_{0-10}$ alkyl)pyridinylphenyl, and phenylpyridinyl($C_{0-10}$ alkyl).

In one embodiment, $R^2$ in the compounds of formulae I, II, and III, is selected from hydrogen, —$C_{1-10}$ alkyl, aryl, and heterocyclyl, wherein $C_{1-10}$ alkyl, aryl, and heterocyclyl are unsubstituted or substituted with one or more substituents selected from halo, hydroxyl, $C_{1-10}$ alkyl, and —$OC_{1-10}$ alkyl.

In one embodiment, $R^2$ in the compounds of formulae I, II, and III, is selected from —$C_{0-10}$ alkylphenyl, —$C_{1-10}$ alkylbiphenyl, diphenylmethyl, $C_{1-10}$ alkyl, —($C_{0-10}$ alkyl)1,3-benzothiazolyl, —($C_{0-10}$ alkyl)napthyl, —($C_{0-10}$ alkyl)2,3-dihydro-1H-indenyl, —($C_{0-10}$ alkyl)pyridinyl, —($C_{0-10}$ alkyl)pyrazinyl, —($C_{0-10}$ alkyl)cyclopropyl, —($C_{0-10}$ alkyl) 1,3-benzothiazolyl, benzylamino, aminobenzyl, aminopiperidinyl, piperidinylamino, —($C_{0-10}$ alkyl)cyclohexyl, oxoisoxazolidinyl, diphenylamino, —($C_{0-10}$ alkyl)(3S,5S, 7S)-adamantyl), —($C_{0-10}$ alkyl)pyridinylphenyl, and phenylpyridinyl($C_{0-10}$ alkyl).

In a variant of this embodiment, $R^2$ is selected from hydrogen, —$C_{1-10}$ alkyl, and aryl, wherein $C_{1-10}$ alkyl, and aryl, and are unsubstituted or substituted with one or more substituents selected from halo, hydroxyl, $C_{1-10}$ alkyl, and —$OC_{1-10}$ alkyl. In a variant of this embodiment, $R^2$ is hydrogen.

In one embodiment of the invention, $R^3$, in the compounds of formulae I, II, and III, is selected from hydrogen, halogen, hydroxy, —$C_{1-6}$ alkyl, —$C_{1-6}$ alkoxy, heterocyclyl, —$NR^bR^c$, and —$SC_{0-6}$ alkyl, wherein $R^3$ is optionally substituted by one or more substituents $R^{10}$.

In one variant of this embodiment, $R^3$ is selected from hydroxy, —$C_{1-6}$ alkoxy, —$NR^bR^c$, and —$SC_{0-6}$ alkyl, wherein $R^3$ is optionally substituted by one or more substituents $R^{10}$. In yet another embodiment of this invention, $R^3$ is selected from hydroxy and —$C_{1-6}$ alkoxy optionally substituted by one or more substituents $R^{10}$. In yet another embodiment, $R^3$ is hydroxy.

In one embodiment of the invention, $R^4$, in the compounds of formulae I, II, and III, is selected from hydrogen, —$C_1$-$C_{10}$ alkyl, —$C_2$-$C_{3-10}$ cycloalkyl, $C_{3-10}$ heterocycloalkyl, —($C_{0-10}$ alkyl)aryl, ($C_{0-10}$ alkyl)heterocyclyl, and —$NR^bR^c$, wherein $R^4$ is optionally substituted by one or more substituents $R^9$.

In one embodiment of the invention, $R^4$ is selected from hydrogen, —$C_1$-$C_{10}$ alkyl, —$C_2$-$C_{3-10}$ cycloalkyl, $C_{3-10}$ heterocycloalkyl, —($C_{0-10}$ alkyl)aryl, ($C_{0-10}$ alkyl)heterocyclyl, and —$NR^bR^c$, wherein $R^4$ is optionally substituted by one or more substituents $R^9$.

In another embodiment of the invention, $R^4$ is selected from hydrogen, —$C_1$-$C_{10}$ alkyl, —($C_{0-10}$ alkyl)aryl, ($C_{0-10}$ alkyl)heterocyclyl, and —$NR^bR^c$, wherein $R^4$ is optionally substituted by one or more substituents $R^9$. In a variant of this embodiment, $R^4$ is selected from hydrogen.

In one embodiment of the invention, $R^8$ is selected from halogen, hydroxyl, —$C_{1-10}$ alkyl, —$C_{1-10}$ alkenyl, —$C_{1-10}$ alkynyl, —$OC_{1-10}$ alkylaryl, aryl, heterocyclyl, —$C_{3-10}$ cycloalkyl, —$C_{3-10}$ heterocycloalkyl, cyano, oxo, —$OC_{1-10}$ alkyl, $C_{1-10}$ alkylaminocarbonyl, —(C=O)N($C_{0-6}$ alkyl)$_2$, difluoromethoxy, trifluoromethoxy, trifluoroethoxy, —$SR^a$, and $NR^bR^c$, wherein said alkyl, alkenyl, alkynyl, aryl, heterocyclyl, cycloalkyl, heterocycloalkyl may optionally be substituted with one or more groups selected from hydroxyl, —$CO_2H$, halogen, —$OC_{1-10}$ alkyl, and $C_{1-6}$ alkyl.

In another embodiment, $R^8$ is chosen from: hydrogen, hydroxyl, —$C_{1-10}$ alkyl, aryl, heterocyclyl, $C_{2-6}$ alkylaminocarbonylamino, $C_{0-10}$ alkyloxycarbonylamino$C_{0-6}$ alkyl, $C_{0-10}$ alkylcarbonylamino$C_{0-6}$ alkyl, $C_{2-6}$ alkylaminosulfonylamino$C_{0-4}$ alkyl, —$C_{2-6}$ alkylsulfonylamino$C_{0-4}$ alkyl, —$C_{1-4}$ alkylsulfonyl, arylsulfonyl, —$C_{1-10}$ alkylaminosulfonyl, wherein said alkyl, aryl, heterocyclyl, may optionally be substituted with one or more groups selected from hydroxyl, —$CO_2H$, halogen, —$OC_{1-10}$ alkyl, and $C_{1-6}$ alkyl.

In one embodiment of the compounds of the invention include:

N-[bis(4-methoxyphenyl)methyl]-4-hydroxy-2-pyridazin-3-ylpyrimidine-5-carboxamide;

N-[bis(4-methoxyphenyl)methyl]-4-hydroxy-2-pyridazin-3-ylpyrimidine-5-carboxamide 1,3-dihydroxy-2-(hydroxymethyl)propan-2-ammonium;

N-[bis(4-methoxyphenyl)methyl]-4-hydroxy-2-pyridazin-3-ylpyrimidine-5-carboxamide potassium;

N-[bis(4-hydroxyphenyl)methyl]-4-hydroxy-2-pyridazin-3-ylpyrimidine-5-carboxamide;

4-Hydroxy-N-(1-methyl-1-phenylethyl)-2-(1H-pyrazol-1-yl)pyrimidine-5-carboxamide;

N-[(1S)-1-(4-bromophenyl)ethyl]-4-hydroxy-2-pyridazin-3-ylpyrimidine-5-carboxamide;

4-Hydroxy-N-[(1S)-1-phenylethyl]-2-(1H-pyrazol-1-yl)pyrimidine-5-carboxamide;

N-(1,3-benzothiazol-2-ylmethyl)-4-hydroxy-2-(1H-pyrazol-1-yl)pyrimidine-5-carboxamide;

N-[(1S)-1-(4-fluorophenyl)ethyl]-4-hydroxy-2-(1H-pyrazol-1-yl)pyrimidine-5-carboxamide;

N-[1-(4-fluorophenyl)-1-methylethyl]-4-hydroxy-2-(1H-pyrazol-1-yl)pyrimidine-5-carboxamide;

4-Hydroxy-N-{1-methyl-1-[6-(trifluoromethyl)pyridin-3-yl]ethyl}-2-(1H-pyrazol-1-yl)pyrimidine-5-carboxamide;

4-Hydroxy-N-(1-phenylcyclopropyl)-2-(1H-pyrazol-1-yl)pyrimidine-5-carboxamide;

N-[(1S)-1-(4-cyanophenyl)ethyl]-4-hydroxy-2-(1H-pyrazol-1-yl)pyrimidine-5-carboxamide;

4-Hydroxy-N-[(4-methoxyphenyl)(6-methylpyridin-3-yl)methyl]-2-pyridazin-3-ylpyrimidine-5-carboxamide;

4-Hydroxy-N-[(S)-(4-methoxyphenyl)(6-methylpyridin-3-yl)methyl]-2-pyridazin-3-ylpyrimidine-5-carboxamide;

4-Hydroxy-N-[(R)-(4-methoxyphenyl)(6-methylpyridin-3-yl)methyl]- 2-pyridazin-3-ylpyrimidine-5-carboxamide;

N-[(2,4-Dimethoxyphenyl)(6-methylpyridin-2-yl)methyl]-4-hydroxy-2-pyridazin-3-ylpyrimidine-5-carboxamide;

4-hydroxy-N-[(1S)-1-(4-methoxyphenyl)ethyl]-2-(1H-pyrazol-1-yl)pyrimidine-5-carboxamide;

4-hydroxy-N-[(4-methoxyphenyl)(4-methyl-1,3-thiazol-2-yl)methyl]-2-(pyridazin-3-yl)pyrimidine-5-carboxamide;

4-hydroxy-N-[(S)-(4-methoxyphenyl)(4-methyl-1,3-thiazol-2-yl)methyl]-2-(pyridazin-3-yl)pyrimidine-5-carboxamide;

4-hydroxy-N-[(R)-(4-methoxyphenyl)(4-methyl-1,3-thiazol-2-yl)methyl]-2-(pyridazin-3-yl)pyrimidine-5-carboxamide;

4-hydroxy-N-[(4-methoxyphenyl)(6-methylpyridin-3-yl)methyl]-2-(pyridazin-3-yl)pyrimidine-5-carboxamide;

4-hydroxy-N-[(S)-(4-methoxyphenyl)(6-methylpyridin-3-yl)methyl]-2-(pyridazin-3-yl)pyrimidine-5-carboxamide;

4-hydroxy-N-[(R)-(4-methoxyphenyl)(6-methylpyridin-3-yl)methyl]-2-(pyridazin-3-yl)pyrimidine-5-carboxamide;

N-[(3-cyanophenyl)(4-methoxyphenyl)methyl]-4-hydroxy-2-(pyridazin-3-yl)pyrimidine-5-carboxamide;

N-[(S)-(3-cyanophenyl)(4-methoxyphenyl)methyl]-4-hydroxy-2-(pyridazin-3-yl)pyrimidine-5-carboxamide;

N-[(R)-(3-cyanophenyl)(4-methoxyphenyl)methyl]-4-hydroxy-2-(pyridazin-3-yl)pyrimidine-5-carboxamide;

N-[(4-cyanophenyl)(4-methoxyphenyl)methyl]-4-hydroxy-2-(pyridazin-3-yl)pyrimidine-5-carboxamide;

N-[(S)-(4-cyanophenyl)(4-methoxyphenyl)methyl]-4-hydroxy-2-(pyridazin-3-yl)pyrimidine-5-carboxamide;

N-[(R)-(4-cyanophenyl)(4-methoxyphenyl)methyl]-4-hydroxy-2-(pyridazin-3-yl)pyrimidine-5-carboxamide;

N-[(4-cyanophenyl)(2,4-dimethoxyphenyl)methyl]-4-hydroxy-2-(pyridazin-3-yl)pyrimidine-5-carboxamide;

N-[(S)-(4-cyanophenyl)(2,4-dimethoxyphenyl)methyl]-4-hydroxy-2-(pyridazin-3-yl)pyrimidine-5-carboxamide;

N-[(R)-(4-cyanophenyl)(2,4-dimethoxyphenyl)methyl]-4-hydroxy-2-(pyridazin-3-yl)pyrimidine-5-carboxamide;

4-hydroxy-N-[(4-hydroxyphenyl)(4-methoxyphenyl)methyl]-2-(pyridazin-3-yl)pyrimidine-5-carboxamide;

4-hydroxy-N-[(5)-(4-hydroxyphenyl)(4-methoxyphenyl)methyl]-2-(pyridazin-3-yl)pyrimidine-5-carboxamide;

4-hydroxy-N-[(R)-(4-hydroxyphenyl)(4-methoxyphenyl)methyl]-2-(pyridazin-3-yl)pyrimidine-5-carboxamide;

N-[1-(4-cyanophenyl)-3-methylbutyl]-4-hydroxy-2-(pyridazin-3-yl)pyrimidine-5-carboxamide;

N-[(4-cyanophenyl)(cyclohexyl)methyl]-4-hydroxy-2-(pyridazin-3-yl)pyrimidine-5-carboxamide;

N-[(S)-(4-cyanophenyl)(cyclohexyl)methyl]-4-hydroxy-2-(pyridazin-3-yl)pyrimidine-5-carboxamide;

N-[(R)-(4-cyanophenyl)(cyclohexyl)methyl]-4-hydroxy-2-(pyridazin-3-yl)pyrimidine-5-carboxamide;

N-[2,3-dihydro-1-benzofuran-5-yl(4-methoxyphenyl)methyl]-4-hydroxy-2-(pyridazin-3-yl)pyrimidine-5-carboxamide;

4-hydroxy-N-[(4-methoxyphenyl)(6-methoxypyridin-3-yl)methyl]-2-(pyridazin-3-yl)pyrimidine-5-carboxamide;

4-hydroxy-N-[(S)-(4-methoxyphenyl)(6-methoxypyridin-3-yl)methyl]-2-(pyridazin-3-yl)pyrimidine-5-carboxamide;

4-hydroxy-N-[(R)-(4-methoxyphenyl)(6-methoxypyridin-3-yl)methyl]-2-(pyridazin-3-yl)pyrimidine-5-carboxamide;

N-[1,3-benzothiazol-2-yl(4-methoxyphenyl)methyl]-4-hydroxy-2-(pyridazin-3-yl)pyrimidine-5-carboxamide;

4-Hydroxy-N-[[4-(methoxymethyl)phenyl](4-methoxyphenyl)methyl]-2-pyridazin-3-ylpyrimidine-5-carboxamide;

4-Hydroxy-N-[[(S)-4-(methoxymethyl)phenyl](4-methoxyphenyl)methyl]-2-pyridazin-3-ylpyrimidine-5-carboxamide;

4-Hydroxy-N-[[(R)-4-(methoxymethyl)phenyl](4-methoxyphenyl)methyl]-2-pyridazin-3-ylpyrimidine-5-carboxamide;

N-{bis[4-(methoxymethyl)phenyl]methyl}-4-hydroxy-2-pyridazin-3-ylpyrimidine-5-carboxamide;

N-[bis(6-methoxypyridin-3-yl)methyl]-4-hydroxy-2-(pyridazin-3-yl)pyrimidine-5-carboxamide;

N-[bis(4-methoxyphenyl)methyl]-4-hydroxy-2-pyridin-2-ylpyrimidine-5-carboxamide;

N-(diphenylmethyl)-4-hydroxy-2-pyridazin-3-ylpyrimidine-5-carboxamide;

4-hydroxy-N-(1-phenylcyclohexyl)-2-pyridazin-3-ylpyrimidine-5-carboxamide;

N-(biphenyl-4-ylmethyl)-4-hydroxy-2-pyridazin-3-ylpyrimidine-5-carboxamide;

N- [2-(4-fluorophenyl)ethyl]-4-hydroxy-2-(2-methyl-1,3-thiazol-4-yl)pyrimidine-5-carboxamide;

4-Hydroxy-N-[(1S)-1-phenylpropyl]-2-(1H-pyrazol-1-yl)pyrimidine-5-carboxamide;

N-(biphenyl-4-ylmethyl)-4-hydroxy-2-(1H-pyrazol-1-yl)pyrimidine-5-carboxamide;

N-(diphenylmethyl)-4-hydroxy-2-(1H-pyrazol-1-yl)pyrimidine-5-carboxamide;

N-[(6-chloropyridin-3-yl)methyl]-4-hydroxy-2-(1H-pyrazol-1-ylpyrimidine-5-carboxamide;

N-(4-chlorobenzyl)-4-hydroxy-2-(2H-pyrazol-1-yl)pyrimidine-5-carboxamide;

N'-Ethyl-4-hydroxy-N'-phenyl-2-(1H-pyrazol-1-yl)pyrimidine-5-carbohydrazide trifluoroacetate;

4-Hydroxy-N-[(1S)-1-(4-methylphenyl)ethyl]-2-(1H-pyrazol-1-yl)pyrimidine-5-carboxamide;

N-[(1S)-1-(4-bromophenyl)ethyl]-4-hydroxy-2-(1H-pyrazol-1-yl)pyrimidine-5-carboxamide;

N-[1-(4-bromophenyl)-1-methylethyl]-4-hydroxy-2-(1H-pyrazol-1-yl)pyrimidine-5-carboxamide;

N-(4-benzoylbenzyl)-4-hydroxy-2-(1H-pyrazol-1-yl)pyrimidine-5-carboxamide;

N-[bis(4-methoxyphenyl)methyl]-4-hydroxy-2-(1H-pyrazol-1-yl)pyrimidine-5-carboxamide;

4-hydroxy-N-[(1R,2S)-2-hydroxy-1,2-diphenylethyl]-2-(1H-pyrazol-1-yl)pyrimidine-5-carboxamide;

4-hydroxy-N-[(1R)-2-hydroxy-1-phenylethyl]-2-(1H-pyrazol-1-yl)pyrimidine-5-carboxamide;

4-hydroxy-N-[phenyl(pyridin-2-yl)methyl]-2-(1H-pyrazol-1-yl)pyrimidine-5-carboxamide trifluoroacetate;

4-hydroxy-N-[(1S)-1-(3-methoxyphenyl)ethyl]-2-(1H-pyrazol-1-yl)pyrimidine-5-carboxamide;

4-hydroxy-N-[(1R,2R)-2-hydroxy-1,2-diphenylethyl]-2-(1H-pyrazol-1-yl)pyrimidine-5-carboxamide;

4-hydroxy-N-[(1R)-2-hydroxy-2-methyl-1-phenylpropyl]-2-(1H-pyrazol-1-yl)pyrimidine-5-carboxamide;

4-hydroxy-N-[(1S)-1-(4-phenoxyphenyl)ethyl]-2-(1H-pyrazol-1-yl)pyrimidine-5-carboxamide;

4-hydroxy-N-(2-methyl-1-phenylpropyl)-2-(1H-pyrazol-1-yl)pyrimidine-5-carboxamide;

N-[(1S)-1-(2,3-dihydro-1,4-benzodioxin-6-yl)ethyl]-4-hydroxy-2-(1H-pyrazol-1-yl)pyrimidine-5-carboxamide;

4-hydroxy-2-(4-methyl-1H-pyrazol-1-yl)-N-[(1S)-1-phenylpropyl]pyrimidine-5-carboxamide;
4-hydroxy-N-[(1S)-1-(4-methoxyphenyl)ethyl]-2-(4-methyl-1H-pyrazol-1-yl)pyrimidine-5-carboxamide;
4-hydroxy-N-[phenyl(pyridin-2-yl)methyl]-2-pyridazin-3-ylpyrimidine-5-carboxamide trifluoroacetate;
4-hydroxy-N-[(1S)-1-(4-phenoxyphenyl)ethyl]-2-(pyridazin-3-yl)pyrimidine-5-carboxamide;
4-hydroxy-N-[(1R,2S)-2-hydroxy-1,2-diphenylethyl]-2-(pyridazin-3-yl)pyrimidine-5-carboxamide;
4-hydroxy-N-[(1R,2R)-2-hydroxy-1,2-diphenylethyl]-2-(pyridazin-3-yl)pyrimidine-5-carboxamide;
N-[(1S)-1-(2,3-dihydro-1,4-benzodioxin-6-yl)ethyl]-4-hydroxy-2-(pyridazin-3-yl)pyrimidine-5-carboxamide;
4-hydroxy-2-(1H-pyrazol-1-yl)-N-{(1S)-1-[6-(trifluoromethyl)pyridin-3-yl]ethyl}pyrimidine-5-carboxamide;
4-hydroxy-2-(1H-pyrazol-1-yl)-N-{(1R)-1-[6-(trifluoromethyl)pyridin-3-yl]ethyl}pyrimidine-5-carboxamide;
4-hydroxy-N-{phenyl[6-(trifluoromethyl)pyridin-3-yl]methyl}-2-(1H-pyrazol-1-yl)pyrimidine-5-carboxamide;
4-hydroxy-N-{(S)-phenyl[6-(trifluoromethyl)pyridin-3-yl]methyl}-2-(1H-pyrazol-1-yl)pyrimidine-5-carboxamide;
4-hydroxy-N-{(N)phenyl[6-(trifluoromethyl)pyridin-3-yl]methyl}-2-(1H-pyrazol-1-yl)pyrimidine-5-carboxamide;
N-[(2,4-dimethoxyphenyl)(6-methylpyridin-2-yl)methyl]-4-hydroxy-2-(pyridazin-3-yl)pyrimidine-5-carboxamide;
4-hydroxy-N-[(4-methoxyphenyl)(pyrazin-2-yl)methyl]-2-(1H-pyrazol-1-yl)pyrimidine-5-carboxamide;
4-hydroxy-N-[(4-methoxyphenyl)(quinolin-2-yl)methyl]-2-(pyridazin-3-yl)pyrimidine-5-carboxamide;
and pharmaceutically acceptable salts and solvates thereof.

In another embodiment of the compounds of the invention include:

N-[bis(4-methoxyphenyl)methyl]-4-hydroxy-2-pyridazin-3-ylpyrimidine-5-carboxamide;
N-[bis(4-methoxyphenyl)methyl]-4-hydroxy-2-pyridazin-3-ylpyrimidine-5-carboxamide 1,3-dihydroxy-2-(hydroxymethyl)propan-2-ammonium;
N-[bis(4-methoxyphenyl)methyl]-4-hydroxy-2-pyridazin-3-ylpyrimidine-5-carboxamide potassium;
N-[bis(4-hydroxyphenyl)methyl]-4-hydroxy-2-pyridazin-3-ylpyrimidine-5-carboxamide;
4-Hydroxy-N-(1-methyl-1-phenylethyl)-2-(1H-pyrazol-1-yl)pyrimidine-5-carboxamide;
N-[(1S)-1-(4-bromophenyl)ethyl]-4-hydroxy-2-pyridazin-3-ylpyrimidine-5-carboxamide;
4-Hydroxy-N-[(1S)-1-phenylethyl]-2-(1H-pyrazol-1-yl)pyrimidine-5-carboxamide;
N-(1,3-benzothiazol-2-ylmethyl)-4-hydroxy-2-(1H-pyrazol-1-yl)pyrimidine-5-carboxamide;
N-[(1S)-1-(4-fluorophenyl)ethyl]-4-hydroxy-2-(1H-pyrazol-1-yl)pyrimidine-5-carboxamide;
N-[1-(4-fluorophenyl)-1-methylethyl]-4-hydroxy-2-(1H-pyrazol-1-yl)pyrimidine-5-carboxamide;
4-Hydroxy-N-{1-methyl-1-[6-(trifluoromethyl)pyridin-3-yl]ethyl}-2-(1H-pyrazol-1-yl)pyrimidine-5-carboxamide;
4-Hydroxy-N-(1-phenylcyclopropyl)-2-(1H-pyrazol-1-yl)pyrimidine-5-carboxamide;
N-[(1S)-1-(4-cyanophenyl)ethyl]-4-hydroxy-2-(1H-pyrazol-1-yl)pyrimidine-5-carboxamide;
4-Hydroxy-N-[(4-methoxyphenyl)(6-methylpyridin-3-yl)methyl]-2-pyridazin-3-ylpyrimidine-5-carboxamide;
N-[(2,4-Dimethoxyphenyl)(6-methylpyridin-2-yl)methyl]-4-hydroxy-2-pyridazin-3-ylpyrimidine-5-carboxamide;
4-hydroxy-N-[(1S)-1-(4-methoxyphenyl)ethyl]-2-(1H-pyrazol-1-yl)pyrimidine-5-carboxamide;
4-hydroxy-N-[(4-methoxyphenyl)(4-methyl-1,3-thiazol-2-yl)methyl]-2-(pyridazin-3-yl)pyrimidine-5-carboxamide;
4-hydroxy-N-[(S)-(4-methoxyphenyl)(4-methyl-1,3-thiazol-2-yl)methyl]-2-(pyridazin-3-yl)pyrimidine-5-carboxamide;
4-hydroxy-N-[(R)-(4-methoxyphenyl)(4-methyl-1,3-thiazol-2-yl)methyl]-2-(pyridazin-3-yl)pyrimidine-5-carboxamide;
4-hydroxy-N-[(4-methoxyphenyl)(6-methylpyridin-3-yl)methyl]-2-(pyridazin-3-yl)pyrimidine-5-carboxamide;
4-hydroxy-N-[(S)-(4-methoxyphenyl)(6-methylpyridin-3-yl)methyl]-2-(pyridazin-3-yl)pyrimidine-5-carboxamide;
4-hydroxy-N-[(R)-(4-methoxyphenyl)(6-methylpyridin-3-yl)methyl]-2-(pyridazin-3-yl)pyrimidine-5-carboxamide;
N-[(3-cyanophenyl)(4-methoxyphenyl)methyl]-4-hydroxy-2-(pyridazin-3-yl)pyrimidine-5-carboxamide;
N-[(S)-(3-cyanophenyl)(4-methoxyphenyl)methyl]-4-hydroxy-2-(pyridazin-3-yl)pyrimidine-5-carboxamide;
N-[(R)-(3-cyanophenyl)(4-methoxyphenyl)methyl]-4-hydroxy-2-(pyridazin-3-yl)pyrimidine-5-carboxamide;
N-[(4-cyanophenyl)(4-methoxyphenyl)methyl]-4-hydroxy-2-(pyridazin-3-yl)pyrimidine-5-carboxamide;
N-[(S)-(4-cyanophenyl)(4-methoxyphenyl)methyl]-4-hydroxy-2-(pyridazin-3-yl)pyrimidine-5-carboxamide;
N-[(R)-(4-cyanophenyl)(4-methoxyphenyl)methyl]-4-hydroxy-2-(pyridazin-3-yl)pyrimidine-5-carboxamide;
N-[(4-cyanophenyl)(2,4-dimethoxyphenyl)methyl]-4-hydroxy-2-(pyridazin-3-yl)pyrimidine-5-carboxamide;
N-[(S)-(4-cyanophenyl)(2,4-dimethoxyphenyl)methyl]-4-hydroxy-2- (pyridazin-3-yl)pyrimidine-5-carboxamide;
N-[(R)-(4-cyanophenyl)(2,4-dimethoxyphenyl)methyl]-4-hydroxy-2-(pyridazin-3-yl)pyrimidine-5-carboxamide;
4-hydroxy-N-[(4-hydroxyphenyl)(4-methoxyphenyl)methyl]-2-(pyridazin-3-yl)pyrimidine-5-carboxamide;
4-hydroxy-N-[(S)-(4-hydroxyphenyl)(4-methoxyphenyl)methyl]-2-(pyridazin-3-yl)pyrimidine-5-carboxamide;
4-hydroxy-N-[(R)-(4-hydroxyphenyl)(4-methoxyphenyl)methyl]-2-(pyridazin-3-yl)pyrimidine-5-carboxamide;
N-[1-(4-cyanophenyl)-3-methylbutyl]-4-hydroxy-2-(pyridazin-3-yl)pyrimidine-5-carboxamide;
N-[(S)-1-(4-cyanophenyl)-3-methylbutyl]-4-hydroxy-2-(pyridazin-3-yl)pyrimidine-5-carboxamide;
N-[(R)-1-(4-cyanophenyl)-3-methylbutyl]-4-hydroxy-2-(pyridazin-3-yl)pyrimidine-5-carboxamide;
N-[(4-cyanophenyl)(cyclohexyl)methyl]-4-hydroxy-2-(pyridazin-3-yl)pyrimidine-5-carboxamide;
N-[(S)-(4-cyanophenyl)(cyclohexyl)methyl]-4-hydroxy-2-(pyridazin-3-yl)pyrimidine-5-carboxamide;
N-[(R)-(4-cyanophenyl)(cyclohexyl)methyl]-4-hydroxy-2-(pyridazin-3-yl)pyrimidine-5-carboxamide;
N-[2,3-dihydro-1-benzofuran-5-yl(4-methoxyphenyl)methyl]-4-hydroxy-2-(pyridazin-3-yl)pyrimidine-5-carboxamide;
4-hydroxy-N-[(4-methoxyphenyl)(6-methoxypyridin-3-yl)methyl]-2-(pyridazin-3-yl)pyrimidine-5-carboxamide;
4-hydroxy-N-[(S)-(4-methoxyphenyl)(6-methoxypyridin-3-yl)methyl]-2-(pyridazin-3-yl)pyrimidine-5-carboxamide;
4-hydroxy-N-[(R)-(4-methoxyphenyl)(6-methoxypyridin-3-yl)methyl]-2-(pyridazin-3-yl)pyrimidine-5-carboxamide;
N-[1,3-benzothiazol-2-yl(4-methoxyphenyl)methyl]-4-hydroxy-2-(pyridazin-3-yl)pyrimidine-5-carboxamide;
4-Hydroxy-N-[[4-(methoxymethyl)phenyl](4-methoxyphenyl)methyl]-2-pyridazin-3-ylpyrimidine-5-carboxamide;
4-Hydroxy-N-[[(S)-4-(methoxymethyl)phenyl](4-methoxyphenyl)methyl]-2-pyridazin-3-ylpyrimidine-5-carboxamide;

4-Hydroxy-N-[[(R)-4-(methoxymethyl)phenyl](4-methoxyphenyl)methyl]-2-pyridazin-3-ylpyrimidine-5-carboxamide;
N-{bis[4-(methoxymethyl)phenyl]methyl]}-4-hydroxy-2-pyridazin-3-ylpyrimidine-5-carboxamide;
N-[bis(6-methoxypyridin-3-yl)methyl]-4-hydroxy-2-(pyridazin-3-yl)pyrimidine-5-carboxamide;
and pharmaceutically acceptable salts and solvates thereof.
In another embodiment of the invention,
N-[bis(4-methoxyphenyl)methyl]-4-hydroxy-2-pyridin-2-ylpyrimidine-5-carboxamide;
N-(diphenylmethyl)-4-hydroxy-2-pyridazin-3-ylpyrimidine-5-carboxamide;
4-hydroxy-N-(1-phenylcyclohexyl)-2-pyridazin-3-ylpyrimidine-5-carboxamide;
N-(biphenyl-4-ylmethyl)-4-hydroxy-2-pyridazin-3-ylpyrimidine-5-carboxamide;
N-[2-(4-fluorophenyl)ethyl]-4-hydroxy-2-(2-methyl-1,3-thiazol-4-yl)pyrimidine-5-carboxamide;
4-Hydroxy-N-[(1S)-1-phenylpropyl]-2-(1H-pyrazol-1-yl)pyrimidine-5-carboxamide;
N-(biphenyl-4-ylmethyl)-4-hydroxy-2-(1H-pyrazol-1-yl)pyrimidine-5-carboxamide;
N-(diphenylmethyl)-4-hydroxy-2-(1H-pyrazol-1-yl)pyrimidine-5-carboxamide;
N-[(6-chloropyridin-3-yl)methyl]-4-hydroxy-2-(1H-pyrazol-1-yl)pyrimidine-5-carboxamide;
N-(4-chlorobenzyl)-4-hydroxy-2-(1H-pyrazol-1-yl)pyrimidine-5-carboxamide;
N'-Ethyl-4-hydroxy-N'-phenyl-2-(1H-pyrazol-1-yl)pyrimidine-5-carbohydrazide trifluoroacetate;
4-Hydroxy-N-[(1S)-1-(4-methylphenyl)ethyl]-2-(1H-pyrazol-1-yl)pyrimidine-5-carboxamide;
N-[(1S)-1-(4-bromophenyl)ethyl]-4-hydroxy-2-(1H-pyrazol-1-yl)pyrimidine-5-carboxamide;
N-[1-(4-bromophenyl)-1-methylethyl]-4-hydroxy-2-(1H-pyrazol-1-yl)pyrimidine-5-carboxamide;
N-(4-benzoylbenzyl)-4-hydroxy-2-(1H-pyrazol-1-yl)pyrimidine-5-carboxamide;
N-[bis(4-methoxyphenyl)methyl]-4-hydroxy-2-(1H-pyrazol-1-yl)pyrimidine-5-carboxamide;
4-hydroxy-N-[(1R,2S)-2-hydroxy-1,2-diphenylethyl]-2-(1H-pyrazol-1-yl)pyrimidine-5-carboxamide;
4-hydroxy-N-[(1R)-2-hydroxy-1-phenylethyl]-2-(1H-pyrazol-1-yl)pyrimidine-5-carboxamide;
4-hydroxy-N-[phenyl(pyridin-2-yl)methyl]-2-(1H-pyrazol-1-yl)pyrimidine-5-carboxamide trifluoroacetate;
4-hydroxy-N-[(1S)-1-(3-methoxyphenyl)ethyl]-2-(1H-pyrazol-1-yl)pyrimidine-5-carboxamide;
4-hydroxy-N-[(1R,2R)-2-hydroxy-1,2-diphenylethyl]-2-(1H-pyrazol-1-yl)pyrimidine-5-carboxamide;
4-hydroxy-N-[(1R)-2-hydroxy-2-methyl-1-phenylpropyl]-2-(1H-pyrazol-1-yl)pyrimidine-5-carboxamide;
4-hydroxy-N-[(1S)-1-(4-phenoxyphenyl)ethyl]-2-(1H-pyrazol-1-yl)pyrimidine-5-carboxamide;
4-hydroxy-N-(2-methyl-1-phenylpropyl)-2-(1H-pyrazol-1-yl)pyrimidine-5-carboxamide;
N-[(1S)-1-(2,3-dihydro-1,4-benzodioxin-6-yl)ethyl]-4-hydroxy-2-(1H-pyrazol-1-yl)pyrimidine-5-carboxamide;
4-hydroxy-2-(4-methyl-1H-pyrazol-1-yl)-N-[(1S)-1-phenylpropyl]pyrimidine-5-carboxamide;
4-hydroxy-N-[(1S)-1-(4-methoxyphenyl)ethyl]-2-(4-methyl-1H-pyrazol-1-yl)pyrimidine-5-carboxamide;
4-hydroxy-N-[phenyl(pyridin-2-yl)methyl]-2-pyridazin-3-ylpyrimidine-5-carboxamide trifluoroacetate;
4-hydroxy-N-[(1S)-1-(4-phenoxyphenyl)ethyl]-2-(pyridazin-3-yl)pyrimidine-5-carboxamide;
4-hydroxy-N-[(1R,2S)-2-hydroxy-1,2-diphenylethyl]-2-(pyridazin-3-yl)pyrimidine-5-carboxamide;
4-hydroxy-N-[(1R,2R)-2-hydroxy-1,2-diphenylethyl]-2-(pyridazin-3-yl)pyrimidine-5-carboxamide;
N-[(1S)-1-(2,3-dihydro-1,4-benzodioxin-6-yl)ethyl]-4-hydroxy-2-(pyridazin-3-yl)pyrimidine-5-carboxamide;
4-hydroxy-2-(1H-pyrazol-1-yl)-N-{(1S)-1-[6-(trifluoromethyl)pyridin-3-yl]ethyl}pyrimidine-5-carboxamide;
4-hydroxy-N-{phenyl[6-(trifluoromethyl)pyridin-3-yl]methyl}-2-(1H-pyrazol-1-yl)pyrimidine-5-carboxamide;
N-[(2,4-dimethoxyphenyl)(6-methylpyridin-2-yl)methyl]-4-hydroxy-2-(pyridazin-3-yl)pyrimidine-5-carboxamide;
N-[(S)-(2,4-dimethoxyphenyl)(6-methylpyridin-2-yl)methyl]-4-hydroxy-2-(pyridazin-3-yl)pyrimidine-5-carboxamide;
N-[(R)-(2,4-dimethoxyphenyl)(6-methylpyridin-2-yl)methyl]-4-hydroxy-2-(pyridazin-3-yl)pyrimidine-5-carboxamide;
4-hydroxy-N-[(4-methoxyphenyl)(pyrazin-2-yl)methyl]-2-(1H-pyrazol-1-yl)pyrimidine-5-carboxamide;
4-hydroxy-N-[(4-methoxyphenyl)(quinolin-2-yl)methyl]-2-(pyridazin-3-yl)pyrimidine-5-carboxamide;
and pharmaceutically acceptable salts and solvates thereof.
In one embodiment of the compounds of the invention include:
2-(4-Bromopyridin-2-yl)-4-hydroxy-N-(1-methyl-1-phenylethyl)pyrimidine-5-carboxamide;
2-(4-Hydroxy-5-{[(1-methyl-1-phenylethyl)amino]carbonyl}pyrimidin-2-yl)isonicotinic acid;
6-(5-{[(4-Fluorobenzyl)amino]carbonyl}-4-hydroxypyrimidin-2-yl)nicotinic acid;
4-Hydroxy-N-(1-methyl-1-phenylethyl)-2-pyridazin-3-ylpyrimidine-5-carboxamide;
N-[bis(4-methoxyphenyl)methyl]-4-hydroxy-2-pyridazin-3-ylpyrimidine-5-carboxamide;
N-[bis(4-methoxyphenyl)methyl]-4-hydroxy-2-pyridazin-3-ylpyrimidine-5-carboxamide 1,3-dihydroxy-2-(hydroxymethyl)propan-2-ammonium salt;
N-[bis(4-methoxyphenyl)methyl]-4-hydroxy-2-pyridazin-3-ylpyrimidine-5-carboxamide potassium salt;
N-[bis(4-hydroxyphenyl)methyl]-4-hydroxy-2-pyridazin-3-ylpyrimidine-5-carboxamide;
N-(4-fluorobenzyl)-4-hydroxy-2-pyridin-2-ylpyrimidine-5-carboxamide;
4-Hydroxy-N-(1-methyl-1-phenylethyl)-2-(1H-pyrazol-1-yl)pyrimidine-5-carboxamide;
N-[(1S)-1-(4-bromophenyl)ethyl]-4-hydroxy-2-pyridazin-3-ylpyrimidine-5-carboxamide;
N-(diphenylmethyl)-4-hydroxy-2-pyridazin-3-ylpyrimidine-5-carboxamide;
4-hydroxy-N-(1-phenylcyclohexyl)-2-pyridazin-3-ylpyrimidine-5-carboxamide;
N-(biphenyl-4-ylmethyl)-4-hydroxy-2-pyridazin-3-ylpyrimidine-5-carboxamide;
N-(biphenyl-3-ylmethyl)-4-hydroxy-2-(2-methyl-1,3-thiazol-4-yl)pyrimidine-5-carboxamide;
4-Hydroxy-N-(1-methyl-1-phenylethyl)-2-(1,3-thiazol-4-yl)pyrimidine-5-carboxamide;
2-(3,5-Dimethyl-1H-pyrazol-1-yl)-4-hydroxy-N-[4-(trifluoromethoxy)benzyl]pyrimidine-5-carboxamide;
N-[1-(4-fluorophenyl)ethyl]-4-hydroxy-2-(1H-pyrazol-1-yl)pyrimidine-5-carboxamide;
N-[(1S)-1-(4-fluorophenyl)ethyl]-4-hydroxy-2-(1H-pyrazol-1-yl)pyrimidine-5-carboxamide;
N-[(1R)-1-(4-fluorophenyl)ethyl]-4-hydroxy-2-(1H-pyrazol-1-yl)pyrimidine-5-carboxamide;

N-[1-(4-fluorophenyl)-1-methylethyl]-4-hydroxy-2-(1H-pyrazol-1-yl)pyrimidine-5-carboxamide;
4-Hydroxy-N-{1-methyl-1-[6-(trifluoromethyl)pyridin-3-yl]ethyl}-2-(1H-pyrazol-1-yl)pyrimidine-5-carboxamide;
N-(4-chlorobenzyl)-4-hydroxy-2-(1H-pyrazol-1-yl)pyrimidine-5-carboxamide;
N'-Ethyl-4-hydroxy-N'-phenyl-2-(1H-pyrazol-1-yl)pyrimidine-5-carbohydrazide trifluoroacetate;
4-Hydroxy-N-(4-methylbenzyl)-2-(1H-pyrazol-1-yl)pyrimidine-5-carboxamide;
4-Hydroxy-N-[(1R)-1-(4-methylphenyl)ethyl]-2-(1H-pyrazol-1-yl)pyrimidine-5-carboxamide;
4-Hydroxy-N-[(1S)-1-(4-methylphenyl)ethyl]-2-(1H-pyrazol-1-yl)pyrimidine-5-carboxamide;
4-hydroxy-N-piperidin-1-yl-2-(1H-pyrazol-1-yl)pyrimidine-5-carboxamide trifluoroacetate;
5-(Piperidin-1-ylcarbonyl)-2-(1H-pyrazol-1-yl)pyrimidin-4-ol;
N-(4-tert-butylcyclohexyl)-4-hydroxy-2-(1H-pyrazol-1-yl)pyrimidine-5-carboxamide;
4-Hydroxy-N-[(4R)-3-oxoisoxazolidin-4-yl]-2-(1H-pyrazol-1-yl)pyrimidine-5-carboxamide;
N-[(1R)-1-cyclohexylethyl]-4-hydroxy-2-(1H-pyrazol-1-yl)pyrimidine-5-carboxamide;
N-[(1S)-1-cyclohexylethyl]-4-hydroxy-2-(1H-pyrazol-1-yl)pyrimidine-5-carboxamide;
4-hydroxy-2-(1H-pyrazol-1-yl)-N-(1-pyridin-4-ylethyl)pyrimidine-5-carboxamide trifluoroacetate;
4-Hydroxy-N-(1-phenylcyclopropyl)-2-(1H-pyrazol-1-yl)pyrimidine-5-carboxamide;
4-hydroxy-N',N'-diphenyl-2-(1H-pyrazol-1-yl)pyrimidine-5-carbohydrazide trifluoroacetate;
N-{[6-(4-fluorophenyl)pyridin-3-yl]methyl}4-hydroxy-2-(1H-pyrazol-1-yl)pyrimidine-5-carboxamide;
N-{[5-(4-fluorophenyl)pyrazin-2-yl]methyl}-4-hydroxy-2-(1H-pyrazol-1-yl)pyrimidine-5-carboxamide;
N-[(6-cyanopyridin-3-yl)methyl]-4-hydroxy-2-(1H-pyrazol-1-yl)pyrimidine-5-carboxamide;
1-(4-Hydroxy-5-{[(1-methyl-1-phenylethyl)amino]carbonyl}pyrimidin-2-yl)-1H-pyrazole-4-carboxylic acid;
N-[bis(4-methoxyphenyl)methyl]-4-hydroxy-2-(1H-pyrazol-1-yl)pyrimidine-5-carboxamide;
4-hydroxy-N-[4-(4-methylphenoxy)benzyl]-2-(1H-pyrazol-1-yl)pyrimidine-5-carboxamide;
N-(1-ethyl-1-phenylpropyl)-4-hydroxy-2-(1H-pyrazol-1-yl)pyrimidine-5-carboxamide;
N-(2,3-dihydro-1-benzofuran-5-ylmethyl)-4-hydroxy-2-(1H-pyrazol-1-yl)pyrimidine-5-carboxamide;
N-9H-fluoren-9-yl-4-hydroxy-2-(1H-pyrazol-1-yl)pyrimidine-5-carboxamide;
methyl 4-[({[4-hydroxy-2-(1H-pyrazol-1-yl)pyrimidin-5-yl]carbonyl}amino)methyl]benzoate;
and pharmaceutically acceptable salts and solvates thereof.

In another embodiment of the invention, compounds include:
2-(4-Bromopyridin-2-yl)-4-hydroxy-N-(1-methyl-1-phenylethyl)pyrimidine-5-carboxamide;
2-(4-Hydroxy-5-{[(1-methyl-1-phenylethyl)amino]carbonyl}pyrimidin-2-yl)isonicotinic acid;
6-(5-{[(4-Fluorobenzyl)amino]carbonyl}-4-hydroxypyrimidin-2-yl)nicotinic acid;
4-Hydroxy-N-(1-methyl-1-phenylethyl)-2-pyridazin-3-ylpyrimidine-5-carboxamide;
N-[bis(4-methoxyphenyl)methyl]-4-hydroxy-2-pyridazin-3-ylpyrimidine-5-carboxamide;
N-[bis(4-methoxyphenyl)methyl]-4-hydroxy-2-pyridazin-3-ylpyrimidine-5-carboxamide 1,3-dihydroxy-2-(hydroxymethyl)propan-2-ammonium salt;
N-[bis(4-methoxyphenyl)methyl]-4-hydroxy-2-pyridazin-3-ylpyrimidine-5-carboxamide potassium salt;
N-[bis(4-hydroxyphenyl)methyl]-4-hydroxy-2-pyridazin-3-ylpyrimidine-5-carboxamide;
N-(4-fluorobenzyl)-4-hydroxy-2-pyridin-2-ylpyrimidine-5-carboxamide;
4-Hydroxy-N-(1-methyl-1-phenylethyl)-2-(1H-pyrazol-1-yl)pyrimidine-5-carboxamide;
N-[(1S)-1-(4-bromophenyl)ethyl]-4-hydroxy-2-pyridazin-3-ylpyrimidine-5-carboxamide;
N-(diphenylmethyl)-4-hydroxy-2-pyridazin-3-ylpyrimidine-5-carboxamide;
4-hydroxy-N-(1-phenylcyclohexyl)-2-pyridazin-3-ylpyrimidine-5-carboxamide;
N-(biphenyl-4-ylmethyl)-4-hydroxy-2-pyridazin-3-ylpyrimidine-5-carboxamide;
N-(biphenyl-3-ylmethyl)-4-hydroxy-2-(2-methyl-1,3-thiazol-4-yl)pyrimidine-5-carboxamide;
4-Hydroxy-N-(1-methyl-1-phenylethyl)-2-(1,3-thiazol-4-yl)pyrimidine-5-carboxamide;
2-(3,5-Dimethyl-1H-pyrazol-1-yl)-4-hydroxy-N-[4-(trifluoromethoxy)benzyl]pyrimidine-5-carboxamide;
N-[1-(4-fluorophenyl)ethyl]-4-hydroxy-2-(1H-pyrazol-1-yl)pyrimidine-5-carboxamide;
N-[(1S)-1-(4-fluorophenyl)ethyl]-4-hydroxy-2-(1H-pyrazol-1-yl)pyrimidine-5-carboxamide;
N-[(1R)-1-(4-fluorophenyl)ethyl]-4-hydroxy-2-(1H-pyrazol-1-yl)pyrimidine-5-carboxamide;
N-[1-(4-fluorophenyl)-1-methylethyl]-4-hydroxy-2-(1H-pyrazol-1-yl)pyrimidine-5-carboxamide;
4-Hydroxy-N-{1-methyl-1-[6-(trifluoromethyl)pyridin-3-yl]ethyl}-2-(1H-pyrazol-1-yl)pyrimidine-5-carboxamide;
and pharmaceutically acceptable salts and solvates thereof.

In yet another embodiment of the invention, compounds include:
2-(4-Bromopyridin-2-yl)-4-hydroxy-N-(1-methyl-1-phenylethyl)pyrimidine-5-carboxamide;
2-(4-Hydroxy-5-{[(1-methyl-1-phenylethyl)amino]carbonyl}pyrimidin-2-yl)isonicotinic acid;
6-(5-{[(4-Fluorobenzyl)amino]carbonyl}-4-hydroxypyrimidin-2-yl)nicotinic acid;
4-Hydroxy-N-(1-methyl-1-phenylethyl)-2-pyridazin-3-ylpyrimidine-5-carboxamide;
N-[bis(4-methoxyphenyl)methyl]-4-hydroxy-2-pyridazin-3-ylpyrimidine-5-carboxamide;
N-[bis(4-methoxyphenyl)methyl]-4-hydroxy-2-pyridazin-3-ylpyrimidine-5-carboxamide 1,3-dihydroxy-2-(hydroxymethyl)propan-2-ammonium salt;
N-[bis(4-methoxyphenyl)methyl]-4-hydroxy-2-pyridazin-3-ylpyrimidine-5-carboxamide potassium salt;
N-[bis(4-hydroxyphenyl)methyl]-4-hydroxy-2-pyridazin-3-ylpyrimidine-5-carboxamide;
N-(4-fluorobenzyl)-4-hydroxy-2-pyridin-2-ylpyrimidine-5-carboxamide;
4-Hydroxy-N-(1-methyl-1-phenylethyl)-2-(1H-pyrazol-1-yl)pyrimidine-5-carboxamide;
N-[(1S)-1-(4-bromophenyl)ethyl]-4-hydroxy-2-pyridazin-3-ylpyrimidine-5-carboxamide;
N-(diphenylmethyl)-4-hydroxy-2-pyridazin-3-ylpyrimidine-5-carboxamide;
4-hydroxy-N-(1-phenylcyclohexyl)-2-pyridazin-3-ylpyrimidine-5-carboxamide;
N-(biphenyl-4-ylmethyl)-4-hydroxy-2-pyridazin-3-ylpyrimidine-5-carboxamide;

N-(biphenyl-3-ylmethyl)-4-hydroxy-2-(2-methyl-1,3-thiazol-4-yl)pyrimidine-5-carboxamide;
4-Hydroxy-N-(1-methyl-1-phenylethyl)-2-(1,3-thiazol-4-yl)pyrimidine-5-carboxamide;
2-(3,5-Dimethyl-1H-pyrazol-1-yl)-4-hydroxy-N-[4-(trifluoromethoxy)benzyl]pyrimidine-5-carboxamide;
N-[1-(4-fluorophenyl)ethyl]-4-hydroxy-2-(1H-pyrazol-1-yl)pyrimidine-5-carboxamide;
N-[(1S)-1-(4-fluorophenyl)ethyl]-4-hydroxy-2-(1H-pyrazol-1-yl)pyrimidine-5-carboxamide;
N-[(1R)-1-(4-fluorophenyl)ethyl]-4-hydroxy-2-(1H-pyrazol-1-yl)pyrimidine-5-carboxamide;
N-[1-(4-fluorophenyl)-1-methylethyl]-4-hydroxy-2-(1H-pyrazol-1-yl)pyrimidine-5-carboxamide;
4-Hydroxy-N-{1-methyl-1-[6-(trifluoromethyl)pyridin-3-yl]ethyl}-2-(1H-pyrazol-1-yl)pyrimidine-5-carboxamide; and pharmaceutically acceptable salts and solvates thereof.

In another embodiment of the invention, the compounds of the invention include:
2-(4-Bromopyridin-2-yl)-4-hydroxy-N-(1-methyl-1-phenylethyl)pyrimidine-5-carboxamide;
2-(4-Hydroxy-5-{[(1-methyl-1-phenylethyl)amino]carbonyl}pyrimidin-2-yl)isonicotinic acid;
6-(5-{[(4-Fluorobenzyl)amino]carbonyl}-4-hydroxypyrimidin-2-yl)nicotinic acid;
4-Hydroxy-N-(1-methyl-1-phenylethyl)-2-pyridazin-3-ylpyrimidine-5-carboxamide;
N-[bis(4-methoxyphenyl)methyl]-4-hydroxy-2-pyridazin-3-ylpyrimidine-5-carboxamide;
N-[bis(4-methoxyphenyl)methyl]4-hydroxy-2-pyridazin-3-ylpyrimidine-5-carboxamide 1,3-dihydroxy-2-(hydroxymethyl)propan-2-ammonium salt;
N-[bis(4-methoxyphenyl)methyl]-4-hydroxy-2-pyridazin-3-ylpyrimidine-5-carboxamide potassium salt;
N-[bis(4-hydroxyphenyl)methyl]-4-hydroxy-2-pyridazin-3-ylpyrimidine-5-carboxamide;
N-(4-fluorobenzyl)-4-hydroxy-2-pyridin-2-ylpyrimidine-5-carboxamide; and pharmaceutically acceptable salts and solvates thereof.

In another embodiment of the invention, the compounds include:
N-[bis(4-methoxyphenyl)methyl]-4-hydroxy-2-pyridazin-3-ylpyrimidine-5-carboxamide;
N-[bis(4-methoxyphenyl)methyl]-4-hydroxy-2-pyridazin-3-ylpyrimidine-5-carboxamide 1,3-dihydroxy-2-(hydroxymethyl)propan-2-ammonium salt;
N-[bis(4-methoxyphenyl)methyl]-4-hydroxy-2-pyridazin-3-ylpyrimidine-5-carboxamide potassium salt;
N-[bis(4-hydroxyphenyl)methyl]-4-hydroxy-2-pyridazin-3-ylpyrimidine-5-carboxamide;
and pharmaceutically acceptable salts and solvates thereof.

In one variant of this embodiment, the compounds include:
N-[bis(4-methoxyphenyl)methyl]-4-hydroxy-2-pyridazin-3-ylpyrimidine-5-carboxamide and pharmaceutically acceptable salts and solvates thereof, including, for example, N-[bis(4-methoxyphenyl)methyl]-4-hydroxy-2-pyridazin-3-ylpyrimidine-5-carboxamide 1,3-dihydroxy-2-(hydroxymethyl)propan-2-ammonium salt; and N-[bis(4-methoxyphenyl)methyl]-4-hydroxy-2-pyridazin-3-ylpyrimidine-5-carboxamide potassium salt.

In another variant of this embodiment the compounds includes N-[bis(4-hydroxyphenyl)methyl]-4-hydroxy-2-pyridazin-3-ylpyrimidine-5-carboxamide, and pharmaceutically acceptable salts and solvates thereof.

In another embodiment the compounds of the invention include:
2-(4-Bromopyridin-2-yl)-4-hydroxy-N-(1-methyl-1-phenylethyl)pyrimidine-5-carboxamide;
2-(4-Hydroxy-5-{[(1-methyl-1-phenylethyl)amino]carbonyl}pyrimidin-2-yl)isonicotinic acid;
6-(5-{[(4-Fluorobenzyl)amino]carbonyl}4-hydroxypyrimidin-2-yl)nicotinic acid;
4-Hydroxy-N-(1-methyl-1-phenylethyl)-2-pyridazin-3-ylpyrimidine-5-carboxamide;
N-(4-fluorobenzyl)-4-hydroxy-2-pyridin-2-ylpyrimidine-5-carboxamide; and pharmaceutically acceptable salts and solvates thereof.

Structural representations of compounds having substituents terminating with a methyl group may display the terminal methyl group either using the characters "$CH_3$", e.g. "—$CH_3$" or using a straight line representing the presence of the methyl group, "—" e.g. , i.e.,

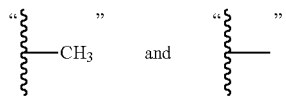

have equivalent meanings.

For variable definitions containing terms having repeated terms, e.g., $(CR^iR^j)_r$, where r is the integer 2, $R^i$ is a defined variable, and $R^j$ is a defined variable, the value of $R^i$ may differ in each instance in which it occurs, and the value of $R^j$ may differ in each instance in which it occurs. For example, if $R^i$ and $R^j$ are independently selected from the group consisting of methyl, ethyl, propyl and butyl, then $(CR^iR^j)_2$ can be

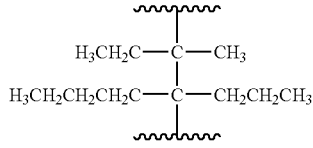

Optical Isomers—Diastereomers—Geometric Isomers—Tautomers

Compounds described herein may contain an asymmetric center and may thus exist as enantiomers. Where the compounds according to the invention possess two or more asymmetric centers, they may additionally exist as diastereomers. The present invention includes all such possible stereoisomers as substantially pure resolved enantiomers, racemic mixtures thereof, as well as mixtures of diastereomers. The above Formula I is shown without a definitive stereochemistry at certain positions. The present invention includes all stereoisomers of Formula I and pharmaceutically acceptable salts and solvates thereof. Unless specifically mentioned otherwise, reference to one isomer applies to any of the possible isomers. Whenever the isomeric composition is unspecified, all possible isomers are included. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general Formula I may be obtained by stereospecific synthesis using optically pure starting materials or reagents of known configuration.

When compounds described herein contain olefinic double bonds, unless specified otherwise, such double bonds are meant to include both E and Z geometric isomers.

Some of the compounds described herein may exist with different points of attachment of hydrogen, referred to as tautomers. For example, compounds including carbonyl —$CH_2C(O)$— groups (keto forms) may undergo tautomerism to form hydroxyl —CH=C(OH)— groups (enol forms). Both keto and enol forms, individually as well as mixtures thereof, are included within the scope of the present invention.

Salts

Pharmaceutically acceptable salts include both the metallic (inorganic) salts and organic salts; a list of which is given in *Remington's Pharmaceutical Sciences,* 17th Edition, pg. 1418 (1985). It is well known to one skilled in the art that an appropriate salt form is chosen based on physical and chemical stability, flowability, hydro-scopicity and solubility. The term "pharmaceutically acceptable salts" refers to salts prepared from pharmaceutically acceptable non-toxic bases or acids. When the compound of the present invention is acidic, its corresponding salt can be conveniently prepared from inorganic bases or organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from organic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from inorganic or organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

Solvates

The present invention includes within its scope solvates of compounds of Formula I. As used herein, the term "solvate" refers to a complex of variable stoichiometry formed by a solute (i.e., a compound of Formula I) or a pharmaceutically acceptable salt thereof and a solvent that does not interfere with the biological activity of the solute. Examples of solvents include, but are not limited to water, ethanol, and acetic acid. When the solvent is water, the solvate is known as hydrate; hydrate includes, but is not limited to, hemi-, mono-, sesqui-, di- and trihydrates.

Prodrugs

The present invention includes within its scope the use of prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with a compound of formula I or with a compound which may not be a compound of formula I, but which converts to a compound of formula I in vivo after administration to the patient. Conventional procedures for the selection and preparation of suitable prodrug derivatives are described, for example, in "Design of Prodrugs," ed. H. Bundgaard, Elsevier, 1985.

Utilities

Compounds of the present invention are inhibitors of hypoxia-inducible factor (HIF) prolyl hydroxylases, and as such are useful in the treatment and prevention of diseases and conditions in which HIF modulation is desirable, such as anemia and ischemia. Compounds of the invention can be used in a selective and controlled manner to induce hypoxia-inducible factor stabilization and to rapidly and reversibly stimulate erythropoietin production and secretion. Accordingly, another aspect of the present invention provides a method of treating or preventing a disease or condition in a mammal, the treatment or prevention of which is effected or facilitated by HIF prolyl hydroxylase inhibition, which comprises administering an amount of a compound of Formula I that is effective for inhibiting HIF prolyl hydroxylase. This aspect of the present invention further includes the use of a compound of Formula I in the manufacture of a medicament for the treatment or prevention of a disease or condition modulated by HIP prolyl hydroxylase.

In one embodiment is a method of enhancing endogenous production of erythropoietin in a mammal which comprises administering to said mammal an amount of a compound of Formula I that is effective for enhancing endogenous production of erythropoietin.

Another embodiment is a method of treating anemia in a mammal which comprises administering to said mammal a therapeutically effective amount of a compound of Formula I. "Anemia" includes, but is not limited to, chronic kidney disease anemia, chemotherapy-induced anemia (e.g., anemia resulting from antiviral drug regimens for infectious diseases, such as HIV and hepatitis C virus), anemia of chronic disease, anemia associated with cancer conditions, anemia resulting from radiation treatment for cancer, anemias of chronic immune disorders such as rheumatoid arthritis, inflammatory bowel disease, and lupus, and anemias due to menstruation or of senescence or in other individuals with iron processing deficiencies such as those who are iron-replete but unable to utilize iron properly.

Another embodiment is a method of treating ischemic diseases in a mammal, which comprises administering to said mammal a therapeutically effective amount of a compound of Formula I.

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I.

Route of Administration/Dosage

The compounds of this invention can be administered for the treatment or prevention of afflictions, diseases and illnesses according to the invention by any means that effects contact of the active ingredient compound with the site of action in the body of a warm-blooded animal. For example, administration can be oral, topical, including transdermal, ocular, buccal, intranasal, inhalation, intravaginal, rectal, intracisternal and parenteral. The term "parenteral" as used herein refers to modes of administration which include subcutaneous, intravenous, intramuscular, intraarticular injection or infusion, intrasternal and intraperitoneal. For the purpose of this disclosure, a warm-blooded animal is a member of the animal kingdom possessed of a homeostatic mechanism and includes mammals and birds.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will be dependent on the age, health and weight of the recipient, the extent of disease, kind of concurrent treatment, if any, frequency of treatment and the nature of the effect desired. Usually, a daily dosage of active ingredient compound will be from about 0.1-2000 milligrams per day. Ordinarily, from 10 to 500 milligrams per day in one or more applications is effective to obtain desired results. These dosages are the effective amounts for the treatment and prevention of afflictions, diseases and illnesses described above, e.g., anemia.

Pharmaceutical Composition

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

The pharmaceutical compositions of the present invention comprise a compound represented by Formula I (or a pharmaceutically acceptable salt or solvate thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

The active ingredient can be administered orally in solid dosage forms, such as capsules, tablets, troches, dragées, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene gycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

For administration by inhalation, the compounds of the present invention may be conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention include, but are not limited to, hard and soft gelatin capsules, tablets, parenteral injectables, and oral suspensions.

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

A parenteral composition suitable for administration by injection is prepared by stirring 1.5% by weight of active ingredient in 10% by volume propylene glycol. The solution is made to volume with water for injection and sterilized.

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

Compounds of the invention can be administered as the sole active ingredient or in combination with a second active ingredient, including other active ingredients known to be useful for improving the level of erythropoietin in a patient.

Abbreviations Used in the Description of the Preparation of the Compounds of the Present Invention:

| | |
|---|---|
| AcOH | Acetic acid |
| aq | Aqueous |
| brine | Saturated aqueous sodium chloride solution |
| CDI | 1,1'-carbonyldiimidazole |
| CO | Carbon monoxide |
| DCM | Dichloromethane |
| Dppf | 1,1''-bis(diphenylphosphino)ferrocene |
| DBU | 1,8-diazabicyclo[5.4.0]undec-7-ene |
| DIEA | N,N-diisopropylethylamine |
| DMAP | 4-N,N-dimethylaminopyridine |
| DMF | N,N-dimethylformamide |
| DMSO | Dimethyl sulfoxide |
| EtOAc | Ethyl acetate |
| Et (et) | Ethyl |
| EtOH | Ethanol |
| Et$_2$O or ether | Diethyl ether |
| g | Grams |
| h or hr | Hour |
| HATU | O-(7-Azabenzotriazol-1-yl)-N,N,N',N'-tetramethyluronium hexafluorophosphate |
| HCl | Hydrochloric acid |
| HPLC | High-performance liquid chromatography |
| i-PrOH or IPA | Isopropyl alcohol |
| m-CPBA | 3-chloroperbenzoic acid |
| mg | Milligrams |
| mL | Milliliters |
| mmol | Millimole |
| MeCN | Acetonitrile |
| MeOH | Methanol |
| min | Minutes |
| ms or MS | Mass spectrum |
| μg | Microgram(s) |
| μL | Microliters |
| NaHSO$_4$ | sodium bisulfate |
| NaOEt | Sodium ethoxide |
| NaOMe | Sodium methoxide |
| Na$_2$SO$_4$ | Sodium sulfate |
| NH$_4$Cl | ammonium chloride |

Abbreviations Used in the Description of the Preparation of the Compounds of the Present Invention:

| | |
|---|---|
| NH$_4$OH | ammonium hydroxide |
| R$_t$ | Retention time |
| rt | Room temperature |
| TFA | Trifluoroacetic acid |
| THF | Tetrahydrofuran |

SYNTHESIS

The compounds of this invention may be prepared by employing reactions as shown in the following schemes, in addition to other standard manipulations that are known in the literature or exemplified in the experimental procedures. The illustrative schemes below, therefore, are not limited by the compounds listed or by any particular substituents employed for illustrative purposes. Substituent numbering as shown in the schemes does not necessarily correlate to that used in the claims and often, for clarity, a single substituent is shown attached to the compound in place of multiple substituents which are allowed under the definitions of Formula I defined previously.

The following schemes and descriptions illustrate methods which may be employed for the synthesis of the novel compounds described in this invention. All substituents are as defined above unless indicated otherwise. Several strategies based upon synthetic transformations known in the literature of organic synthesis may be employed for the preparation of the title compounds of general formula I. The choice of the method employed is influenced by the selection of the desired substituent groups (R$^1$ through R$^4$ and A) in the title compounds of general formula I.

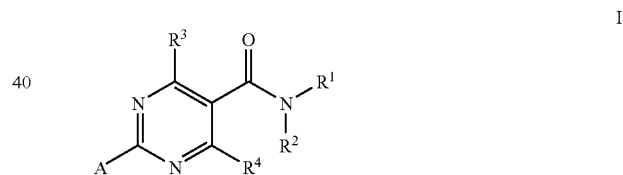

One generally useful method for the synthesis of the title compounds of general formula I wherein the substituent R$^3$ is a hydroxyl group is illustrated in reaction Scheme 1.

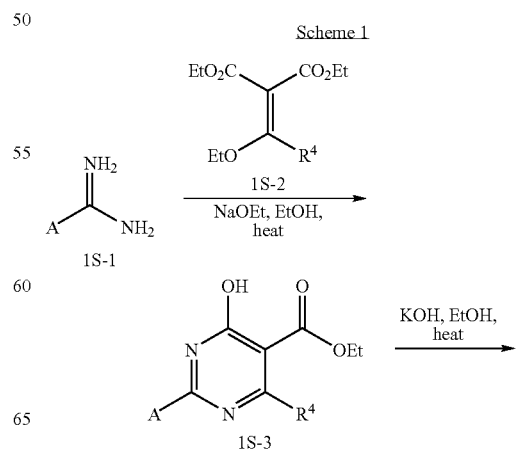

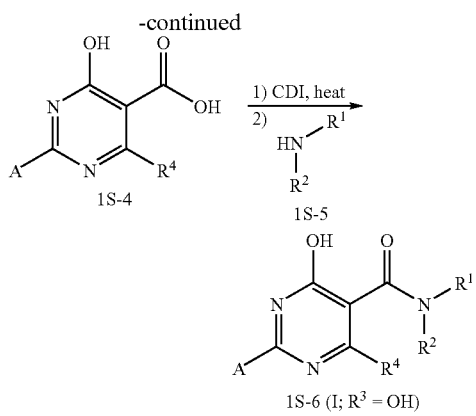

This method involves the initial synthesis of a substituted alkyl 4-hydroxypyrimidine-5-carboxylate of general formula 1S-3. After the synthesis of this heterocyclic system is complete, the ester group is then hydrolyzed and the resulting acid is converted to an amide of general formula I. The method for the synthesis of alkyl 4-hydroxypyrimidine-5-carboxylates presented in reaction scheme 1 is based upon methods appearing in the chemical literature, for instance in the work of Dostert et al. and Juby et al. (Dostert, P.; Imbert, T.; Ancher, J. F.; Langlois, M.; Bucher, B.; Mocquet, G. Eur. J. Med. Chem. 1982, 17, 43744. Juby, P. F.; Hudyma, T. W.; Brown, M.; Essery, J. M.; Partyka, R. A. J. Med. Chem. 1979, 22, 263-9).

In this method, an amidine or salt thereof of general formula 1S-1 is reacted with an optionally substituted diethyl ethoxymethylenemalonate of general formula 1S-2. This reaction is usually conducted using a base such as sodium or potassium ethoxide in ethanol. The alkoxide base and the alcohol solvent are chosen to correspond to the esters present in reagent 1S-2 to prevent the formation of mixtures of esters in the product of general formula 1S-3. The reaction is conducted at elevated temperature, typically at the reflux temperature of the solvent and the reaction is generally completed within 1-4 hours. It is also convenient to conduct this reaction under microwave heating in sealed reaction vessels. In this instance, the reaction is generally conducted at temperatures between 80 and 120° C. and the reactions are typically completed in 5-30 minutes.

The ester of general formula 1S-3 which is produced in this reaction may be isolated by partitioning the reaction between water and an organic solvent, followed by extraction of the product and purification by crystallization or chromatographic methods. However, it is also possible to conduct the hydrolysis of the ester of general formula 1S-3 in the same reaction mixture. In this case, a second base such as aqueous sodium or potassium hydroxide is added to the reaction and the mixture is heated again until ester hydrolysis is complete. This second reaction is also conducted at elevated temperatures, for instance at the reflux temperature of the reaction mixture and for periods of 1-3 hours. Alternatively, the hydrolysis reaction can also be conducted with microwave heating in a reactor at 80-120° C. for periods of 5 to 30 minutes. After the hydrolysis reaction is complete, the acid of general formula 1S-4 is obtained by diluting the reaction mixture into water and isolating the product by precipitation or extraction into an organic solvent. Further purification may be accomplished by recrystallization or chromatographic methods.

The remaining step of the synthesis involves reaction of the carboxylic acids of general formula 1S-4 with a primary or secondary amine of general formula 1S-5 to afford the amide present in the title compounds of general formula I. Many of the methods for the formation of amide bonds reported in the literature of organic synthesis involve initial activation of the carboxylic acid, for instance conversion to an acid chloride, mixed anhydride or the like. One method for the formation of the amides of general formula I that is broadly applicable, involves initial activation with 1,1'-carbonyldiimidazole (CDI). In this case, the acid of general formula 1S-4 is reacted with CDI in a polar aprotic solvent such as DMF, NMP or the like at a temperature between 90 to 120° C. for a period of 15 minutes to 2 hours. Alternatively, the activation step may be conveniently accomplished by heating the reaction mixture in a microwave reactor at a temperature between 100-120° C. for periods of 5-30 minutes.

Once the formation of the acylimidazole adduct is complete, an amine of general formula 1S-5 is added and the reaction mixture is again heated for a period of 0.5 to 2 hours at 90 to 120° C. or for 5 to 30 minutes in a microwave reactor at 100-120° C. If the amine of general formula 1S-5 is obtained as a salt such as a hydrochloride salt, then one equivalent of a tertiary amine base such as triethylamine or N,N-diethylisopropylamine is also added to the reaction mixture. After the amide bond formation is complete, the reaction mixture is diluted into water and the product 1S-6 is then either precipitated or extracted into an organic solvent. Following isolation, the compound of general formula 1S-6, which corresponds to the title compounds of general formula I wherein $R^3$ is a hydroxyl group, is then purified by recrystallization or chromatographic methods.

Another method for the synthesis of the compounds of general formula 1S-6, which inverts the order of the steps in which the title compounds are assembled is based upon a manuscript by Chen et al. (Chen, W.; Feng, J.; Tu, H. Huaxue Tongbao, 2006, 69, 623-6). This synthetic route which is illustrated in reaction scheme 2 begins with the reaction of an amine of general formula 1S-5 with methyl malonyl chloride to form an amide of general formula 2S-7. The reaction is conducted in a suitable inert solvent such as acetonitrile, dichloromethane or the like and in the presence of a tertiary amine base such as triethylamine or N,N-diethylisopropylamine. The reaction proceeds at room temperature and is generally completed within 30 minutes to a few hours. After a standard aqueous workup and isolation, the amide 2S-7 is then reacted with a substituted carboxamide dimethyl acetal of general formula 2S-8. This later step is conducted in aprotic solvents such as THF, DMF or the like at elevated temperature, for instance at 60° C. Reaction times are typically between 30 minutes and 6 hours and the vinylogous amide of general formula S2-9 is the product. The final step of this alternate synthetic method involves condensation of the vinylogous amide general formula 2S-9 with an amidine derivative of general formula 1S-1.

This reaction is typically conducted in a polar aprotic solvent such as DMF, NMP or a similar solvent, at a temperature between 90 and 120° C., and in the presence of a strong organic base like DBU. If the amidine derivative of general formula 1S-1 is obtained as a salt, then an additional equivalent of the organic base is employed. After this cyclization is complete, the reaction mixture is subjected to an aqueous workup and the product of general formula 1S-6 is isolated, purified and used as described in reaction Scheme 1 above.

Scheme 2

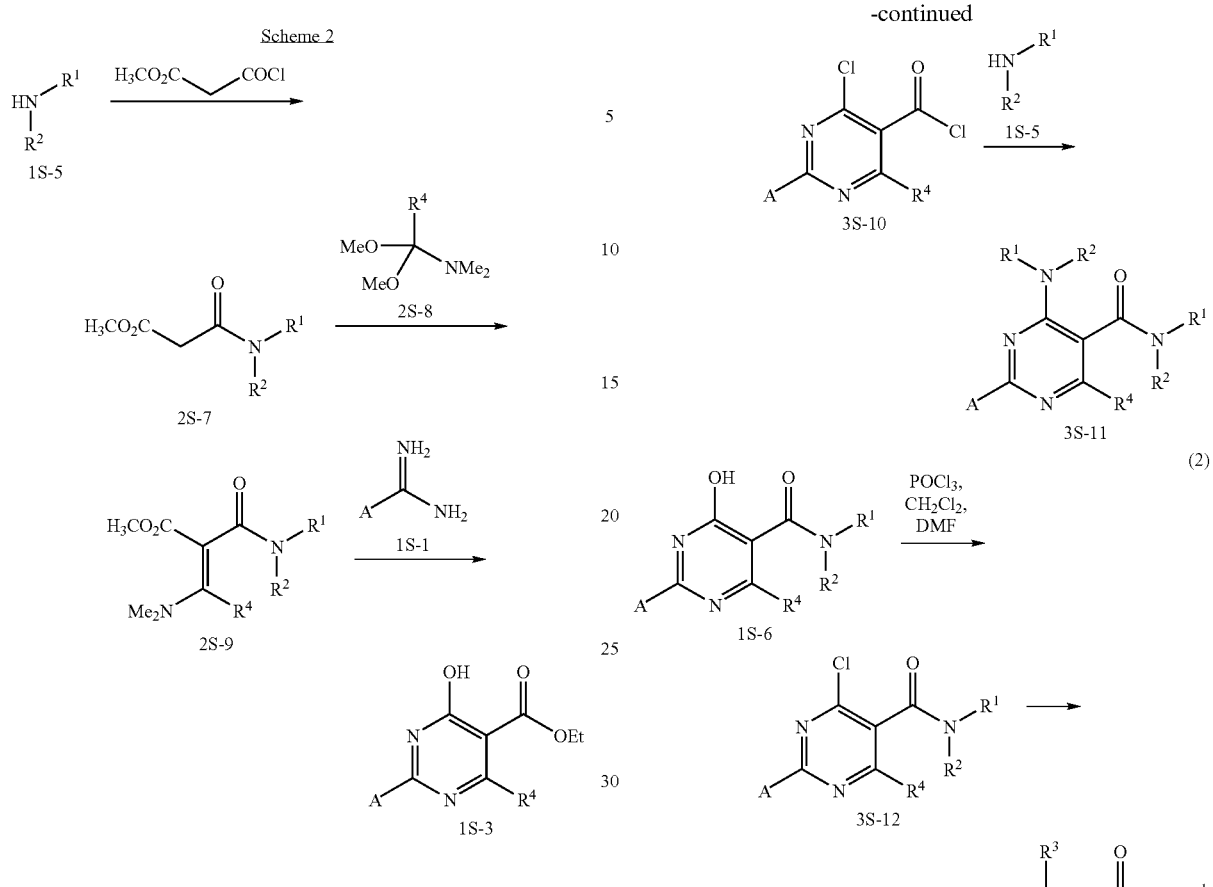

When the amidine of general formula 1S-1 used in the preceding reaction schemes is selected which is not commercially available, it may be prepared by a variety of methods known in the literature of organic synthesis. Amidines are commonly prepared from nitrites using the Pinner reaction and variations thereof (see Amidines and N-substituted amidines. Dunn, Peter J. in Comprehensive Organic Functional Group Transformations 1995, 5, 741-82, 1161-308 Editor(s): Katrizky, Alan R.; Meth-Cohn, Otto; Rees, Charles Wayne. Publisher: Elsevier, Oxford, UK). Amidines may also be prepared from esters using the method reported by Gielen et al. (Gielen, H.; Alonso-Alija, C.; Hendrix, M.; Niewohner, U.; Schauss, D. *Tetrahedron Lett.* 2002, 43, 419-21).

Additional compounds that are within the scope of this invention may be synthetically prepared from compounds illustrated in reaction Schemes 1 and 2. For example, the hydroxyl group present at the pyrimidine 4-position in compounds of general formulae 1S-3, 1S-4, or 1S-6 may be readily converted to a halogen substituent upon reaction with a suitable halogenating reagent.

Scheme 3

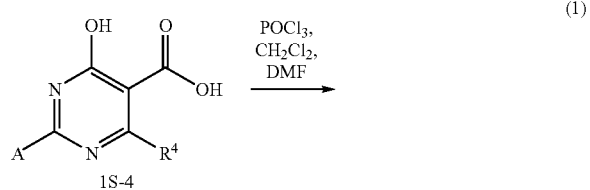

Reaction Scheme 3 illustrates this process for the compounds to general formula 1S-4 and 1S-6 in equations 1 and 2 respectively. In equation 1 of Scheme 3, the reaction of the 4-hydroxypyrimidine-5-carboxylic acid 1S-4 with phosphorus oxychloride in a mixture of dichloromethane and DMF affords the substituted 4-chloropyrimidine-5-carbonyl chloride 3S-10. Intermediate 3S-10 may then be reacted with an amine of general formula S1-5 to afford either a compound of general formula 3S-12 or with an excess of the amine 1S-5 to produce compounds of general formula 3S-11. Similarly, the reaction of compounds of general formula 6 with phosphorus oxychloride in a mixture of dichloromethane and DMF affords the 4-chloropyrimidine derivative 3S-12. Compounds of general formula 3S-12 are versatile intermediates for the introduction of a variety of substituent groups $R^3$ that are within the scope of this invention using methods such as metal-catalyzed cross coupling reactions, nucleophilic aromatic substitution reactions, and the like. Additionally, the chlorine atom at the pyrimidine 4-position may be subjected to reduction with reagents such as zinc in acetic acid when it is desired that $R^3$ be a hydrogen atom.

The methods presented in reaction Schemes 1 and 2 may be further generalized when it is desired to prepare compounds of general formula I where neither of the $R^3$ or $R^4$ substituents are hydroxyl groups.

Scheme 4

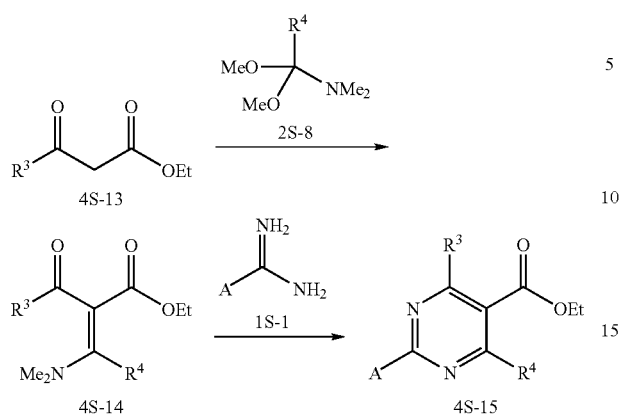

Reaction Scheme 4 illustrates the process beginning with a beta-ketoester of general formula 4S-13 bearing the $R^3$ substituent. The ester of general formula 4S-13 is condensed with a carboxamide dimethyl acetal of general formula 8 to afford the vinylogous amide of general formula 4S-14. The intermediate 4S-14 is then reacted with an amidine derivative of general formula 1S-1 using the method of Schenone et al. (Schenone, P.; Sansebastiano, L.; Mosti, L. *J. Heterocyclic Chem.* 1990, 27, 295) to afford the alkyl pyrimidine-5-carboxylate of general formula 4S-15. The compounds of general formula 4S-15 are then converted to the title compounds of general formula I using the methods described previously.

In instances where the substituent A is selected to be a five-membered heterocyclic ring, it is possible that this heterocyclic group be bonded to the carbon atom at the 2-position of the pyrimidine ring through either a carbon-carbon or a carbon-nitrogen bond. In the case of attachment through a carbon-carbon bond, the precursor for the substituent A is an amidine of general formula 1 and the method of synthesis of the title compound of general formula I is as described in the preceding reaction schemes.

In the case of attachment through a carbon-nitrogen bond, the precursor for the substituent A is a guanidine of general formula 5S-16. In this example, the synthesis begins with the condensation of the guanidine derivative of general formula 5S-16 with a substituted vinylogous amide of general formula 4S-14 (or a diethyl ethoxymethylenemalonate of general formula 2 when it is desired that $R^3$=OH) to afford the substituted 2-amino-4-hydroxypyrimidine-5-carboxylate derivative of general formula 5S-17. Ester hydrolysis and subsequent amide bond formation as described above affords the title compound (5S-19) of general formula I wherein the group A is a five-membered heterocyclic group attached to the pyrimidine 2-position with a carbon-nitrogen bond.

Scheme 5

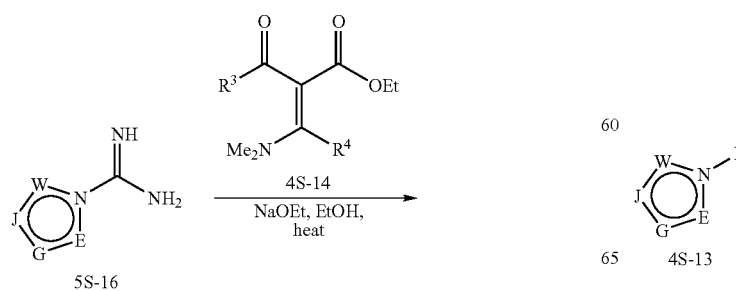

In cases when the guanidine derivative (5S-16) bearing the desired substituents is not commercially available, it may be synthesized using methods for the guanidinylation of amines. Numerous methods for the guanidinylation of amines have appeared in the literature of organic synthesis (see Katritzky, A. R.; Rogovoy, B. V. ARKIVOC 2005, 4, 49-87; One generally applicable method involves the reaction of an amine of general formula 4S-13 with commercially available 3,5-dimethyl-1-pyrazolylformamidinium nitrate to afford a guanidine of general formula 5S-16 using the method described by Fletcher et al. (Fletcher, D. I.; Ganellin, C. R.; Piergentili, A.; Dunn, P. M.; Jenkinson, D. H. *Bioorg. Med. Chem.* 2007, 15, 5457-79) and illustrated in reaction Scheme 6.

Scheme 6

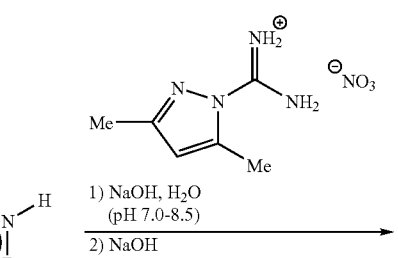

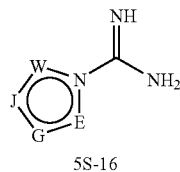

5S-16

It is recognized that the title compounds of general formula I prepared as described above may be further modified using known organic synthetic methods and that the starting materials selected for use in the reaction schemes above may contain functional groups to enable said further transformation. For instance, aromatic rings in the title compounds of general formula I may be subjected to a variety of aromatic substitution reactions such as nitration, halogenation and the like. Aromatic substituent groups in the title compounds of general formula I bearing leaving groups such as halogens, triflates or the like, can be employed in a variety of metal-catalyzed cross coupling reactions to incorporate new substitution patterns. For example, palladium-catalyzed cross coupling reactions such as those described by Suzuki, Stille, Buchwald and others, may be used to introduce a variety of new substituent groups. Substituent groups that may be introduced using such cross-coupling methods include, but are not limited to, alkyl, alkenyl, alkynyl and aryl groups as well as acyl groups (e.g. carboxylic acids, esters, amides, or ketones), hydroxyl and amino or substituted amino groups.

General Methods

Reactions sensitive to moisture or air were performed under nitrogen using anhydrous solvents and reagents. The progress of reactions was determined by either analytical thin layer chromatography (TLC) performed with E. Merck pre-coated TLC plates, silica gel 60F-254, layer thickness 0.25 mm or liquid chromatography-mass spectrum (LC-MS). Analytical HPLC/MS—Standard Method: Mass analysis was performed on a Waters Micromass® ZQ™ with electrospray ionization in positive ion detection mode. High performance liquid chromatography (HPLC) was conducted on an Agilent 1100 series HPLC on Waters C18 XTerra 3.5 μm 3.0×50 mm column with gradient 10:90-100 v/v CH$_3$CN/H$_2$O+v 0.05% TFA over 3.75 min then hold at 100 CH$_3$CN+v 0.05% TFA for 1.75 min; flow rate 1.0 mL/min, UV wavelength 254 nm (all BPLC/MS data was generated with this method unless indicated otherwise). Analytical HPLC/MS—Basic Method: Mass analysis was performed on a Waters Micromass® ZQ™ with electrospray ionization in positive ion detection mode. High performance liquid chromatography (HPLC) was conducted on an Agilent 1100 series HPLC on Waters C 18 XBridge 3.5 μm 3.0×50 mm column with gradient 10:90-98:2 v/v CH$_3$CN/H$_2$O+v 0.025% NH$_4$OH over 3.25 min then hold at 98:2 CH$_3$CN+v 0.025% NH$_4$OH for 2.25 min; flow rate 1.0 mL/min, UV wavelength 254 nm. Concentration of solutions was carried out on a rotary evaporator under reduced pressure. Flash chromatography was performed using a Biotage Horizon or SP1 Flash Chromatography apparatus (Dyax Corp.) on silica gel (32-63 μM particle size, KP-Sil 60 Å packing material type) in pre-packed cartridges or using an ISCO CombiFlash™ Sq 16× or CombiFlash® Companion™ apparatus on silica gel (32-63 μM, 60 Å) in pre-packed cartridges. Microwave reactions were carried out on a Biotage Initiator™ 2.0 or CEM Discover™ system. Preparative HPLC/MS—Standard Method: Mass analysis was performed on a Waters Micromass® ZQ™ with electrospray ionization in positive ion detection mode. High performance liquid chromatography (HPLC) was conducted on a Waters Prep. HPLC System on Waters C18 Sunfire 5 μm 30×100 mm column with gradient 10:90-100 v/v CH$_3$CN/H$_2$O+v 0.1% TFA over 12 min; flow rate 50 mL/min, UV wavelength 210-400 nm.

Preparative HPLC/MS—Non-Polar Method

Mass analysis was performed on a Waters Micromass® ZQ™ with electrospray ionization in positive ion detection mode. High performance liquid chromatography (HPLC) was conducted on a Waters Prep. HPLC System on Waters C18 Sunfire 5 μm 30×100 mm column with gradient 40:60-100 v/v CH$_3$CN/H$_2$O+v 0.1% TFA over 10 min then hold at 100 CH$_3$CN+v 0.1% TFA for 4 min; flow rate 50 mL/min, UV wavelength 210-400 nm.

Preparative HPLC/MS—Basic Method

Mass analysis was performed on a Waters Micromass® ZQ™ with electrospray ionization in positive ion detection mode. High performance liquid chromatography (HPLC) was conducted on a Waters Prep. HPLC System on Waters C18 XBridge 5 μm 50×150 mm column with gradient 10:90-35:65 v/v CH$_3$CN/H$_2$O (pH=10 with NH$_4$OH) over 10 min; flow rate 120 mL/min, UV wavelength 210-400 nm.

INTERMEDIATE 1

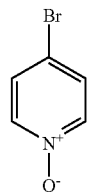

4-Bromopyridine 1-oxide

Step A: 4-Bromopyridine: To a solution of 4-bromopyridine hydrochloride (15.48 g, 79.6 mmol) in a minimal volume of water was added aqueous NaOH (15.92 mL, 79.6 mmol, 5.0 M). The aqueous medium was extracted with Et$_2$O three times, dried (MgSO$_4$), filtered and concentrated to afford the product.

Step B: 4-Bromopyridine 1-oxide: To the product of Step A (11.95 g, 76 mmol) in Et$_2$O was added m-CPBA (22.04 g, 98 mmol). The reaction was stirred at room temperature for 4 h and then filtered to afford the title compound. HPLC/MS: 176.2 (M+1); R$_t$=0.49 min.

INTERMEDIATE 2

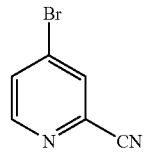

4-Bromopyridine-2-carbonitrile. To the product of Intermediate-1 (3.09 g, 17.76 mmol) in MeCN (20 mL) was added trimethylsilyl cyanide (7.14 mL, 53.5 mmol) and triethylamine (4.92 mL, 35.5 mmol). The reaction was refluxed for 2 h, cooled to room temperature and concentrated. The residue was made alkaline with saturated aq. $Na_2CO_3$, extracted with DCM, dried ($MgSO_4$), filtered and concentrated. The residue was purified by flash chromatography on silica gel gradient eluted with 0-20% EtOAc/hexane to afford the title compound. HPLC/MS: 183.1 (M+1); $R_t$=1.49 min.

INTERMEDIATE 3

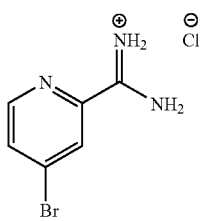

Amino(4-bromopyridin-2-yl)methaniminium chloride. To the product of Intermediate 2 (3.19 g, 17.43 mmol) in MeOH (11 mL) was added sodium methoxide (0.399 mL, 1.743 mmol, 25 wt % in MeOH). The reaction was stirred at room temperature overnight when ammonium chloride (1.026 g, 19.17 mmol) was added. The reaction was refluxed for 2 h, cooled to room temperature and concentrated. The residue was suspended in anhydrous EtOH (100 mL), briefly refluxed and filtered. The filtrate stood at room temperature overnight and was concentrated to afford the title compound. HPLC/MS: 202.0 (M+1); $R_t$=0.35 min/202.1 (M+1); $R_t$=0.51 min.

INTERMEDIATE 4

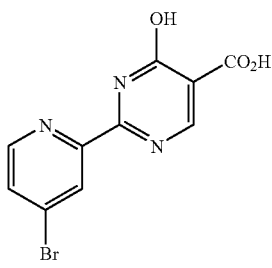

2-(4-Bromopyridin-2-yl)-4-hydroxypyrimidine-5-carboxylic acid. To the product of Intermediate 3 (0.500 g, 2.114 mmol) in EtOH (5.5 mL) was added diethyl ethoxymethylenemalonate (0.427 mL, 2.114 mmol) and sodium methoxide (0.532 mL, 2.326 mmol, 25 wt % in MeOH). The reaction was heated in a microwave for 10 min at 120 ° C. Potassium hydroxide (2.326 mL, 4.65 mmol, 2.0 M) was added and the reaction was heated in a microwave for 10 min at 120 ° C. The reaction was diluted with water, adjusted to pH=2 using conc. aq. HCl and stirred overnight at room temperature. The solids were filtered and rinsed with water and hexane to afford the title compound. BPLC/MS: 298.0 (M+1); $R_t$=1.74 min.

EXAMPLE 1

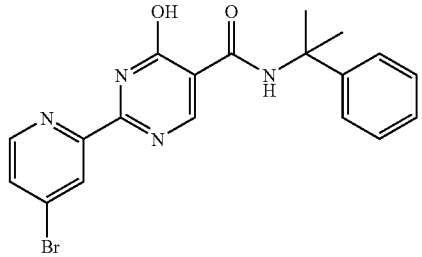

2-(4-Bromopyridin-2-yl)-4-hydroxy-N-(1-methyl-1-phenylethyl)pyrimidine-5-carboxamide To the product of Intermediate 4 (0.220 g, 0.743 mmol) was added CDI (0.120 g, 0.743 mmol) and DMF (3.0 mL). The reaction was heated in a microwave for 10 min at 100 ° C. followed by the addition of cumylamine (0.107 mL, 0.743 mmol). The reaction was stirred at room temperature overnight and concentrated. The residue was diluted with EtOAc and washed with aq. HCl (1 M), brine, dried ($MgSO_4$), filtered and concentrated to afford the title compound. HPLC/MS: 414.9 (M+1); $R_t$=3.05 min.
Note: A portion of the residue was purified by preparative HPLC (Standard Method) for characterization.

EXAMPLE 2

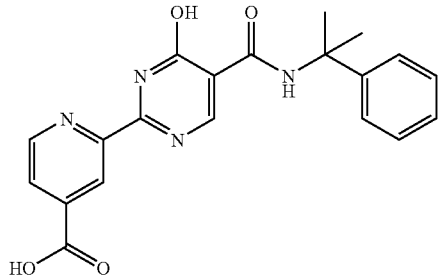

2-(4-Hydroxy-5-{[(1-methyl-1-phenylethyl)amino]carbonyl}pyrimidin-2-yl)isonicotinic acid To the product of Example 1 (0.198 g, 0.479 mmol) in DMSO (5.0 mL) was added potassium acetate (0.188 g, 1.916 mmol), palladium(II) acetate (5.38 mg, 0.024 mmol), and dppf (0.053 g, 0.096 mmol). The reaction was stirred under a CO atmosphere and heated at 120° C. for 30 min. The reaction was diluted with EtOAc, washed with aq. HCl (1M) and concentrated. The residue was purified by preparative HPLC (Non-Polar Method). The material was further purified by flash chromatography on silica gel eluted with EtOH to afford the title compound. HPLC/MS: 379.0 (M+1); $R_t$=2.62 min.

Using the appropriate amidine, Example 3, as shown in Table 1, was prepared in similar fashion to Example 1 and Example 2.

TABLE 1

| Example | Name | HPLC/MS m/z (M + 1) $R_t$ (min) | Structure |
|---|---|---|---|
| Example 3 L-002141176-000P | 6-(5-{[(4-Fluorobenzyl)amino]carbonyl}-4-hydroxypyrimidin-2-yl)nicotinic acid | 369.2 2.46 | 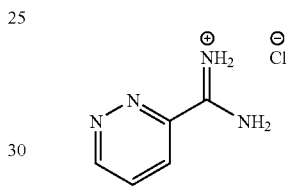 |

INTERMEDIATE 5

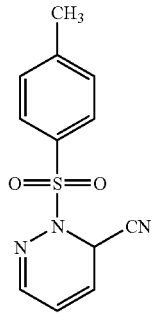

2-[(4-methylphenyl)sulfonyl]-2,3-dihydropridazine-3-carbonitrile. A solution of pyridazine (1.807 mL, 24.98 mmol), aluminum chloride (0.010 g, 0.075 mmol) and trimethylsilyl cyanide (6.03 mL, 45.0 mmol) in DCM (30 mL) was stirred under a nitrogen atmosphere at 0° C. for 20 min. A solution of p-toluenesulfonyl chloride (8.19 g, 43.0 mmol) in DCM (60 mL) was added dropwise over 1 h. The reaction was warmed to room temperature, stirred for an additional 65 h and concentrated. The residue was treated with EtOH (50 mL) and the resulting solids were filtered to afford the title compound. HPLC/MS: 262.1 (M+1); $R_t$=2.51 min.

INTERMEDIATE 6

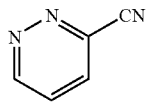

Pyridazine-3-carbonitrile. To the product of Intermediate 5 (4.98 g, 19.06 mmol) in THF (50 mL) was added DBU (3.59 mL, 23.82 mmol). The reaction was stirred at room temperature under a nitrogen atmosphere for 1 h. Saturated aq. NH4Cl (50 mL) was added and the reaction was poured into water (50 mL). The aqueous medium was extracted with EtOAc, dried (MgSO4), filtered and concentrated. The residue was purified by flash chromatography on silica gel gradient eluted with 0-50% EtOAc/hexane to afford the title compound. HPLC/MS: 106.2 (M+1); $R_t$=0.38 min.

INTERMEDIATE 7

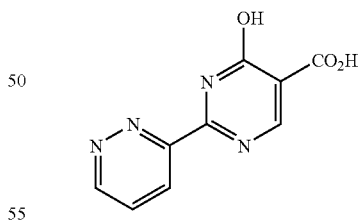

Amino(pyridazin-3-yl)methaniminium chloride. To the product of Intermediate 6 (1.7 g, 16.18 mmol) in MeOH (10 mL) was added sodium methoxide (0.370 mL, 1.618 mmol, 25 wt % in MeOH). The reaction was stirred at room temperature overnight when ammonium chloride (0.952 g, 17.79 mmol) was added. The reaction was refluxed for 2.5 h, cooled to room temperature, diluted with MeOH and concentrated to afford the title compound. HPLC/MS: 123.1 (M+1); $R_t$=0.34 min.

INTERMEDIATE 8

4-Hydroxy-2-pyridazin-3-ylpyrimidine-5-carboxylic acid. To the product of Intermediate 7 (0.500 g, 3.15 mmol) in EtOH (8.0 mL) was added diethyl ethoxymethylenemalonate (0.637 mL, 3.15 mmol) and sodium methoxide (0.793 mL, 3.47 mmol, 25 wt % in MeOH). The reaction was heated in a microwave for 10 min at 120° C. Additional diethyl ethoxymethylenemalonate (0.319 mL, 1.576 mmol) was added and the reaction was heated in a microwave for 10 min at 120° C. Potassium hydroxide (4.73 mL, 9.46 mmol, 2.0 M) was added and the reaction was heated in a microwave for 10 min at 120° C. The reaction was diluted with water and concentrated. The residue was dissolved in a minimal volume of water and extracted with EtOAc. The aqueous layer was adjusted to pH=2 using conc. aq. HCl and stirred for 15 min. The solids were filtered and rinsed with water and hexane to afford the title compound. HPLC/MS: 219.0 (M+1); $R_t$=0.28 min (Basic Method).

EXAMPLE 4

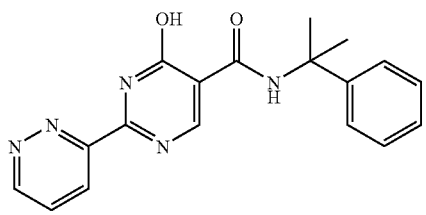

4-Hydroxy-N-(1-methyl-1-phenylethyl)-2-pyridazin-3-ylpyrimidine-5-carboxamide

To the product of Intermediate 8 (0.077 g, 0.353 mmol) was added CDI (0.086 g, 0.529 mmol) and DMF (1.5 mL). The reaction was heated in a microwave for 10 min at 100° C. followed by the addition of cumylamine (0.102 mL, 0.706 mmol). The reaction was stirred at room temperature overnight, diluted with EtOAc, washed with aq. HCl (1 M), brine, dried (MgSO$_4$), filtered and concentrated. The material was crystallized from the residue using EtOH to afford the title compound. HPLC/MS: 336.0 (M+1); $R_t$=2.45 min.

EXAMPLE 5

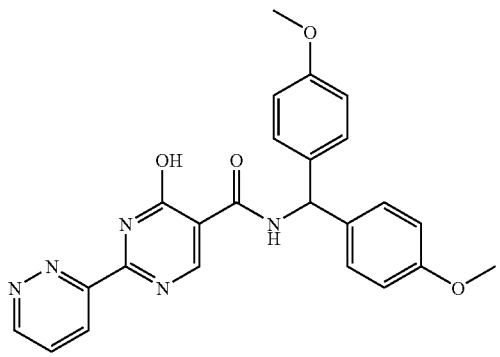

N-[bis(4-methoxyphenyl)methyl]-4-hydroxy-2-pyridazin-3-ylpyrimidine-5-carboxamide To a suspension of Intermediate 8 (14.94 g, 68.5 mmol) in DMF (225 mL) was added TEA (18.98 mL, 137 mmol) and CDI (11.10 g, 68.5 mmol). The reaction was heated at 120° C. for 1 h followed by the addition of 4,4'-dimethoxybenzhydrlamine (14.99 g, 61.6 mmol). The reaction was heated at 115° C. for 1 h, diluted with CHCl$_3$, washed with aq. HCl (1 M), deionized H$_2$O and concentrated. The material was crystallized from the residue using EtOH to afford the title compound. HPLC/MS: 444.18 (M+1); $R_t$=2.90 min.

N-[bis(4-methoxyphenylmethyl]-4-hydroxy-2-pyridazin-3-ylpyrimidine-5-carboxamide 1,3-dihydroxy-2-(hydroxymethyl)propan-2-ammonium salt To a solution of the free acid form of the product of Example 5 prepared above (0.252 g, 0.569 mmol) in DMF (5 mL) was added aq. tris(hydroxymethyl)aminomethane (0.569 mL, 0.569 mmol, 1 M). The reaction was heated with a heat gun for 2 min and concentrated affording the title compound. HPLC/MS: 444.22 (M+1); $R_t$=2.99 min.

N-[bis(4-methoxyphenyl)methyl]-4-hydroxy-2-pyridazin-3-ylpyrimidine-5-carboxamide potassium salt To a solution of the free acid form of the product of Example 5 prepared above (0.308g, 0.695 mmol) in DMF (5 mL) was added aq. potassium hydroxide (0.695 mL, 0.695 mmol, 1 M). The reaction was heated with a heat gun for 2 min and concentrated affording the title compound. HPLC/MS: 444.17 (M+1); $R_t$=2.95 min.

EXAMPLE 6

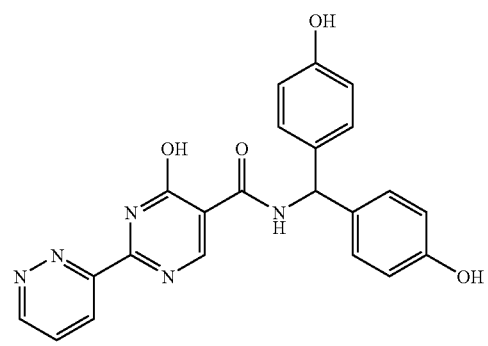

N-[bis(4-hydroxyphenyl)methyl]-4-hydroxy-2-ylpyridazin-3-ylpyrimidine-5-carboxamide The product of Example 5 (0.40 g, 0.90 mmol) was suspended in CH$_2$Cl$_2$ (40 mL) and the mixture was cooled in an ice-water bath. Boron tribromide (4.50 mL, 4.50 mmol, 1 M in CH$_2$Cl$_2$) was added, and the resulting slurry was allowed to come to RT and was stirred for 75 min. Water was added, the aq. layer was adjusted to pH=5, and the solids were isolated by filtration. The product was suspended in EtOAc (20 mL) and the resulting slurry was heated in a water bath at 80° C. for 20 min, then cooled to RT. The resulting white solid was collected by filtration and dried affording the title compound. HPLC/MS: 416.2 (M+1); $R_t$=2.21 min.

INTERMEDIATE 9

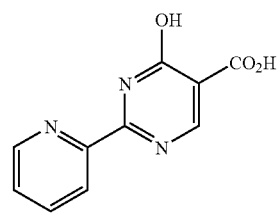

4-Hydroxy-2-pyridin-2-ylpyrimidine-5-carboxylic acid. Using procedures similar to that of Intermediate 7 and Intermediate 8, except using pyridine-2-carbonitrile instead of pyridazine-3-carbonitrile, the title compound was prepared. HPLC/MS: 218.2 (M+1); $R_t$=0.86 min.

EXAMPLE 7

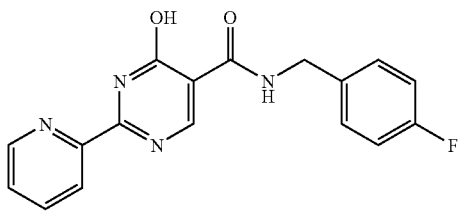

N-(4-fluorobenzyl)-4-hydroxy-2-pyridin-2-ylpyrimidine-5-carboxamide

To the product of Intermediate 10 (0.100 g, 0.460 mmol) in DMF (2.0 mL) was added HATU (0.280 g, 0.737 mmol), DIEA (0.322 L, 1.842 mmol) and 4-fluorobenzylamine (0.105 mL, 0.921 mmol). The reaction was stirred at room temperature for 2 h when additional HATU (0.245 g, 0.645 mmol), DIEA (0.080 mL, 0.460 mmol) and 4-fluorobenzylamine (0.105 mL, 0.921 mmol) were added. The reaction was stirred at room temperature for an additional hour. The reaction was diluted with EtOAc, washed with aq. 10% NaHSO$_4$, water, brine and concentrated. The residue was purified by preparative HPLC (Basic Method) to afford the title compound. HPLC/MS: 325.1 (M+1), $R_t$=2.56 min.

INTERMEDIATE 10

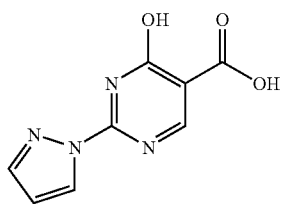

4-hydroxy-2-(1H-pyrazol-1-yl)pyrimidine-5-carboxylic acid

To 1H-pyrazole-1-carboximidamide hydrochloride (44.22 g, 299 mmol) in EtOH (500 mL) was added sodium methoxide (102 mL, 448 mmol, 25 wt % in MeOH) and diethyl ethoxymethylenemalonate (61.0 mL, 299 mmol, 99%). The reaction was heated for about 40 min at 75° C. and then cooled slightly (71° C.) before adding potassium hydroxide (33.5 g, 597) in water (125 mL). The reaction was heated to 75° C. for 1 h. During this time an additional portion of EtOH (100 mL) was added to improve mixing. The reaction was cooled to 40° C. before adding aq. HCl (81.3 mL, 991 mmol, 37%) in portions. The reaction aged for 1 h 40 min and then Et$_2$O (180 mL) was added. The solids were filtered and rinsed with EtOH, Et$_2$O and then hexane. The solid was then suspended in aq. HCl (300 mL, 0.67 M), filtered and washed with aq. HCl (300 mL, 1 M), 2:1 Et$_2$O:EtOH (350 mL), 1:1 Et$_2$O:EtOH (200 mL), Et$_2$O (150 mL) and hexane (150 mL) to afford the title compound. HPLC/MS: 207.2 (M+1); $R_t$=0.61 min.

INTERMEDIATE 11

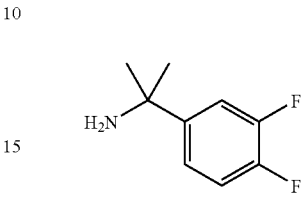

1-(3,4-Difluorophenyl)methanamine. To THF (18 ml) was added cerium(III) chloride (2.84 g, 11.50 mmol) and the solution was purged, backfilled with nitrogen and warmed to 45° C. for 3 h. The reaction was cooled to rt and 3,4-difluorobenzonitrile (0.8 g, 5.75 mmol) was added. The solution was cooled further to −25° C. and methyl lithium/lithium bromide (1.5 M in diethyl ether, 9.59 ml, 14.38 mmol) was added slowly. The reaction was stirred at this temperature for 1 h and ammonium hydroxide solution (28% in water, 4.00 ml, 28.8 mmol) was added and the mixture was allowed to sit overnight at rt. The cerium salts were filtered off and washed with THF. The obtained THF solution was dried with MgSO4, filtered and concentrated. The product was diluted with ethyl ether and THF and HCl (4M in dioxane, 1.438 mL, 5.75 mmol) were added. The residue was concentrated, diluted with hexane and filtered affording the title compound.

EXAMPLE 8

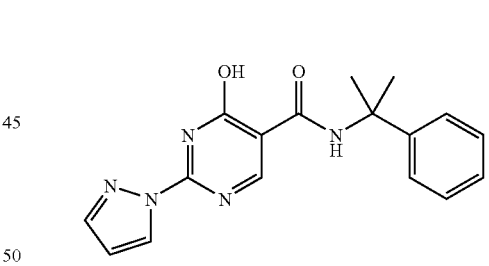

4-Hydroxy-N-(1-methyl-1-phenylethyl)-2-(1H-pyrazol-1-yl)pyrimidine-5-carboxamide The product of Intermediate 10 (8.00 g, 38.8 mmol) was combined with CDI (7.24 g, 44.6 mmol) and DMF (80 mL). The reaction was aged at 105° C. for 45 min and cooled to about 77° C. Cumyl amine (7.26 mL, 50.4 mmol) and NEt$_3$ (5.41 mL, 38.8 mmol) were added and the reaction continued to age at 77° C. for an additional 5 h. The reaction was concentrated and then diluted with CH$_2$Cl$_2$ and washed with aq. HCl (2 M) and water. The organic portion was concentrated and suspended in Et$_2$O (270 mL) and aged for 1 h 40 min before the product was isolated by filtration. The solid was then suspended in 10% EtOH/90% Et$_2$O (200 mL) and aged about 16 hrs before it was isolated by filtration and dried to afford the title compound. HPLC/MS: 342.1 (M+1); $R_t$=2.66 min.

EXAMPLE 9

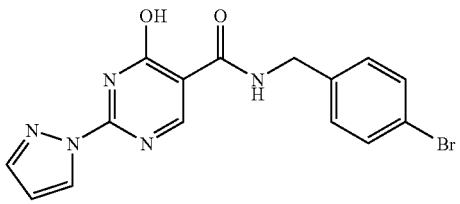

N-(4-bromobenzyl)-4-hydroxy-2-(1H-pyrazol-1-yl) pyrimidine-5-carboxamide

Step A: Methyl 3-[(4-bromobenzyl)amino]-3-oxopropanoate

To 1-(4-bromophenyl)methanamine hydrochloride (8.56 g, 38.5 mmol), MeCN (50 mL) and NEt₃ (5.36 mL, 38.5 mmol) was added methyl 3-chloro-3-oxopropanoate (3.17 mL, 29.6 mmol). The reaction was aged about an hour before NEt₃ (10.7 mL, 77 mmol) was added. The reaction was aged about 20 min and was concentrated. The reaction was diluted with EtOAc and washed with brine and aq. 2M Na₂CO₃ solution followed by aq. 2 M HCl and water. The organic portion was concentrated. The residue was purified by flash chromatography on silica gel gradient eluted with 0-90% EtOAc/hexane to afford the product.

Step B: Methyl 2-{[(4-bromobenzyl)amino]carbonyl}-3-(dimethylamino)acrylate

The product of Step A (5.01 g, 17.5 mmol) in THF (30 mL) was treated to dimethylformamide dimethylacetal (4.97 mL, 35.0 mmol, 94% assay) at 60° C. for about an hour. The reaction was concentrated and used directly in Step C.

Step C: N-(4-bromobenzyl)-4-hydroxy-2-(1H-pyrazol-1-yl)pyrimidine-5-carboxamide

All of the unpurified product of step B was diluted with DMA (28 mL) before adding 1H-pyrazole-1-carboximidamide hydrochloride (5.13 g, 35.0 mmol), and DBU (5.28 mL, 35.0 mmol) at rt. The reaction was aged at 110° C. for about 30 min. The reaction was diluted with EtOAc and washed with aq. 2 M HCl and water. The organic portion was concentrated and diluted with EtOH. The mixture was aged for about 30 min at 75° C. and cooled. The solid is isolated by filtration and washed with EtOH to afford the title compound. HPLC/MS: 374.0 (M+1); $R_t$=2.70 min.

EXAMPLE 10

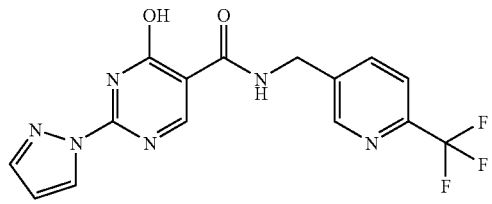

4-Hydroxy-2-(1H-pyrazol-1-yl)-N-{[6-trifluoromethyl)pyridin-3-yl]methyl}pyrimidine-5-carboxamide To the product of Intermediate 10 (100.0 mg, 0.485 mmol) was added CH₂Cl₂ (3 mL) and SO₂Cl₂ (0.485 mL, 1 M in CH₂Cl₂). The solid failed to go into solution. DMF (1.5 mL) and oxalyl chloride (0.047 mL, 0.534 mmol) were added and the reaction was aged about 15 min at rt before it was concentrated. The residue was diluted with CH₂Cl₂ (3 mL) and 1-[6-(trifluoromethyl)pyridin-3-yl]methanamine (85 mg, 0.485 mmol) and NEt₃ (0.338 mL, 2.425 mmol) were added. The reaction was diluted with EtOAc and washed with aq. 10% NaHSO₄ and water. The organic portion was concentrated and diluted with acetone. The solid was isolated by filtration and washed with acetone to afford the title compound. HPLC/MS: 365.1 (M+1); $R_t$=2.30 min.

Using procedures similar to that described in Example 4 and Example 8 the compounds of Examples 11 through 103 were prepared as shown in Table 2.

TABLE 2

| Example | Name | HPLC/MS m/z (M + 1) $R_t$ (min) | Structure |
|---|---|---|---|
| Example 11 | N-(4-fluorobenzyl)-4-hydroxy-2-[5-(trifluoromethyl)pyridin-2-yl]pyrimidine-5-carboxamide | 393.1 2.94 | 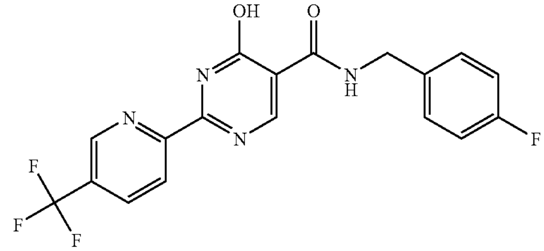 |

TABLE 2-continued

| Example | Name | HPLC/MS m/z (M + 1) R$_t$ (min) | Structure |
|---|---|---|---|
| Example 12 | N-[1-(4-fluorophenyl)ethyl]-4-hydroxy-2-pyridin-2-ylpyrimidine-5-carboxamide | 339.0<br>2.71 | 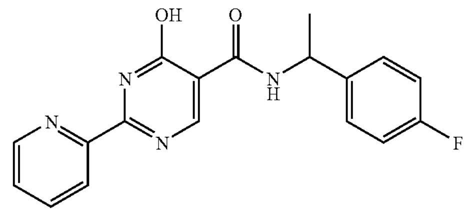 |
| Example 13 | 4-Hydroxy-N-(1-methyl-1-phenylethyl)-2-pyridin-2-ylpyrimidine-5-carboxamide | 335.2<br>2.72 | 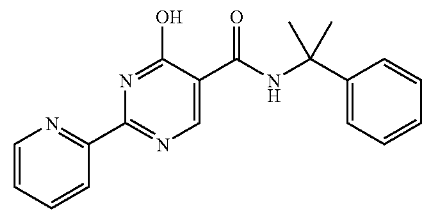 |
| Example 14 | N-[bis(4-methoxyphenyl)methyl]-4-hydroxy-2-pyridin-2-ylpyrimidine-5-carboxamide | 442.8<br>3.15 | 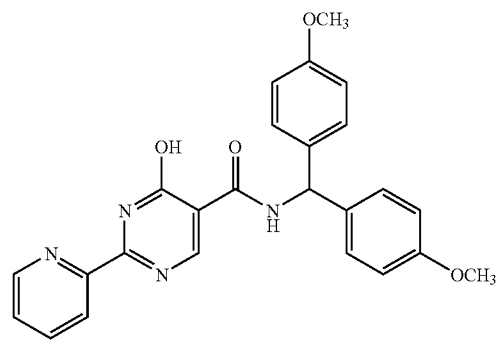 |
| Example 15 | N-(biphenyl-4-ylmethyl)-4-hydroxy-2-(6-methylpyridin-2-yl)pyrimidine-5-carboxamide | 397.1<br>3.28 | 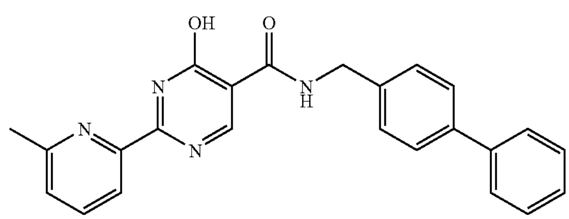 |
| Example 16 | N-(2-chloro-4-fluorophenyl)-4-hydroxy-2-(6-methylpyridin-2-yl)pyrimidine-5-carboxamide | 359.1<br>3.17 | 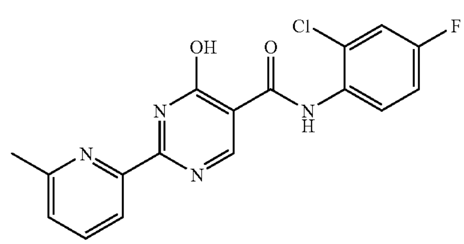 |
| Example 17 | N-(2,4-dichlorobenzyl)-4-hydroxy-2-(6-methylpyridin-2-yl)pyrimidine-5-carboxamide | 389.0<br>3.19 | 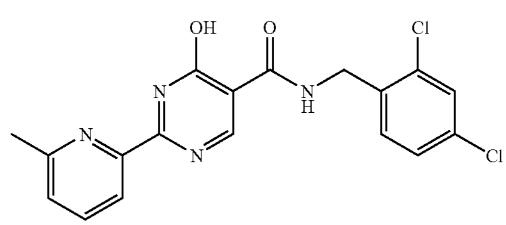 |

TABLE 2-continued

| Example | Name | HPLC/MS m/z (M + 1) R$_t$ (min) | Structure |
|---|---|---|---|
| Example 18 | N-(4-fluorobenzyl)-4-hydroxy-2-pyrazin-2-ylpyrimidine-5-carboxamide | 326.1 2.29 | 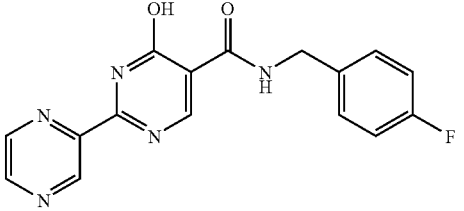 |
| Example 19 | 4-Hydroxy-N-(1-methyl-1-phenylethyl)-2-pyrazin-2-ylpyrimidine-5-carboxamide | 336.2 2.51 | 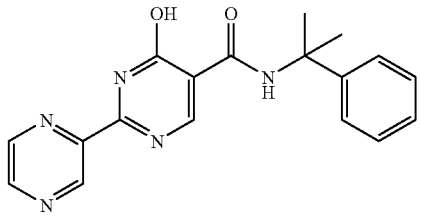 |
| Example 20 | 4-Hydroxy-2-pyrazin-2-yl-N-[4-(trifluoromethyl)benzyl]pyrimidine-5-carboxamide | 376.1 2.68 | 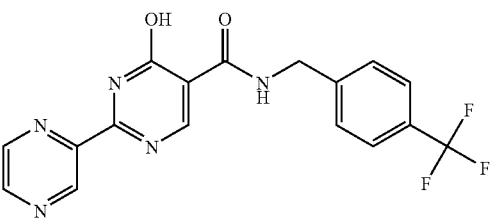 |
| Example 21 | N-(4-fluorobenzyl)-4-hydroxy-2,2'-bipyrimidine-5-carboxamide | 326.2 2.08 | 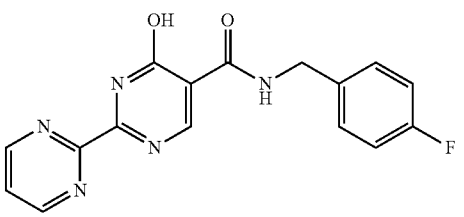 |
| Example 22 | 4-Hydroxy-N-(1-methyl-1-phenylethyl)-2,2'-bipyrimidine-5-carboxamide | 336.2 2.38 | 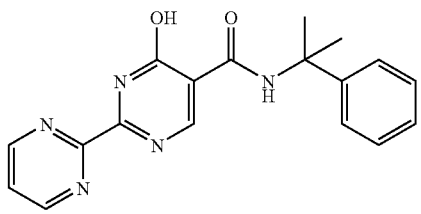 |
| Example 23 | 4-Hydroxy-N-[4-(trifluoromethyl)benzyl]-2,2'-bipyrimidine-5-carboxamide | 376.1 2.55 | 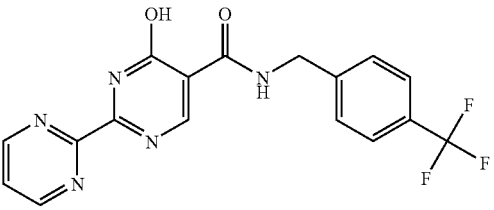 |

TABLE 2-continued

| Example | Name | HPLC/MS m/z (M + 1) R$_t$ (min) | Structure |
|---|---|---|---|
| Example 24 | N-(2-chlorobenzyl)-4-hydroxy-2-pyridazin-3-ylpyrimidine-5-carboxamide | 342.1 1.43 Basic method | 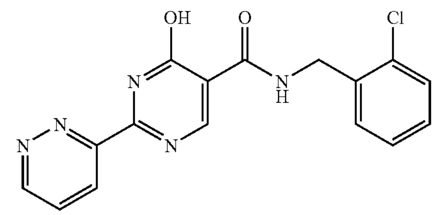 |
| Example 25 | N-[(1S)-1-(4-bromophenyl)ethyl]-4-hydroxy-2-pyridazin-3-ylpyrimidine-5-carboxamide | 399.9 1.84 | 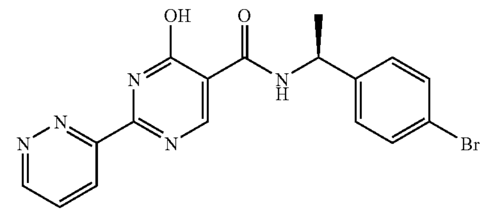 |
| Example 26 | N-(diphenylmethyl)-4-hydroxy-2-pyridazin-3-ylpyrimidine-5-carboxamide | 384.2, 2.79 | 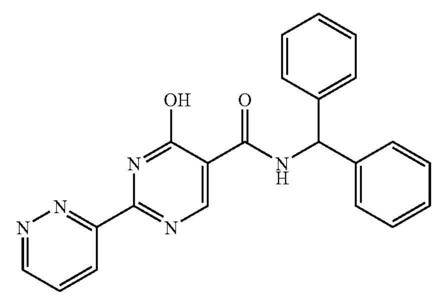 |
| Example 27 | 4-hydroxy-N-(1-phenylcyclohexyl)-2-pyridazin-3-ylpyrimidine-5-carboxamide | 376.1, 1.99 | 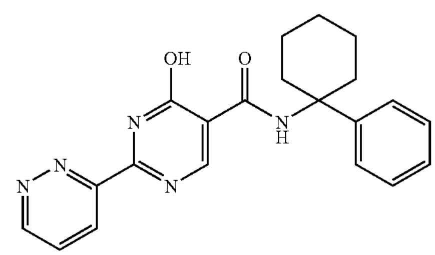 |
| Example 28 | N-(biphenyl-4-ylmethyl)-4-hydroxy-2-pyridazin-3-ylpyrimidine-5-carboxamide | 384.2, 2.01 | 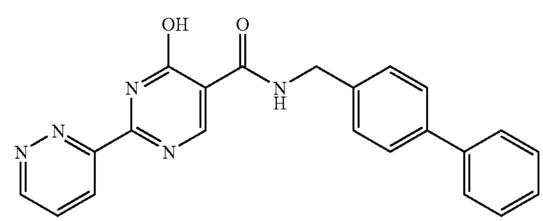 |
| Example 29 | 4-Hydroxy-2-(2-methyl-1,3-thiazol-4-yl)-N-[4-(trifluoromethyl)benzyl]pyrimidine-5-carboxamide | 395.0 2.89 | 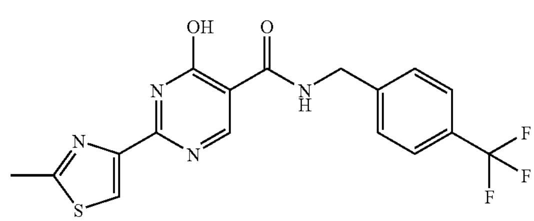 |

TABLE 2-continued

| Example | Name | HPLC/MS m/z (M + 1) R$_t$ (min) | Structure |
|---|---|---|---|
| Example 30 | N-(biphenyl-4-ylmethyl)-4-hydroxy-2-(2-methyl-1,3-thiazol-4-yl)pyrimidine-5-carboxamide | 403.0<br>3.12 | 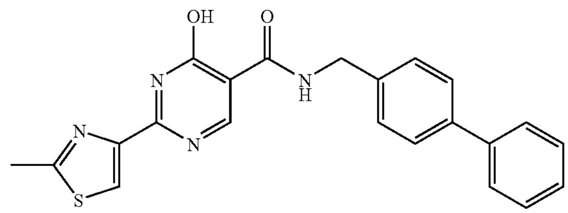 |
| Example 31 | 4-Hydroxy-2-(2-methyl-1,3-thiazol-4-yl)-N-[4-(trifluoromethoxy)benzyl]pyrimidine-5-carboxamide | 411.0<br>2.96 | 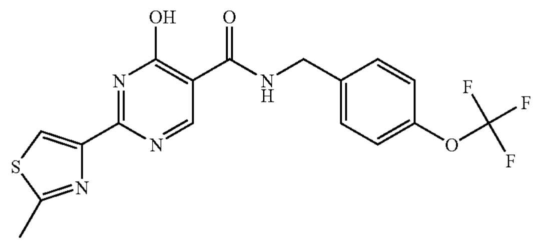 |
| Example 32 | N-[2-(4-fluorophenyl)ethyl]-4-hydroxy-2-(2-methyl-1,3-thiazol-4-yl)pyrimidine-5-carboxamide | 359.1<br>2.69 | 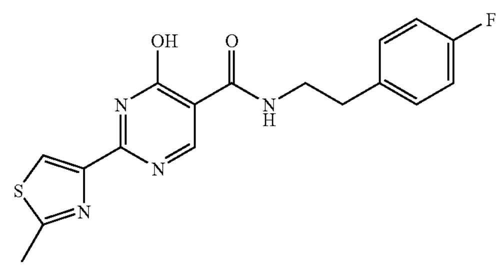 |
| Example 33 | 4-Hydroxy-N-(1-methyl-1-phenylethyl)-2-(2-methyl-1,3-thiazol-4-yl)pyrimidine-5-carboxamide | 355.1<br>2.75 | 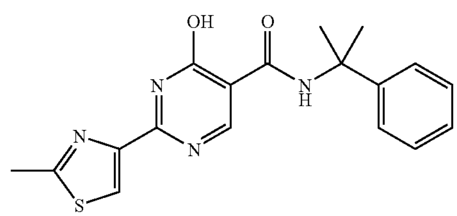 |
| Example 34 | 4-Hydroxy-2-(2-methyl-1,3-thiazol-4-yl)-N-[4-(trifluoromethyl)phenyl]pyrimidine-5-carboxamide | 381.0<br>3.08 | 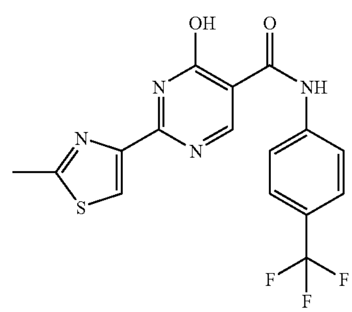 |
| Example 35 | 4-Hydroxy-2-(2-methyl-1,3-thiazol-4-yl)-N-[(1S)-1-phenylpropyl]pyrimidine-5-carboxamide | 355.1<br>2.81 | 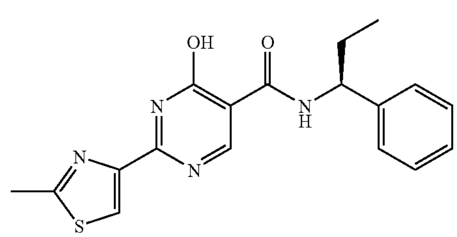 |

TABLE 2-continued

| Example | Name | HPLC/MS m/z (M + 1) R_t (min) | Structure |
|---|---|---|---|
| Example 36 | 4-Hydroxy-2-(2-methyl-1,3-thiazol-4-yl)-N-[(1R)-1-phenylpropyl]pyrimidine-5-carboxamide | 355.1 2.84 | 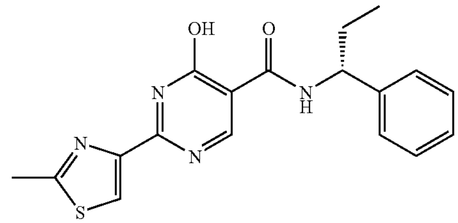 |
| Example 37 | N-(2,4-dichlorobenzyl)-4-hydroxy-2-(2-methyl-1,3-thiazol-4-yl)pyrimidine-5-carboxamide | 395.0 2.99 | 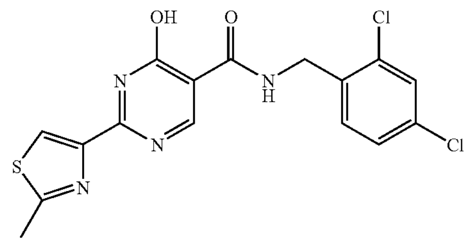 |
| Example 38 | N-(2-chloro-4-fluorophenyl)-4-hydroxy-2-(2-methyl-1,3-thiazol-4-yl)pyrimidine-5-carboxamide | 365.0 2.94 | 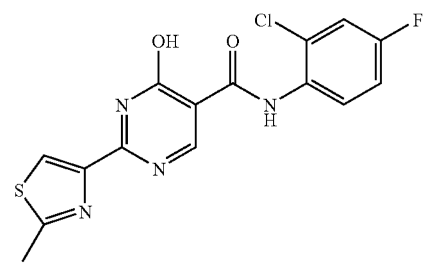 |
| Example 39 | N-(diphenylmethyl)-4-hydroxy-2-(2-methyl-1,3-thiazol-4-yl)pyrimidine-5-carboxamide | 403.1 3.06 | 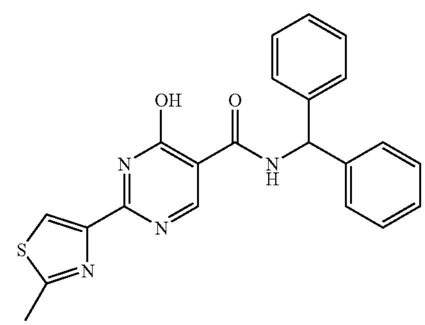 |
| Example 40 | N-(tert-butyl)-4-hydroxy-2-(2-methyl-1,3-thiazol-4-yl)pyrimidine-5-carboxamide | 293.1 2.38 | 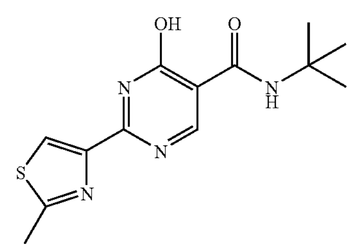 |
| Example 41 | 4-Hydroxy-2-(4-methyl-1,3-thiazol-2-yl)-N-[(1S)-1-phenylpropyl]pyrimidine-5-carboxamide | 355.1 2.92 | 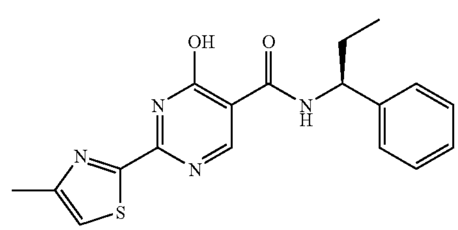 |

TABLE 2-continued

| Example | Name | HPLC/MS m/z (M + 1) R$_t$ (min) | Structure |
| --- | --- | --- | --- |
| Example 42 | N-(biphenyl-3-ylmethyl)-4-hydroxy-2-(2-methyl-1,3-thiazol-4-yl)pyrimidine-5-carboxamide | 403.1 3.12 | 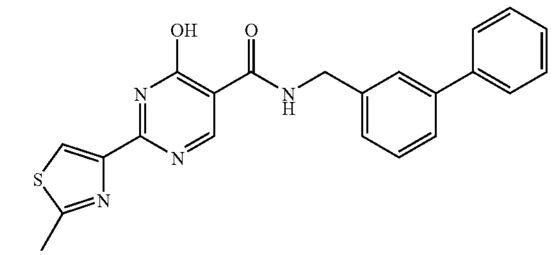 |
| Example 43 | 4-Hydroxy-N-(1-methyl-1-phenylethyl)-2-(1,3-thiazol-4-yl)pyrimidine-5-carboxamide | 341.2 2.55 | 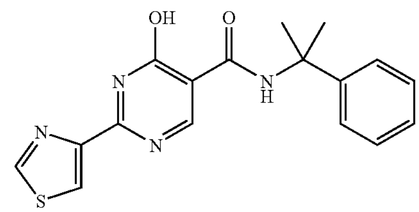 |
| Example 44 | 2-(3,5-Dimethyl-1H-pyrazol-1-yl)-4-hydroxy-N-[4-(trifluoromethoxy)benzyl]pyrimidine-5-carboxamide | 408.1 3.20 | 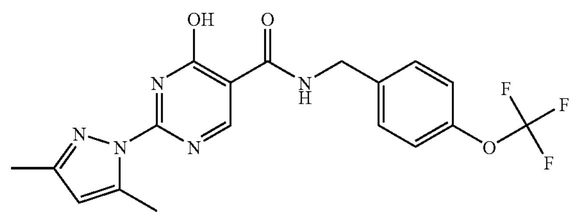 |
| Example 45 | N-(diphenylmethyl)-4-hydroxy-2-(1H-pyrrol-2-yl)pyrimidine-5-carboxamide | 371.1 2.94 | 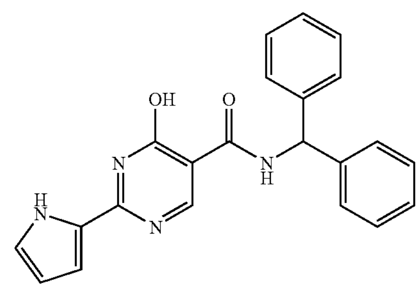 |
| Example 46 | N-(diphenylmethyl)-4-hydroxy-2-(1H-1,2,4-triazol-1-yl)pyrimidine-5-carboxamide | 373.1 2.73 | 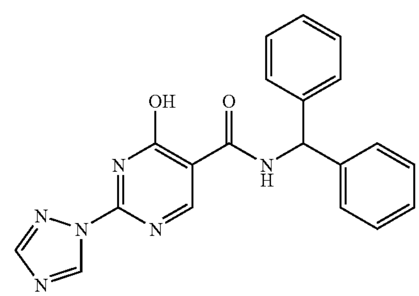 |
| Example 47 | 4-Hydroxy-N-(1-methyl-1-phenylethyl)-2-(1-methyl-1H-pyrazol-3-yl)pyrimidine-5-carboxamide | 338.1 2.53 | 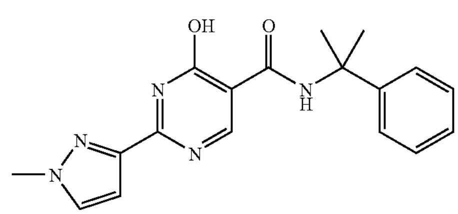 |

TABLE 2-continued

| Example | Name | HPLC/MS m/z (M + 1) R$_t$ (min) | Structure |
|---|---|---|---|
| Example 48 | 4-Hydroxy-N-[(1S)-1-phenylpropyl]-2-(1H-pyrazol-1-yl)pyrimidine-5-carboxamide | 324.2 2.68 | 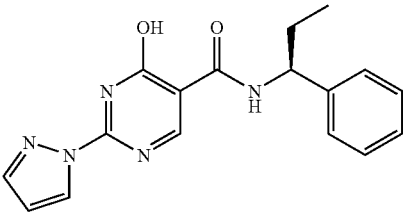 |
| Example 49 | N-(biphenyl-4-ylmethyl)-4-hydroxy-2-(1H-pyrazol-1-yl)pyrimidine-5-carboxamide | 372.1 3.01 | 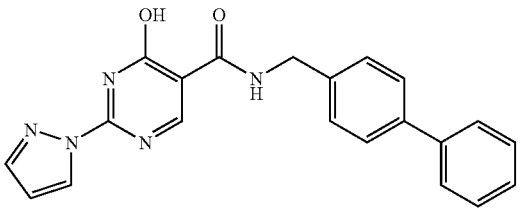 |
| Example 50 | 4-Hydroxy-2-(1H-pyrazol-1-yl)-N-[4-(trifluoromethoxy)benzyl]pyrimidine-5-carboxamide | 380.1 2.87 | 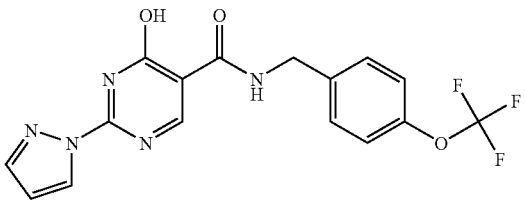 |
| Example 51 | N-(2,4-dichlorobenzyl)-4-hydroxy-2-(1H-pyrazol-1-yl)pyrimidine-5-carboxamide | 364.1 2.87 | 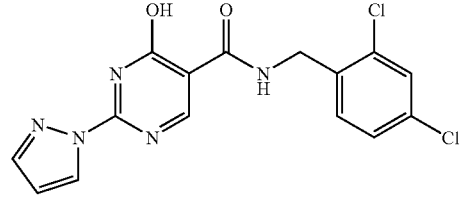 |
| Example 52 | N-(diphenylmethyl)-4-hydroxy-2-(1H-pyrazol-1-yl)pyrimidine-5-carboxamide | 372.2 2.93 | 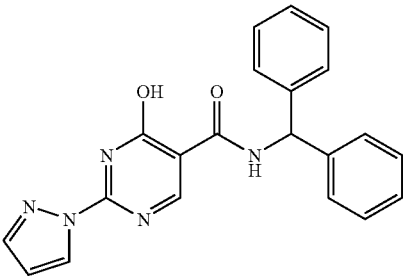 |
| Example 53 | N-(biphenyl-3-ylmethyl)-4-hydroxy-2-(1H-pyrazol-1-yl)pyrimidine-5-carboxamide | 372.2 2.99 | 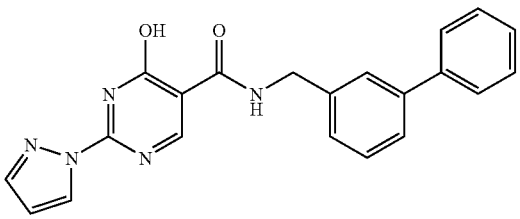 |

TABLE 2-continued

| Example | Name | HPLC/MS m/z (M + 1) R_t (min) | Structure |
|---|---|---|---|
| Example 54 | 4-Hydroxy-2-(1H-pyrazol-1-yl)-N-[4-(trifluoromethyl)benzyl]pynmidine-5-carboxamide | 364.0 2.79 | 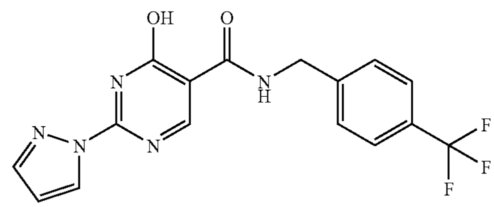 |
| Example 55 | N-(1,3-benzothiazol-2-ylmethyl)-4-hydroxy-2-(1H-pyrazol-1-yl)pyrimidine-5-carboxamide | 353.0 2.42 | 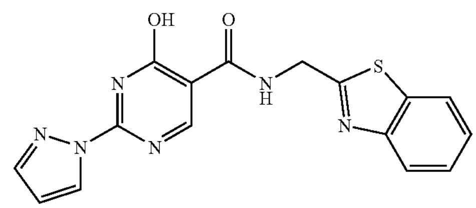 |
| Example 56 | 4-Hydroxy-N-(1-naphthylmethyl)-2-(1H-pyrazol-1-yl)pyrimidine-5-carboxamide | 346.1 2.78 | 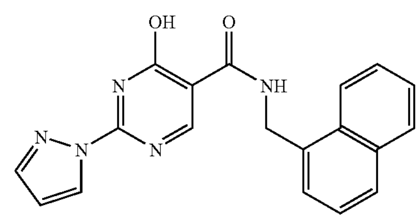 |
| Example 57 | N-(2,3-dihydro-1H-inden-1-yl)-4-hydroxy-2-(1H-pyrazol-1-yl)pyrimidine-5-carboxamide | 322.2 2.62 | 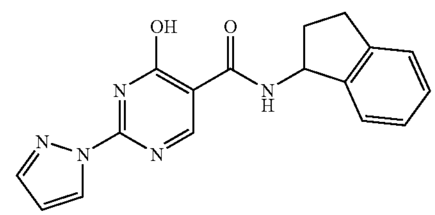 |
| Example 58 | 4-Hydroxy-N-[phenyl(pyridin-4-yl)methyl]-2-(1H-pyrazol-1-yl)pyrimidine-5-carboxamide | 373.2 1.85 | 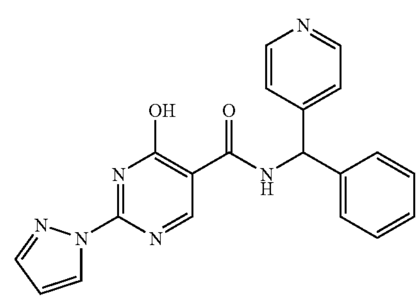 |
| Example 59 | N-[(6-chloropyridin-3-yl)methyl]-4-hydroxy-2-(1H-pyrazol-1-yl)pyrimidine-5-carboxamide | 331.2 2.01 | 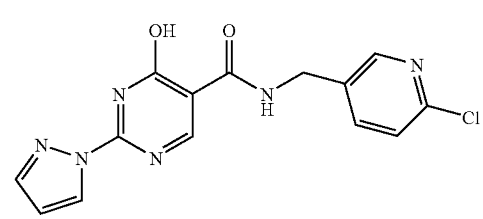 |

TABLE 2-continued

| Example | Name | HPLC/MS m/z (M + 1) R_t (min) | Structure |
|---|---|---|---|
| Example 60 | 4-Hydroxy-N-[(1S)-1-phenylethyl]-2-(1H-pyrazol-1-yl)pyrimidine-5-carboxamide | 310.1 2.47 | 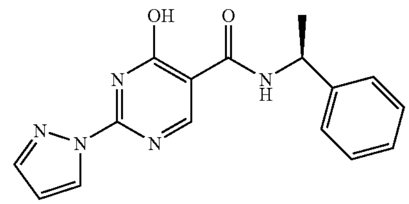 |
| Example 61 | 4-hydroxy-N-[(1R)-1-phenylethyl]-2-(1H-pyrazol-1-yl)pyrimidine-5-carboxamide | 310.1 2.50 | 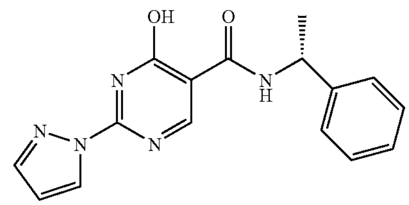 |
| Example 62 | N-[(2'-chlorobiphenyl-4-yl)methyl]-4-hydroxy-2-(1H-pyrazol-1-yl)pyrimidine-5-carboxamide | 406.2 3.14 | 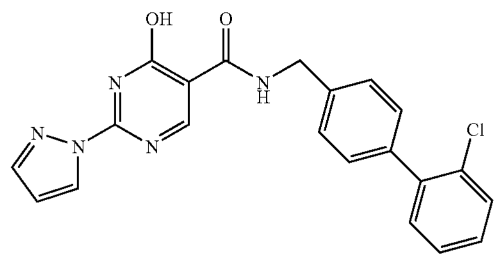 |
| Example 63 | N-[(4'-fluorobiphenyl-4-yl)methyl]-4-hydroxy-2-(1H-pyrazol-1-yl)pyrimidine-5-carboxamide | 390.1 3.05 | 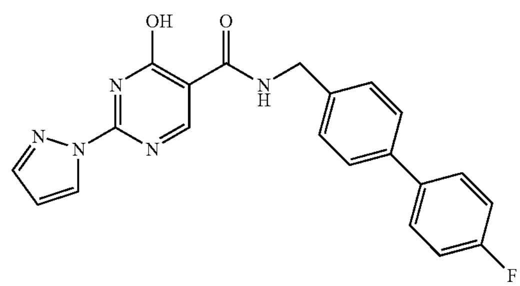 |
| Example 64 | N-[(5-chloropyrazin-2-yl)methyl]-4-hydroxy-2-(1H-pyrazol-1-yl)pyrimidine-5-carboxamide | 332.2 1.67 | 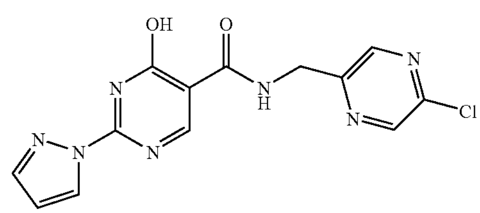 |
| Example 65 | N-[3,5-bis(trifluoromethyl)benzyl]-4-hydroxy-2-(1H-pyrazol-1-yl)pyrimidine-5-carboxamide | 431.9 3.07 | 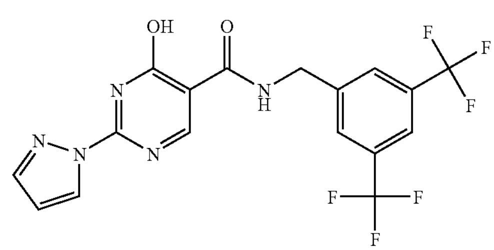 |

TABLE 2-continued

| Example | Name | HPLC/MS m/z (M + 1) R$_t$ (min) | Structure |
|---|---|---|---|
| Example 66 | 4-Hydroxy-N-[(5-methylpyrazin-2-yl)methyl]-2-(1H-pyrazol-1-yl)pyrimidine-5-carboxamide | 312.1<br>1.55 | 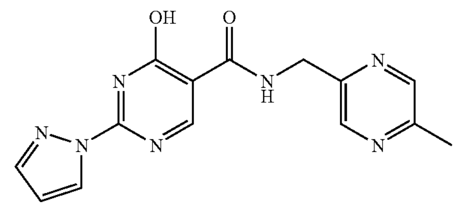 |
| Example 67 | N-(1,2-diphenylethyl)-4-hydroxy-2-(1H-pyrazol-1-yl)pyrimidine-5-carboxamide | 386.1<br>2.98 | 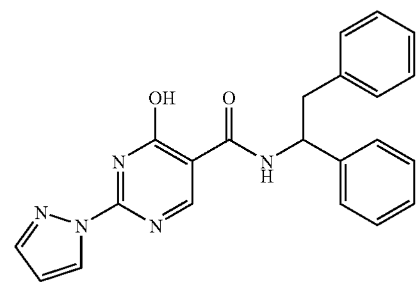 |
| Example 68 | N-[2-fluoro-4-(trifluoromethyl)benzyl]-4-hydroxy-2-(1H-pyrazol-1-yl)pyrimidine-5-carboxamide | 382.0<br>2.82 | 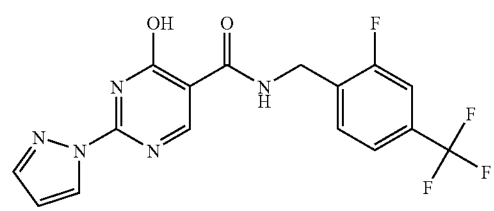 |
| Example 69 | N-(cyclopropylmethyl)-4-hydroxy-2-(1H-pyrazol-1-yl)pyrimidine-5-carboxamide | 260.2<br>1.80 | 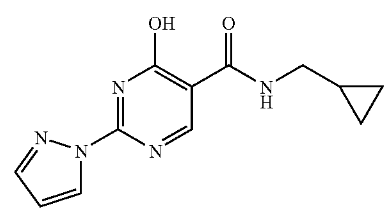 |
| Example 70 | N-[1-(4-fluorophenyl)ethyl]-4-hydroxy-2-(1H-pyrazol-1-yl)pyrimidine-5-carboxamide (Racemic) | 328.3<br>2.56 | 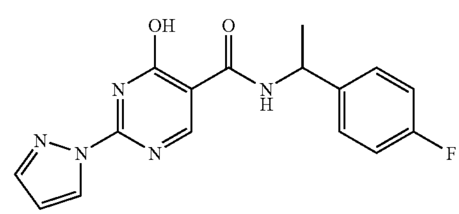 |
| Example 71 | N-[(1S)-1-(4-fluorophenyl)ethyl]-4-hydroxy-2-(1H-pyrazol-1-yl)pyrimidine-5-carboxamide | 328.1<br>2.56 | 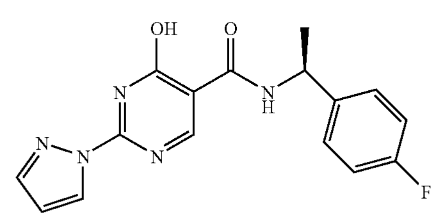 |

TABLE 2-continued

| Example | Name | HPLC/MS m/z (M + 1) R_t (min) | Structure |
|---|---|---|---|
| Example 72 | N-[(1R)-1-(4-fluorophenyl)ethyl]-4-hydroxy-2-(1H-pyrazol-1-yl)pyrimidine-5-carboxamide | 328.1 2.56 | 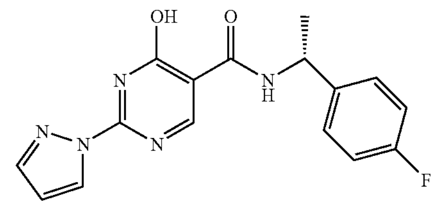 |
| Example 73 | N-[1-(4-fluorophenyl)-1-methylethyl]-4-hydroxy-2-(1H-pyrazol-1-yl)pyrimidine-5-carboxamide | 342.1 2.66 | 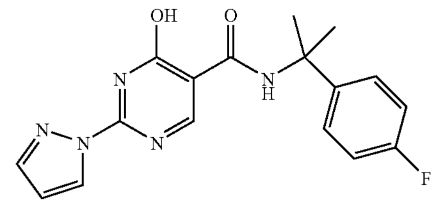 |
| Example 74 | 4-Hydroxy-N-{1-methyl-1-[6-(trifluoromethyl)pyridin-3-yl]ethyl}-2-(1H-pyrazol-1-yl)pyrimidine-5-carboxamide | 393.0 2.57 | 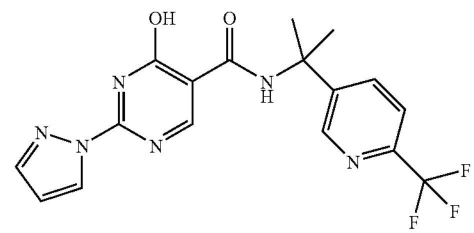 |
| Example 75 | N-(4-chlorobenzyl)-4-hydroxy-2-(1H-pyrazol-1-yl)pyrimidine-5-carboxamide | 330.0 2.63 | 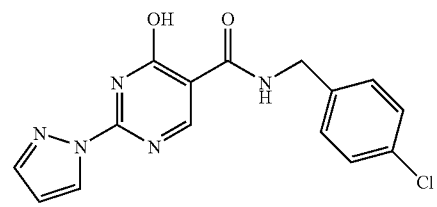 |
| Example 76 | N'-Ethyl-4-hydroxy-N'-phenyl-2-(1H-pyrazol-1-yl)pyrimidine-5-carbohydrazide trifluoroacetate (salt) | 325.1 2.44 | 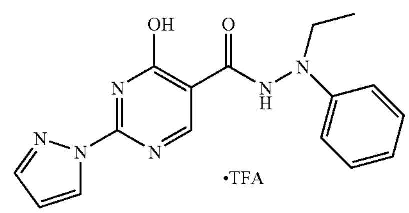 |
| Example 77 | 4-Hydroxy-N-(4-methylbenzyl)-2-(1H-pyrazol-1-yl)pyrimidine-5-carboxamide | 310.2 2.58 | 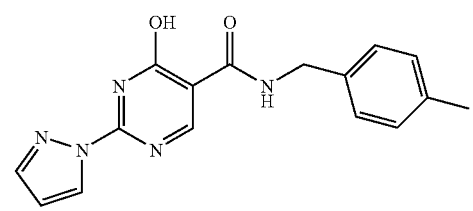 |
| Example 78 | 4-Hydroxy-N-[(1R)-1-(4-methylphenyl)ethyl]-2-(1H-pyrazol-1-yl)pyrimidine-5-carboxamide | 324.1 2.70 | 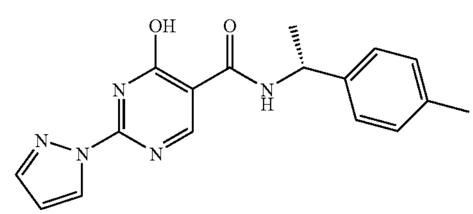 |

TABLE 2-continued

| Example | Name | HPLC/MS m/z (M + 1) R<sub>t</sub> (min) | Structure |
|---|---|---|---|
| Example 79 | 4-Hydroxy-N-[(1S)-1-(4-methylphenyl)ethyl]-2-(1H-pyrazol-1-yl)pyrimidine-5-carboxamide | 324.1 2.71 | 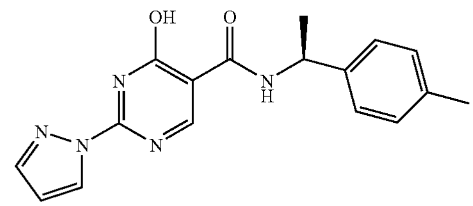 |
| Example 80 | 4-hydroxy-N-piperidin-1-yl-2-(1H-pyrazol-1-yl)pyrimidine-5-carboxamide trifluoroacetate (salt) | 289.1 1.33 | 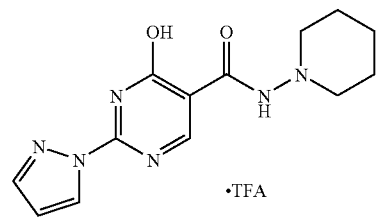 |
| Example 81 | 5-(Piperidin-1-ylcarbonyl)-2-(1H-pyrazol-1-yl)pyrimidin-4-ol | 274.1 1.53 | 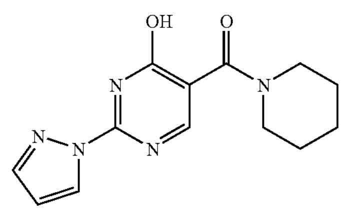 |
| Example 82 | N-(4-tert-butylcyclohexyl)-4-hydroxy-2-(1H-pyrazol-1-yl)pyrimidine-5-carboxamide | 344.1 3.22 | 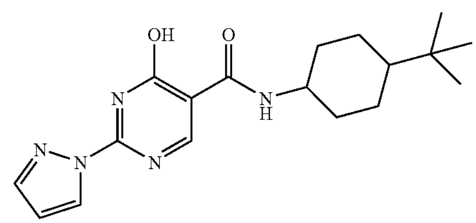 |
| Example 83 | 4-Hydroxy-N-[(4R)-3-oxoisoxazolidin-4-yl]-2-(1H-pyrazol-1-yl)pyrimidine-5-carboxamide | 291.1 0.57 | 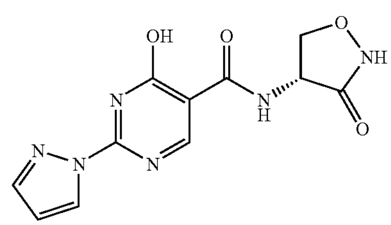 |
| Example 84 | N-[(1R)-1-cyclohexylethyl]-4-hydroxy-2-(1H-pyrazol-1-yl)pyrimidine-5-carboxamide | 316.1 2.86 | 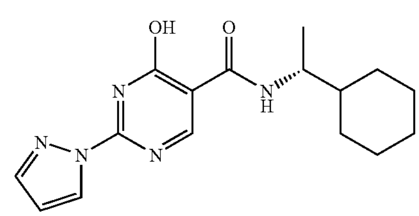 |
| Example 85 | N-[(1S)-1-cyclohexylethyl]-4-hydroxy-2-(1H-pyrazol-1-yl)pyrimidine-5-carboxamide | 316.1 2.85 | 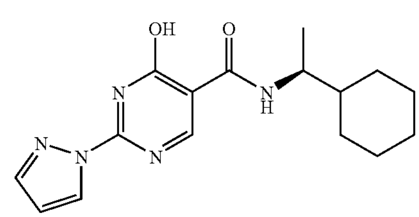 |

TABLE 2-continued

| Example | Name | HPLC/MS m/z (M + 1) R$_t$ (min) | Structure |
|---|---|---|---|
| Example 86 | 4-hydroxy-2-(1H-pyrazol-1-yl)-N-(1-pyridin-4-ylethyl)pyrimidine-5-carboxamide trifluoroacetate (salt) | 309.2<br>0.62 | 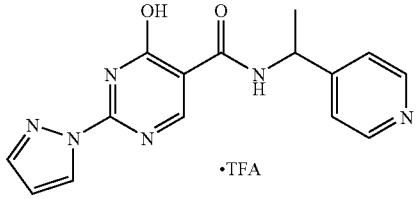 |
| Example 87 | 4-Hydroxy-N-(1-phenylcyclopropyl)-2-(1H-pyrazol-1-yl)pyrimidine-5-carboxamide | 322.0<br>2.45 | 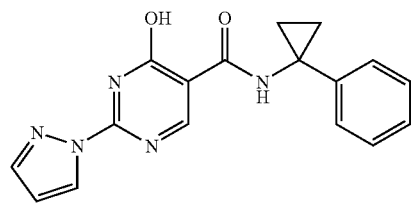 |
| Example 88 | 4-hydroxy-N,N'-diphenyl-2-(1H-pyrazol-1-yl)pyrimidine-5-carbohydrazide trifluoroacetate (salt) | 373.1<br>2.88 | 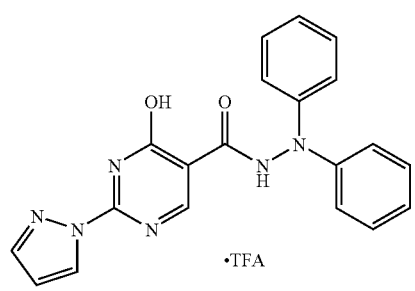 |
| Example 89 | N-[1-(3,4-difluorophenyl)-1-methylethyl]-4-hydroxy-2-(1H-pyrazol-1-yl)pyrimidine-5-carboxamide | 360.0<br>2.74 | 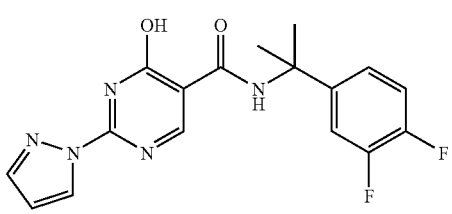 |
| Example 90 | N-{(1R)-1-[(3S,5S,7S)-1-adamantyl]ethyl}-4-hydroxy-2-(1H-pyrazol-1-yl)pyrimidine-5-carboxamide | 368.1<br>3.21 | 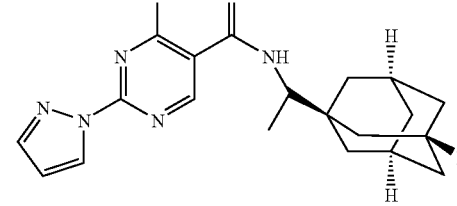 |
| Example 91 | N-[(1S)-1-(4-bromophenyl)ethyl]-4-hydroxy-2-(1H-pyrazol-1-yl)pyrimidine-5-carboxamide | 389.8<br>2.83 | 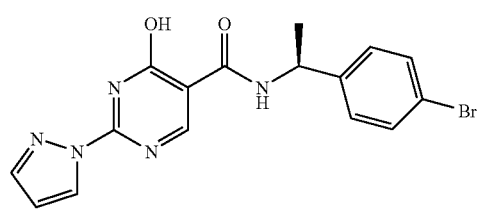 |

TABLE 2-continued

| Example | Name | HPLC/MS m/z (M + 1) R$_t$ (min) | Structure |
|---|---|---|---|
| Example 92 | N-[1-(4-bromophenyl)-1-methylethyl]-4-hydroxy-2-(1H-pyrazol-1-yl)pyrimidine-5-carboxamide | 401.9 (M + 1), 403.9 (M + 3), 2.91 | 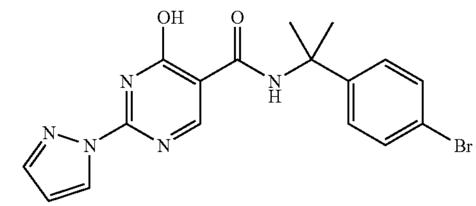 |
| Example 93 | 4-hydroxy-N-(4-phenoxybenzyl)-2-(1H-pyrazol-1-yl)pyrimidine-5-carboxamide | 388.0, 3.15 | 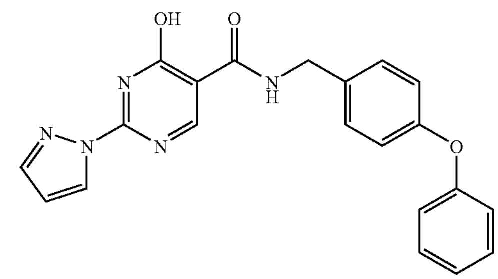 |
| Example 94 | 4-hydroxy-N-(1-phenylcyclohexyl)-2-(1H-pyrazol-1-yl)pyrimidine-5-carboxamide | 364.0, 3.17 | 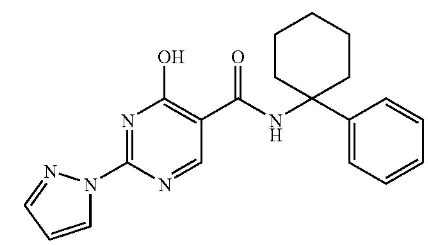 |
| Example 95 | N-(4-benzoylbenzyl)-4-hydroxy-2-(1H-pyrazol-1-yl)pyrimidine-5-carboxamide | 400.0, 2.90 | 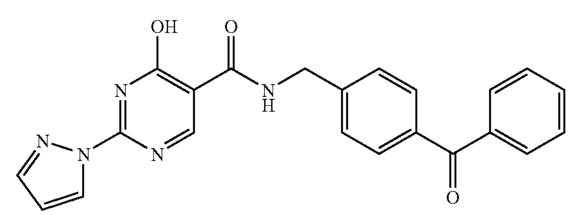 |
| Example 96 | N-[bis(4-methoxyphenyl)methyl]-4-hydroxy-2-(1H-pyrazol-1-yl)pyrimidine-5-carboxamide | 431.9, 3.07 | 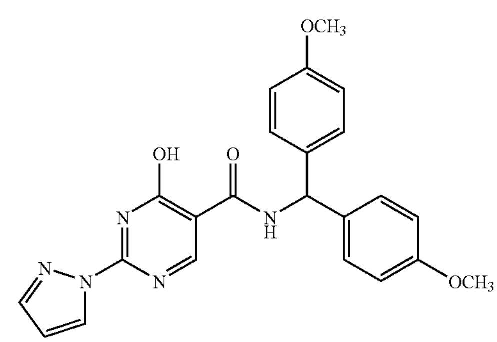 |

TABLE 2-continued

| Example | Name | HPLC/MS m/z (M + 1) R$_t$ (min) | Structure |
|---|---|---|---|
| Example 97 | 4-hydroxy-N-[4-(4-methylphenoxy)benzyl]-2-(1H-pyrazol-1-yl)pyrimidine-5-carboxamide | 402.0, 3.34 | 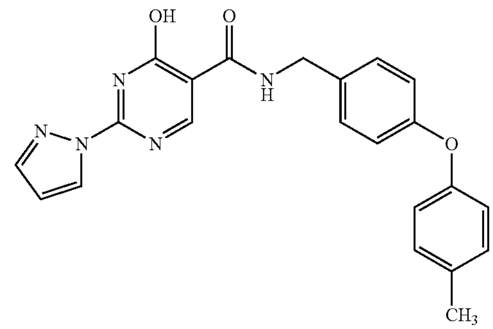 |
| Example 98 | N-(1-ethyl-1-phenylpropyl)-4-hydroxy-2-(1H-pyrazol-1-yl)pyrimidine-5-carboxamide | 352.0, 3.15 | 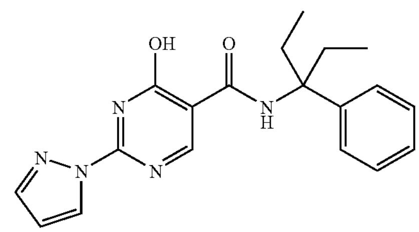 |
| Example 99 | N-[4-(4-fluorophenoxy)benzyl]-4-hydroxy-2-(1H-pyrazol-1-yl)pyrimidine-5-carboxamide | 406.0 3.20 | 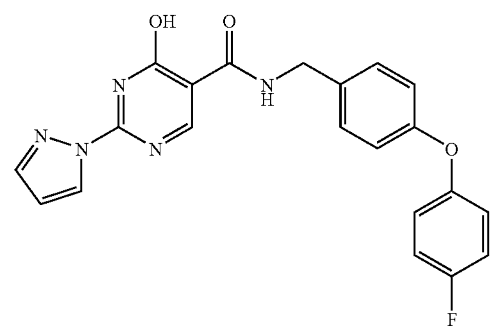 |
| Example 100 | 4-hydroxy-N-[4-(2-methylphenoxy)benzyl]-2-(1H-pyrazol-1-yl)pyrimidine-5-carboxamide | 402.0, 3.32 | 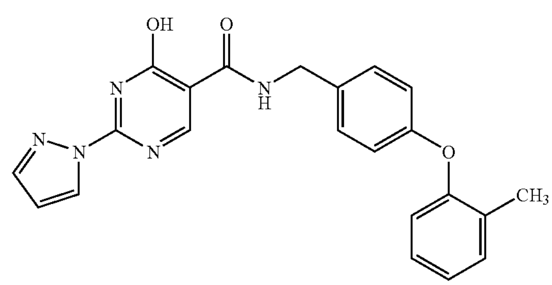 |
| Example 101 | N-(2,3-dihydro-1-benzofuran-5-ylmethyl)-4-hydroxy-2-(1H-pyrazol-1-yl)pyrimidine-5-carboxamide | 338.1 2.48 | 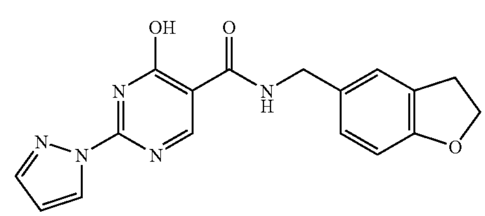 |

TABLE 2-continued

| Example | Name | HPLC/MS m/z (M + 1) $R_t$ (min) | Structure |
|---|---|---|---|
| Example 102 | N-9H-fluoren-9-yl-4-hydroxy-2-(1H-pyrazol-1-yl)pyrimidine-5-carboxamide | 370.1<br>3.15 | 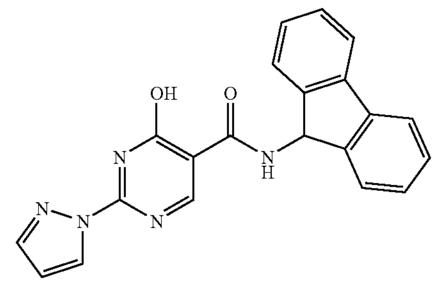 |
| Example 103 | methyl 4-[({[4-hydroxy-2-(1H-pyrazol-1-yl)pyrimidin-5-yl]carbonyl}amino)methyl]benzoate | 354.0<br>2.50 | 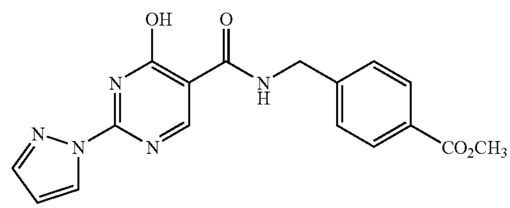 |

EXAMPLE 104

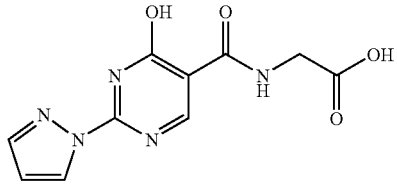

N-{[4-hydroxy-2-(1H-pyrazol-1-yl)pyrimidin-5-yl]carbonyl}glycine

Tert-butyl N-{[4-hydroxy-2-(1H-pyrazol-1-yl)pyrimidin-5-yl]carbonyl}glycinate (140 mg, 0.44 mmol, prepared in similar fashion to that of the preceding examples) was dissolved in DCM (1 mL) and TFA (1 mL) was added. The reaction was stirred at rt for 4 h, concentrated and partially dissolved in EtOAc and hexane was added to precipitate the desired compound. The product was isolated affording the title compound. HPLC/MS: 264.0 (M+1); $R_t$=0.65 min.

EXAMPLE 105

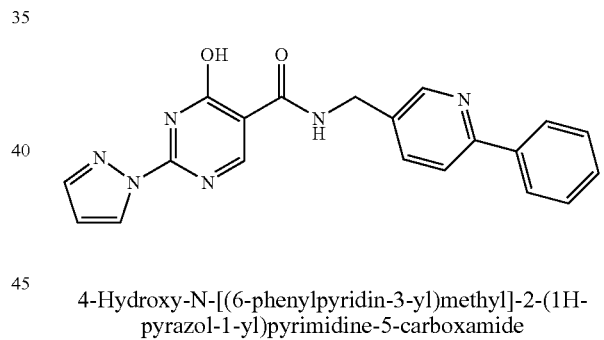

4-Hydroxy-N-[(6-phenylpyridin-3-yl)methyl]-2-(1H-pyrazol-1-yl)pyrimidine-5-carboxamide The product of Example 59 (200 mg, 0.61 mmol) was dissolved in DME (3.6 mL), water (0.32 mL) and isopropanol (2.7 mL). An aq solution of $Na_2CO_3$ (2 M, 0.9 mL, 1.81 mmol), phenylboronic acid (133 mg, 1.1 mmol) and tetrakis(triphenylphosphine)palladium(0) (34 mg, 0.048 mmol) were added and the flask was evacuated and backfilled with nitrogen 3 times. The mixture was heated at 90° C. for 1 h and DMA (2 mL) was added. The reaction was heated an additional 2 h, cooled, diluted with EtOAc and washed with acidic brine to bring pH to around 4. The organic layer was dried ($Na_2SO_4$), filtered and concentrated. The residue was partially dissolved in acetone and MeOH and hexane was added to precipitate the desired compound. The residue was isolated and further rinsed with MeOH affording the title compound. HPLC/MS: 373.1 (M+1); $R_t$=1.78 min.

Using the general Suzuki coupling procedure described in Example 105, the appropriate starting material and boronic acid, compounds of Examples 106 through 109 were obtained as shown in Table 3. Reverse phase purification was required for Example 107 affording the TFA salt.

TABLE 3

| | | | |
|---|---|---|---|
| Example 106 | N-{[6-(2-fluorophenyl)pyridin-3-yl]methyl}-4-hydroxy-2-(1H-pyrazol-1-yl)pyrimidine-5-carboxamide | 391.1<br>2.05 | 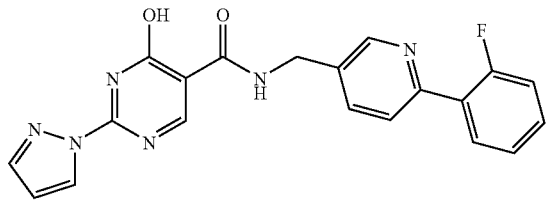 |
| Example 107 | N-{[6-(3-fluorophenyl)pyridin-3-yl]methyl}-4-hydroxy-2-(1H-pyrazol-1-yl)pyrimidine-5-carboxamide trifluoroacetate (salt) | 391.1<br>2.17 | 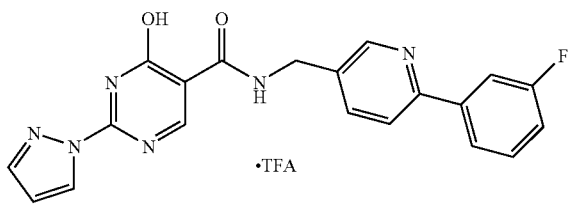 |
| Example 108 | N-{[6-(4-fluorophenyl)pyridin-3-yl]methyl}-4-hydroxy-2-(1H-pyrazol-1-yl)pyrimidine-5-carboxamide | 391.1<br>2.00 | 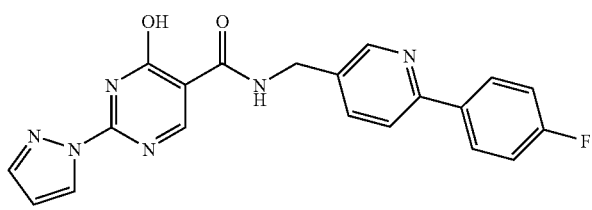 |
| Example 109 | N-{[5-(4-fluorophenyl)pyrazin-2-yl]methyl}-4-hydroxy-2-(1H-pyrazol-1-yl)pyrimidine-5-carboxamide | 392.0<br>2.61 | 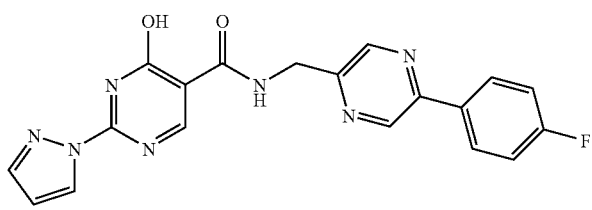 |

EXAMPLE 110

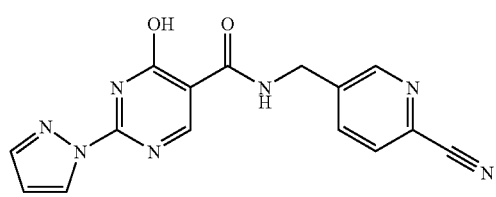

N-[(6-cyanopyridin-3-yl)methyl]-4-hydroxy-2-(1H-pyrazol-1-yl)pyrimidine-5-carboxamide The product of Example 59 (150 mg, 0.45 mmol) was dissolved in DMF (5 mL). Zn(CN)$_2$ (53 mg, 0.45 mmol), Pd$_2$(dba)$_3$ (21 mg, 0.023 mmol), and dppf (33 mg, 0.06 mmol) were added and the flask was evacuated and backfilled with nitrogen 3 times. The mixture was heated at 110° C. overnight. The reaction was cooled and partitioned between DCM and HCl (2M) and the organic layer was dried (Na$_2$SO$_4$), filtered and concentrated. The residue was purified on a reverse phase C-18 column eluting with 0 to 70% MeCN/water. Concentration of desired fractions afforded the title compound. HPLC/MS: 322.0 (M+1); R$_t$=1.76 min.

EXAMPLE 111

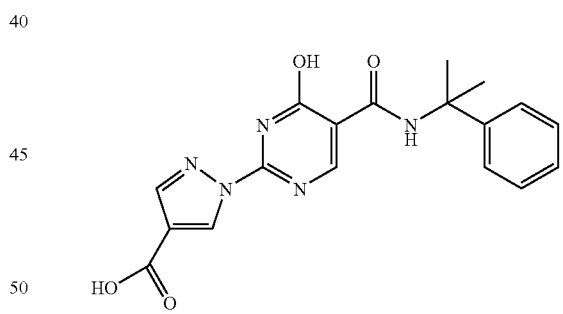

1-(4-Hydroxy-5-{[(1-methyl-1-phenylethyl)amino]carbonyl}pyrimidin-2-yl)-1H-pyrazole-4-carboxylic acid Step A: 4-Hydroxy-2-(4-iodo-1H-pyrazol-1-yl)-N-(1-methyl-1-phenylethyl)pyrimidine-5-carboxamide The product of Example 112 (0.75 g, 2.32 mmol) was dissolved in MeCN (30 mL) and I$_2$ (0.38 g, 1.5 mmol) and CAN (1.78 g, 3.25 mmol) were added and the reaction was heated at 85° C. for 6 h. The solution was cooled, diluted with EtOAc and washed with water containing a few chunks of sodium thiosulfate. The organic layer was washed with NaHSO$_4$ (5% aq.) and brine, the solution was dried (Na$_2$SO$_4$), filtered and concentrated affording the title product which was used without further purification.

Step B: 1-(4-Hydroxy-5-{[(1-methyl-1-phenylethyl)amino]carbonyl}pyrimidin-2-yl)-1H-pyrazole-4-carboxylic acid The crude product of Step A (0.675 g, 1.5 mmol) was dissolved in DMSO (15 mL) and dppf (166 mg, 0.3 mmol) and Pd(OAc)$_2$ (17 mg, 0.075 mmol) were added. The reaction mixture was purged, backfilled with carbon monoxide 3 times, and stirred under a carbon monoxide balloon at 80° C. for 4 h. The reaction was diluted with EtOAc, washed with acidic water, dried (Na$_2$SO$_4$), filtered and concentrated. The residue was purified on a reverse phase C-18 column eluting with 0 to 90% MeCN/water. The desired fractions were concentrated and partially dissolved in EtOAc and hexane was added to precipitate the desired compound. The product was isolated affording the title compound. HPLC/MS: 368.0 (M+1); R$_t$=2.49 min.

INTERMEDIATE 12

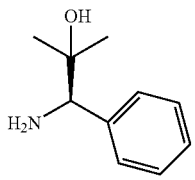

(1R)-1-Amino-2-methyl-1-phenylpropan-2-ol

Step A: Methyl (2R)-phenyl[(trifluoroacetyl)amino]acetate. Methyl (2R)-amino(phenyl)acetate hydrochloride (2.10 g, 10.4 mmol) was dissolved in EtOAc and extracted with brine, containing NaHCO$_3$. The organic layer was isolated and dried with Na$_2$SO$_4$, filtered and concentrated. The free base methyl ester was dissolved in THF (20 mL) and cooled to −78° C. NEt$_3$ (1.7 mL, 12.5 mmol) and trifluoroacetic anhydride (1.8 mL, 12.5 mmol) were added and the reaction was aged for 3 h while allowing it to come to rt. EtOAc was added and the mixture was washed with acidic brine. The organic layer was collected and washed with NaHCO$_3$ (sat), dried with Na$_2$SO$_4$, filtered and concentrated. The residue was purified by flash chromatography on silica gel gradient eluted with 0-15% EtOAc/hexane affording the title compound. HPLC/MS: 262.0 (M+1); R$_t$=2.83 min.

Step B: 2,2,2-Trifluoro-N-[(1R)-2-hydroxy-2-methyl-1-phenylpropyl]acetamide. The product of Step A (2.04 g, 7.81 mmol) was dissolved in THF (10 mL) and methylmagnesium bromide (13.95 mL, 19.53 mmol, 1.4 M in THF) was added at rt. The reaction was stirred at rt for 2.5 h, concentrated and dissolved in EtOAc and washed with 2M HCl (aq). The organic layer was collected, dried with Na$_2$SO$_4$, filtered and concentrated. The residue was purified by flash chromatography on silica gel gradient eluted with 0-15% EtOAc/hexane affording the title compound. HPLC/MS: 262.1 (M+1); R$_t$=2.71 min.

Step C: (1R)-1-Amino-2-methyl-1-phenylpropan-2-ol. The product from step B (1.07 g, 4.10 mmol) was dissolved in MeOH (5 mL) and KOH (0.460 g, 8.19 mmol, 1 mL MeOH) was added at rt. The reaction was stirred overnight, concentrated, diluted in EtOAc and washed with DI water. The organic layer was dried with Na$_2$SO$_4$, filtered and concentrated. The product was used as is. HPLC/MS: 166.2 (M+1); R$_t$=0.68 min.

INTERMEDIATE 13

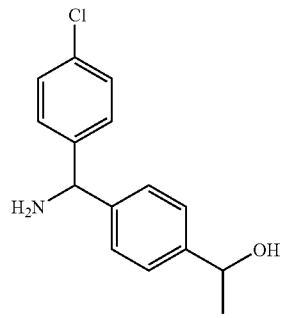

1-{4-[Amino(4-chlorophenyl)methyl]phenyl}ethanol

Step A: 4-(1-Hydroxyethyl)benzonitrile. 4-Acetylbenzonitrile (3 g, 20.67 mmol) was dissolved in THF (5 mL) and MeOH (5 mL) and cooled to 0° C. NaBH$_4$ (0.782 g, 20.67 mmol) was added slowly. The reaction aged at rt for 30 min and was concentrated. 2M aq HCl was added and the solution was extracted with EtOAc. The organic layer was washed with water, dried with Na$_2$SO$_4$, filtered and concentrated to provide the product.

Step B: 1-{4-[Amino(4-chlorophenyl)methyl]phenyl}ethanol. The product of Step A (1.47 g, 10 mmol) was dissolved in THF (20 mL), cooled in an ice-bath and 4-chlorophenylmagnesium bromide (21.00 mL, 21.00 mmol, 1 M in THF) was added. The reaction aged at 50° C. for 4 h and then cooled to rt overnight. The solvent had evaporated overnight and the product was taken up in 2-methyltetrhydrofuran (20 mL) and an additional 1 eq of 4-chlorophenylmagnesium bromide was added. The reaction aged at rt for 3 h and was concentrated. The reaction was diluted with 15 mL MeOH. NaBH (378 mg, 10.00 mmol) was added and the reaction aged for 1 h. The reaction was concentrated, diluted with 2M HCl (aq) and extracted with EtOAc. The organic layer was collected, dried with Na$_2$SO$_4$, filtered and concentrated. The residue was purified somewhat by flash chromatography on silica gel gradient eluted with 0-10% MeOH/EtOAc affording title compound. HPLC/MS: 244.9 (M—NH$_2$)$^+$; R$_t$=2.09 min

INTERMEDIATE 14

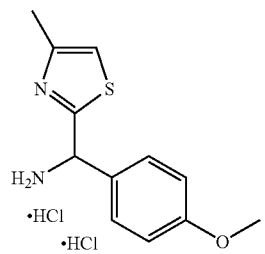

1-(4-methoxyphenyl)-1-(4-methyl-1,3-thiazol-2-yl)methanamine dihydrochloride Step A: (R)-2-Methyl-N-[(4-methyl-1,3-thiazol-2-yl)methylene]propane-2-sulfinamide A 3-necked RBF fitted with a reflux condenser, a nitrogen inlet, a thermometer and a mechanical stirrer was charged with 4-methyl-1,3-thiazole-2-carbaldehyde (25 g, 197 mmol) and (R)-(+)-2-methyl-2-propanesulfinamide (25 g, 206 mmol). The solids were dissolved in chloroform (0.5 L) and pyridinium-toluenesulfonate (2.5 g, 10 mmol), magnesium sulfate (47.3 g, 393 mmol) and copper(II)sulfate (62.8 g, 393 mmol) were added. The mixture was aged at reflux for about 7 h and then rt for 2 days. The reaction was filtered through a Solka Floc pad and concentrated under vacuum. The residue was purified by flash chromatography on silica gel gradient eluted with DCM and then 0-50% EtOAc in heptane affording the title-compound. HPLC/MS: 231.19 (M+1); $R_t$=2.58 min.

Step B: (R)-N-[(4-methoxyphenyl)(4-methyl-1,3-thiazol-2-yl)methyl]-2-methylpropane-2-sulfinamide. A 3-necked RBF fitted with a thermometer, a nitrogen inlet, an addition funnel and a magnetic stir-bar was charged with the product from step A (46 g, 200 mmol) and dissolved in toluene (1 L). The reaction was cooled in a dry ice/acetone bath to −68° C. and the solution became cloudy. Bromo(4-methoxyphenyl)magnesium (479 mL, 240 mmol, 0.5 M in THF) was added drop-wise to keep temperature below −65° C. The reaction was aged for 4 h at −65° C. and then allowed to come to rt overnight. The reaction was quenched with saturated aq NH$_4$Cl and extracted with EtOAc (2×). The organic layers were combined and washed with brine, dried with Na$_2$SO$_4$, filtered and concentrated. The resulting oil was purified by flash chromatography on silica gel gradient eluted with 50%-100% EtOAc/heptane, followed by 5%-15% acetone/EtOAc, affording a small portion of pure slow eluting diastereomer and a larger portion of mixed fast and slow eluting diasteromers. The mixed portion of diasteromers was re-purified by flash chromatography on silica gel gradient eluted with 50%-100% EtOAc/heptane, followed by 0%-10% MeOH/EtOAc affording a major portion of slow eluting diastereomer and a minor portion of fast eluting diastereomer. Slow eluting, Major isomer HPLC/MS: 339.3 (M+1); $R_t$=2.98 min. Fast eluting, Minor isomer HPLC/MS: 339.2 (M+1); $R_t$=2.96 min.

Step C: 1-(4-methoxyphenyl)-1-(4-methyl-1,3-thiazol-2-yl)methanamine dihydrochloride. The slow eluting diastereomer from step B (58.7 g, 173 mmol) was dissolved in DCM (600 mL). HCl in dioxane (4 M) was added slowly to keep temperature below 35° C. MeOH (110 mL) was added to keep product in solution and the reaction aged at rt for 2 h. The product was concentrated and re-dissolved in toluene and MeOH and concentrated. EtOAc was added and the solid was filtered and washed with EtOAc followed by heptane affording the title compound. HPLC/MS: 218.3 (M—NH$_2$)$^+$; $R_t$=2.06 min. The fast eluting diastereomer from Step B was treated as described above affording the title compound. HPLC/MS: 218.3 (M—NH$_2$)$^+$; $R_t$=2.06 min.

INTERMEDIATE 15

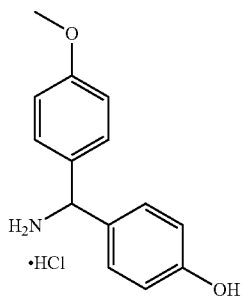

4-[amino(4-methoxyphenyl)methyl]phenol hydrochloride

Step A: (S)-N-[(4-hydroxyphenyl)methylidene]-2-methylpropane-2-sulfinamide To 4-hydroxybenzaldehyde (2.015 g, 16.5 mmol) and (S)-(−)-2-methyl-2-propanesulfinamide (2.00 g, 16.5 mmol) was added chloroform (70 mL), pyridinium-toluenesulfonate (0.207 g, 0.825 mmol), magnesium sulfate (9.93 g, 83 mmol) and copper(II)sulfate (5.27 g, 33 mmol). The mixture was heated to reflux for about 20 h and aged about 2 days at rt. The mixture was filtered through Celite® and concentrated under vacuum. The residue was purified by flash chromatography on silica gel gradient eluted with DCM and then 0-30% EtOAc in DCM affording the title compound. HPLC/MS: 226.1.1 (M+1); $R_t$=2.88 min.

Step B: (S)-N-[(4-hydroxypheyl)(4-methoxypheylmethyl]-2-methylpropane-2-sulfinamide. To the product from step A (2.05 g, 9.10 mmol) in toluene (80 mL) and THF (35 mL) at about 5° C. was added 4-methoxyphenylmagnesiumbromide (36 mL, 18.2 mmol, 0.5 M in THF) drop-wise. The reaction was aged for 40 min and the cooling bath was removed. The reaction aged an hour before an additional portion of 4-methoxyphenylmagnesiumbromide (6 mL, 3.0 mmol, 0.5 M in THF) was added. The reaction aged about 2 h, was partially concentrated, quenched with saturated aq NH$_4$Cl and extracted with EtOAc twice. The combined organic portions were concentrated. The residue was purified by flash chromatography on silica gel gradient eluted with 0-90% EtOAc in DCM to afford the product which was the major isomer. Major Isomer HPLC/MS: 334.1 (M+1); $R_t$=3.01 min. Minor Isomer HPLC/MS: 334.1 (M+1); $R_t$=3.17 min.

Step C: 4-[amino(4-methoxyphenyl)methyl]phenol hydrochloride. The major isomer of step B (1.00 g, 3.00 mmol) was combined with DCM (12 mL), MeOH (12 mL) and HCl in diethyl ether (2.25 mL, 4.50 mmol, 2 M). The reaction aged at rt for 2.5 h and was concentrated. The solid were washed with diethyl ether to afford the title compound. HPLC/MS: 213.1 (M—NH$_2$)$^+$; $R_t$=2.04 min.

INTERMEDIATE 16

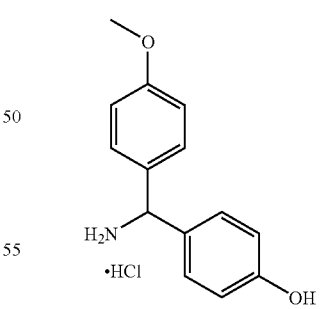

4-[amino(4-methoxyphenyl)methyl]phenol hydrochloride

The title compound was prepared in similar fashion to Intermediate 15 except using (R)-(+)-2-methyl-2-propanesulfinamide instead of (S)-(−)-2-methyl-2-propanesulfinamide in Step A. HPLC/MS: 213.1 (M—NH$_2$)$^+$; $R_t$=2.04 min.

INTERMEDIATE 17

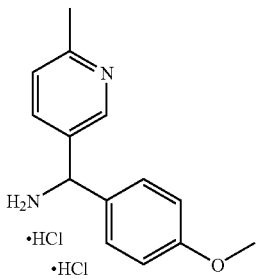

5-[Ammonio(4-methoxyphenyl)methyl]-2-methylpyridinium dichloride

Using a procedure similar to that described for Intermediate 14 and appropriate starting materials, replacing (R)-(+)-2-methyl-2-propanesulfinamide with (S)-(−)-2-methyl-2-propanesulfinamide afforded the fast eluting diastereomer and the slow eluting diastereomer. The separated diastereomers were treated individually to HCl as above affording the title compound. HPLC/MS: 229.1 (M+1); $R_t$=0.72 min.

INTERMEDIATE 18

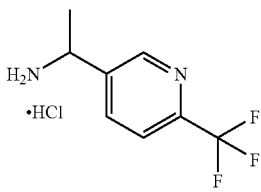

1-[6-(trifluoromethyl)pyridin-3-yl]ethanamine hydrochloride

Using a procedure similar to that described for Intermediate 14 and appropriate starting materials, replacing 4-methoxyphenylmagnesiumbromide with methylmagnesium bromide afforded the slow eluting diastereomer as the major product. The fast eluting diastereomer was not collected. The slow eluting diastereomer was treated to HCl as above affording the title compound. HPLC/MS: 295.0 (M+1); $R_t$=2.52 min.

INTERMEDIATE 19

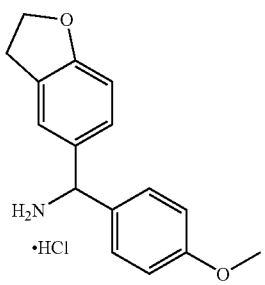

2,3-dihydro-1-benzofuran-5-yl(4-methoxyphenyl)methanaminium chloride

Using the procedure similar to that described for Intermediate 14, and appropriate starting materials, afforded what appeared to be one main diastereomer, however optical purity was not determined. The product was treated to HCl as above affording the title compound. HPLC/MS: 239.0 (M—NH$_2$)$^+$; $R_t$=2.08 min.

INTERMEDIATE 20

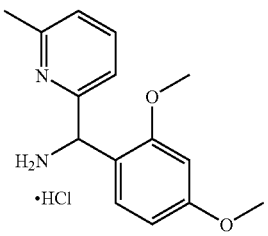

1-(2,4-dimethoxyphenyl)-1-(6-methylpyridin-2-yl)methanamine hydrochloride

Step A: (2,4-Dimethoxyphenyl)(6-methylpyridin-2-yl)methanone. 6-Methylpyridine-2-carbonitrile (4.88 g, 41.3 mmol) was dissolved in THF (50 mL), cooled to 0° C. and 2,4-dimethoxyphenylmagnesium bromide (20.5 mL, 10.24 mmol, 0.5 M in THF) was added. The reaction aged at rt for 3 h and was quenched with HCl (45.4 mL, 91 mmol, 2 M diethyl ether). The reaction was concentrated and extracted with EtOAc. The aq layer was basified to pH 10 and extracted with EtOAc. The combined organic portions were washed with brine, dried with Na$_2$SO$_4$, filtered and concentrated. The residue was purified by flash chromatography on silica gel gradient eluted with 0 to 50% EtOAc/hexane, affording the title compound. HPLC/MS: 258.3 (M+1); $R_t$=1.96 min.

Step B: N-[(1Z)-(2,4-Dimethoxyphenyl)(6-methylpyridin-2-yl)methylene]-2-methylpropane-2-sulfinamide. The product of Step A (9.81 g, 38.1 mmol) was dissolved in THF (100 mL) and R-2-methylpropane-2-sulfinamide (4.2 g, 34.7 mmol) and titanium tetraethanolate (15.81 g, 14.4 mL, 69.3 mmol) were added. The reaction aged at 60° C. for 24 h. The mixture was concentrated and dissolved in EtOAc. The solution was stirred while brine (40 mL) was added slowly and the resulting solution was stirred for 20 min. The reaction was filtered through a celite® plug and rinsed with EtOAc. The filtrate was transferred to a separatory funnel and the organic layer was isolated, dried with Na$_2$SO$_4$, filtered and concentrated. The residue was purified by flash chromatography on silica gel gradient eluted with 0 to 40% EtOAc/hexane, affording the title compound. HPLC/MS: 361.1 (M+1); $R_t$=2.60 min.

Step C: N-[(2,4-dimethoxyphenyl)(6-methylpyridin-2-yl)methyl]-2-methylpropane-2-sulfinamide. The product of Step B (2.41 g, 6.69 mmol) was dissolved in MeOH (60 mL), cooled to 0° C., and NaBH$_4$ (0.51 g, 13.37 mmol) was added portionwise. The reaction was aged for 45 min and was quenched with saturated aq NH$_4$Cl. The reaction was concentrated. The resulting paste was diluted in EtOAc and washed with brine. The organic portion was isolated, dried with Na$_2$SO$_4$, filtered and concentrated. The residue was purified by flash chromatography on silica gel gradient eluted with 0 to 100% EtOAc/hexane, affording a mixture of two diastereomers.

A portion of the set of diastereomers was dissolved in i-propanol/heptane and purified on a Chiracel OD chiral column eluting with 13% EtOH/heptane. In this fashion the isomers were isolated affording the fast eluting diastereomer on the OD column, HPLC/MS: 363.2 (M+1); $R_t$=2.24 min and the slow eluting diastereomer on the OD column, HPLC/MS: 363.2 (M+1); R. =2.16 min.

Step D: 1-(2,4-dimethoxyphenyl)-1-(6-methylpyridin-2-yl)methanamine hydrochloride. The fast eluting diasteromer (OD column) from Step C (0.99 g, 2.73 mmol) was dissolved in DCM (20 ml) and HCl (3 mL, 6 mmol, 2 M in diethyl ether) was added. The reaction was aged at rt for 15 min and concentrated to afford the title compound. HPLC/MS: 242.1 (M—NH$_2$)$^+$; $R_t$=2.08 min.

INTERMEDIATE 21

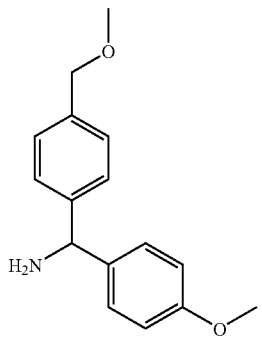

1-[4-(Methoxymethyl)phenyl]-1-(4-methoxyphenyl)methanamine

Step A: 4-(Methoxymethyl)benzonitrile. To a solution of 4-(hydroxymethyl)benzonitrile (5 g, 37.6 mmol) in DMF (100 mL) was added iodomethane (7.03 mL, 113 mmol) and NaH (1.502 g, 37.6 mmol). The reaction aged at rt for 2 h and was then partitioned between EtOAc and H$_2$O. The organic layer was separated and washed with H$_2$O (2×), brine, dried (MgSO$_4$), filtered and concentrated. The residue was purified by flash chromatography on silica gel gradient eluted with 0-20% EtOAc/hexane to afford the title compound. HPLC/MS: 148.1 (M+1); $R_t$=2.28 min.

Step B: 1-[4-(Methoxymethyl)phenyl]-1-(4-methoxyphenyl)methanamine. To the product of Step A (1.5 g, 10.19 mmol) in THF (15 mL) was added 4-methoxyphenylmagnesium bromide (11.21 mL, 11.21 mmol, 1.0 M). The reaction aged at rt for 3.5 h and was concentrated. The residue was dissolved in MeOH (20 mL) and then slowly treated with NaBH$_4$ (0.386 g, 10.19 mmol). The reaction was stirred at rt overnight, concentrated and treated with aq. HCl (15 mL, 30 mmol, 2.0 M). The aqueous portion was extracted with EtOAc (2×) and the combined organic layers were washed with a 1:1 solution of aq. 2.0 M NaOH/brine, dried (MgSO$_4$), filtered and concentrated. The residue was purified by flash chromatography on silica gel gradient eluted with 0-100% EtOAc/hexane to afford the title compound. HPLC/MS: 241.0 (M—NH$_2$)$^+$; $R_t$=1.91 min.

The racemic product of Step B was resolved into its separate enantiomers using a Berger SFC II preparative SFC with a ChiralPak AD-H 250×30 mm I. D. column eluting with 70:30 SFC CO$_2$:(EtOH+0.1% DEA) @50 mL/min. Analytical SFC was carried out on a Thar analytical SFC utilizing a ChiralPak AD-3, 150×4.6 mm I. D. column eluting with 70% SFC CO$_2$ and 30% EtOH containing 0.1% diethylamine at 2.4 mL/min detecting at 220 nm. Fast eluting enantiomer $R_t$=2.93 min and slow eluting enantiomer $R_t$=3.14 min.

INTERMEDIATE 22

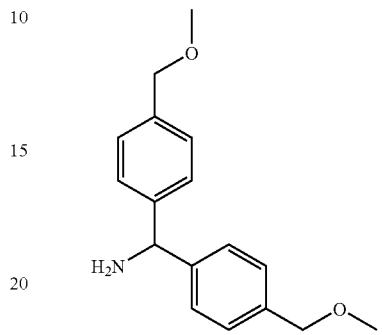

1,1-bis[4-(Methoxymethyl)phenyl]methanamine. To a solution of 4-bromobenzyl methyl ether (0.975 mL, 6.79 mmol, d=1.401 g/mL) in THF (20 mL) at −78° C. was added n-BuLi (2.85 mL, 7.13 mmol, 2.5 M in hexane) and the reaction was aged for 1 h. The reaction vessel was removed from the cooling bath and a solution of Intermediate 21, step A (1.00 g, 6.79 mmol) in THF (10 mL) was added. The reaction was aged at rt for 1 h and then concentrated. The residue was dissolved in MeOH (20 mL) and slowly treated with NaBH$_4$ (0.257 g, 6.79 mmol). The reaction was stirred at rt for 1.5 h, concentrated and treated with aq HCl (15 mL, 30 mmol, 2.0 M). The solution was adjusted to pH=7 using aq. NaOH (5.0 M) and extracted with EtOAc. The aqueous layer was then adjusted to pH=14 using aq. NaOH (5.0 M) and extracted with EtOAc. The combined organic layers were dried (MgSO$_4$), filtered and concentrated. The residue was purified by flash chromatography on silica gel gradient eluted with 0-100% EtOAc/hexane to afford the title compound. HPLC/MS: 255.0 (M—NH$_2$)$^+$; $R_t$=1.98 min.

INTERMEDIATE 23

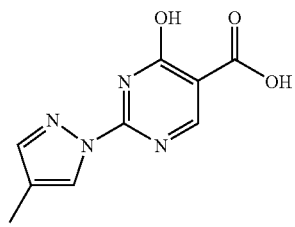

4-Hydroxy-2-(4-methyl-1H-pyrazol-1-yl)pyrimidine-5-carboxylic acid

Step A: 4-Methyl-1H-pyrazole-1-carboximidamide hydrochloride. To 4-Methyl-1H-pyrazole (4.9 g, 60 mmol) was added cyanamide (2.5 g, 60 mmol), HCl (5.6 mL, 62 mmol, 4 M in dioxane) and dioxane (60 mL). The reaction was heated to 110° C. and aged for 9 h. It was then aged at rt overnight. The mixture was diluted with Et$_2$O and stirred for 10 min. The product was isolated by filtration and washed with Et₂O to afford the title compound.

Step B: 4-Hydroxy-2-(4-methyl-1H-pyrazol-1-yl)pyrimidine-5-carboxylic acid. The product of step A (9 g, 46.8 mmol), NaOMe (16.0 mL, 70.2 mmol, 25% wt in MeOH) and diethyl ethoxymethylenemalonate (9.55 mL, 46.8 mmol) was dissolved in EtOH (100 mL). The reaction was heated for 1 h at 78° C. and became very thick. The mixture was slightly cooled and KOH (5.25 g, 94 mmol, 4.5 M in water) was added and the reaction became a cake. EtOH (20 mL) was added and the reaction was reheated at 78° C. for 90 min. Additional KOH (0.88 g, 15.7 mmol, 1 M in water) and EtOH (15 mL) were added and the reaction was heated 1 h. The mixture was cooled and HCl (20.9 mL, 265 mmol, 12 N) was added slowly and the slurry was diluted with Et₂O. The solids were filtered, suspended in HCl (0.6 M) and re-filtered. The product was washed with Et₂O:EtOH (1:1) and then hexane affording the titled compound. HPLC/MS: 221.1 (M+1); $R_t$=1.41 min.

EXAMPLE 112

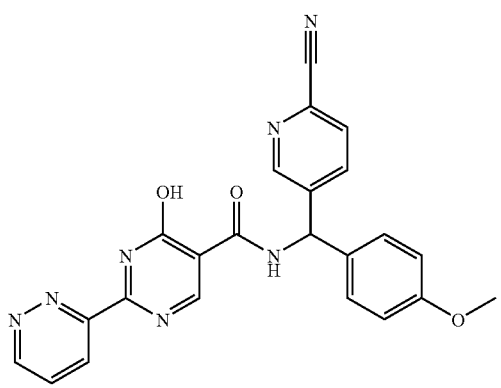

N-[(6-cyanopyridin-3-yl)(4-methoxyphenyl)methyl]-4-hydroxy-2-pyridazin-3-ylpyrimidine-5-carboxamide. The product of Example 169 (250 mg, 0.56 mmol) was dissolved in DMF (5 mL). Zn(CN)₂ (131 mg, 1.12 mmol), Pd₂(dba)₃ (26 mg, 0.028 mmol), and dppf (40 mg, 0.072 mmol) were added and the flask was evacuated and backfilled with N₂ 3 times. The mixture was heated at 110° C. overnight. The reaction was cooled and partitioned between DCM and aq HCl (2 M) and the organic layer was dried with Na₂SO₄, filtered and concentrated. The residue was purified on a reverse phase C-18 column eluting with 0 to 60% MeCN/water+v 0.1% TFA. Concentration of desired fractions afforded the title compound. HPLC/MS: 440.3 (M+1); $R_t$=2.60 min.

EXAMPLE 113

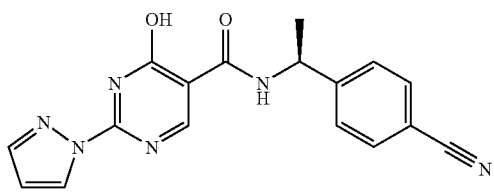

N-[(1S)-1-(4-cyanophenyl)ethyl]-4-hydroxy-2-(1H-pyrazol-1-yl)pyrimidine-5-carboxamide The product of Example 91 (113 mg, 0.29 mmol) was dissolved in dioxane (2 mL). NaCN (22 mg, 0.44 mmol), tetrakis (170 mg, 0.15 mmol) and 18-crown-6 (116 mg, 0.44 mmol) were added and the flask was evacuated and backfilled with N₂ 3 times. The mixture was heated at 100° C. for 6 h. The reaction was cooled and partitioned between EtOAc and aq HCl (2 M) and the organic layer was dried with Na₂SO₄, filtered and concentrated. The solid was washed with MeOH/EtOAc and isolated by filtration to afford the title compound. HPLC/MS: 335.1 (M+1); $R_t$=2.38 min.

EXAMPLE 114

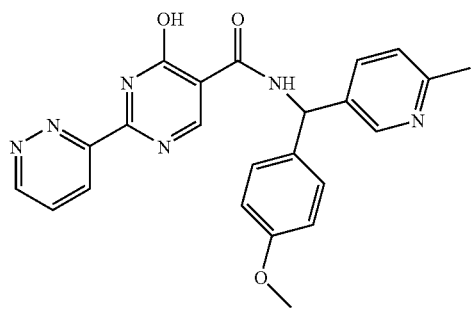

4-Hydroxy-N-[(4-methoxyphenyl)(6-methylpyridin-3-yl)methyl]-2-pyridazin-3-ylpyrimidine-5-carboxamide The product of Intermediate 8 (14 g, 64.2 mmol) and CDI (12 g, 73.8 mmol) in DMF (300 mL) was heated at 120° C. for 90 min. The reaction was allowed to come to rt and product from Intermediate 17 (21.2 g, 70.6 mmol) and NEt₃ (26 g, 257 mmol, 36.1 mL) were added. The reaction was heated at 80° C. for 5 h and stood at rt overnight. The reaction was concentrated and dissolved in chloroform and water. The pH was adjusted to about pH 5 with aq HCl (2 M). The organic portion was washed with water and the combined aq portions were back extracted with chloroform. The combined organic portions were washed with water, dried with Na₂SO₄, filtered and concentrated. The solid was suspended in EtOAc and heated to 80° C. The mixture aged at rt overnight. The solid was isolated by filtration and washed with 50% EtOAc/hexane, affording the title compound. HPLC/MS: 429.2 (M+1); $R_t$=1.99 min.

EXAMPLE 115

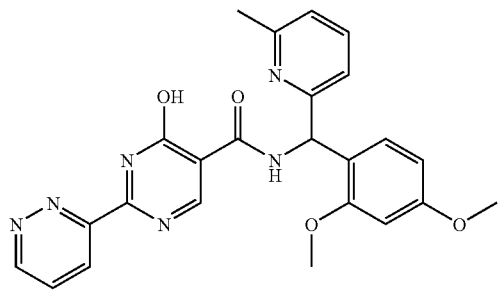

N-[(2,4-Dimethoxyphenyl)(6-methylpyridin-2-yl)methyl]-4-hydroxy-2-pyridazin-3-ylpyrimidine-5-carboxamide The product of Intermediate 8 (0.50 g, 2.29 mmol) and CDI (0.43 g, 2.64 mmol) in DMF (10 mL) was heated at 120° C. for 1 h. The reaction was allowed to come to rt and the product from Intermediate 20 (0.91 g, 2.75 mmol) and NEt$_3$ (0.71 g, 7.1 mmol, 1 mL) were added. The reaction was heated at 70° C. for 3 h and then aged at rt overnight. The reaction was concentrated and dissolved in chloroform and water. The pH was adjusted to about pH 5 with aq HCl (2 M). The organic portion was washed with water and the combined aq portions were back extracted with chloroform. The combined organic portions were washed with water, dried with Na$_2$SO$_4$, filtered and concentrated. The solid was suspended in EtOAc and heated to 80° C. Hexane was added to precipitate the product and the mixture was cooled and stood at rt for 20 min. The solid was isolated by filtration washing with 50% EtOAc/hexane affording the title compound. HPLC/MS: 459.2 (M+1); R$_t$=2.08 min.

Using procedures similar to Example 114 and using Intermediate 12, or commercially available amines, compounds, Examples 107 through 140 were prepared as shown in Table 4

TABLE 4

| Example | Name | HPLC/MS m/z (M + 1) R$_t$ (min) | Structure |
|---|---|---|---|
| Example 116 | 4-hydroxy-N-[(1S)-1-(4-methoxyphenyl)ethyl]-2-(1H-pyrazol-1-yl)pyrimidine-5-carboxamide | 340.1 2.64 | 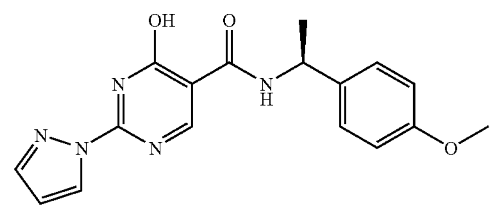 |
| Example 117 | 4-hydroxy-N-[1-(4-methyl-1,3-thiazol-2-yl)ethyl]-2-(1H-pyrazol-1-yl)pyrimidine-5-carboxamide hydrochloride | 331.1 2.15 | 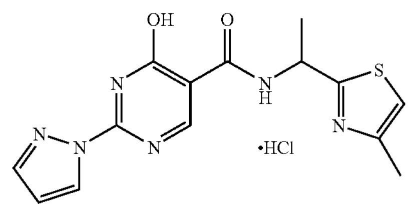 |
| Example 118 | 4-hydroxy-2-(1H-pyrazol-1-yl)-N-[1-(pyridin-2-yl)ethyl]pyrimidine-5-carboxamide | 311.2 0.50 | 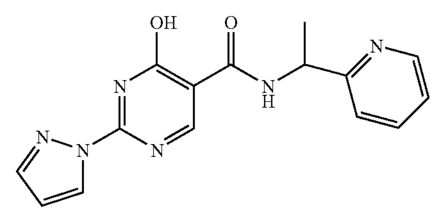 |
| Example 119 | N-[(1S)-2,3-dihydro-1H-inden-1-yl]-4-hydroxy-2-(1H-pyrazol-1-yl)pyrimidine-5-carboxamide | 322.0 2.75 | 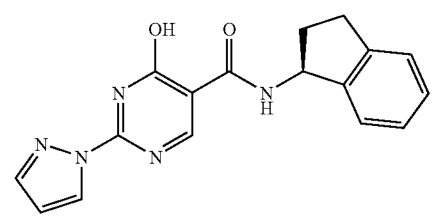 |
| Example 120 | 4-hydroxy-N-[(1R,2S)-2-hydroxy-1,2-diphenylethyl]-2-(1H-pyrazol-1-yl)pyrimidine-5-carboxamide | 402.0 2.73 | 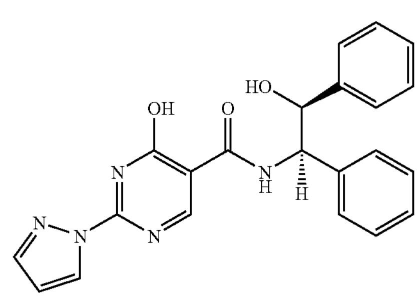 |

TABLE 4-continued

| Example | Name | HPLC/MS m/z (M + 1) R_t (min) | Structure |
|---|---|---|---|
| Example 121 | 4-hydroxy-N-[(1S)-1-(naphthalen-2-yl)ethyl]-2-(1H-pyrazol-1-yl)pyrimidine-5-carboxamide | 360.0 3.07 | 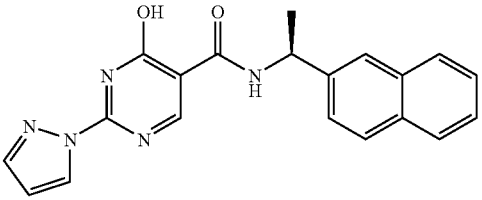 |
| Example 122 | 4-hydroxy-N-[(1S)-2-hydroxy-1-phenylethyl]-2-(1H-pyrazol-1-yl)pyrimidine-5-carboxamide | 326.2 1.97 | 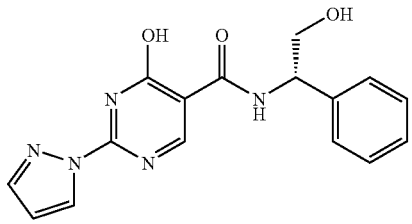 |
| Example 123 | 4-hydroxy-N-[(1R)-2-hydroxy-1-phenylethyl]-2-(1H-pyrazol-1-yl)pyrimidine-5-carboxamide | 326.1 2.06 | 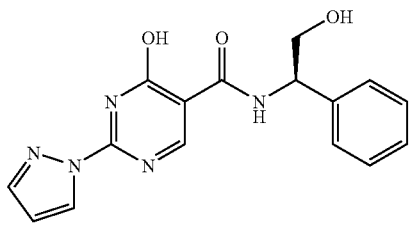 |
| Example 124 | (2R)-({[4-hydroxy-2-(1H-pyrazol-1-yl)pyrimidin-5-yl]carbonyl}amino)(phenyl)ethanoic acid | 340.0 2.13 | 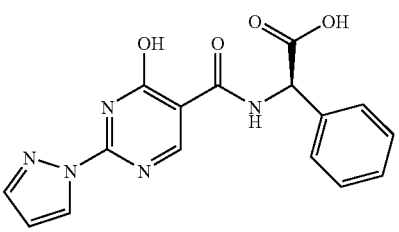 |
| Example 125 | 4-hydroxy-N-[phenyl(pyridin-2-yl)methyl]-2-(1H-pyrazol-1-yl)pyrimidine-5-carboxamide trifluoroacetate (salt) | 373.0 2.21 | 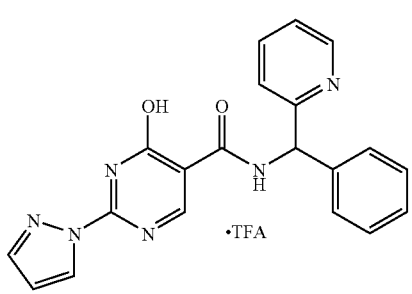 |
| Example 126 | 4-hydroxy-N-[(1S)-1-(3-methoxyphenyl)ethyl]-2-(1H-pyrazol-1-yl)pyrimidine-5-carboxamide | 340.0 2.67 | 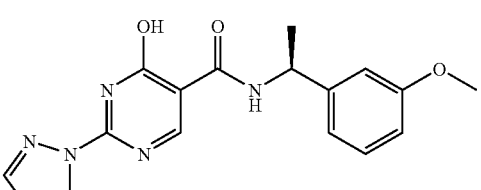 |

TABLE 4-continued

| Example | Name | HPLC/MS m/z (M + 1) $R_t$ (min) | Structure |
|---|---|---|---|
| Example 127 | 4-hydroxy-N-[(1R,2R)-2-hydroxy-1,2-diphenylethyl]-2-(1H-pyrazol-1-yl)pyrimidine-5-carboxamide | 402.0 2.72 | 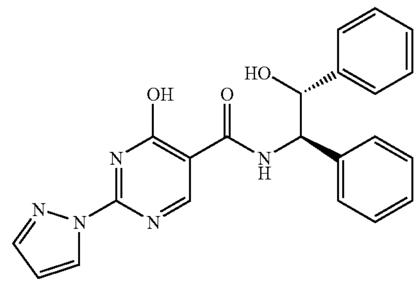 |
| Example 128 | 4-hydroxy-N-[(1R)-2-hydroxy-2-methyl-1-phenylpropyl]-2-(1H-pyrazol-1-yl)pyrimidine-5-carboxamide | 354.1 2.38 | 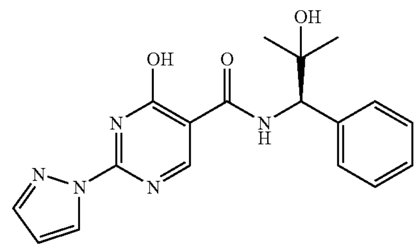 |
| Example 129 | 4-hydroxy-N-[(1S)-1-(4-phenoxyphenyl)ethyl]-2-(1H-pyrazol-1-yl)pyrimidine-5-carboxamide | 402.0 3.27 | 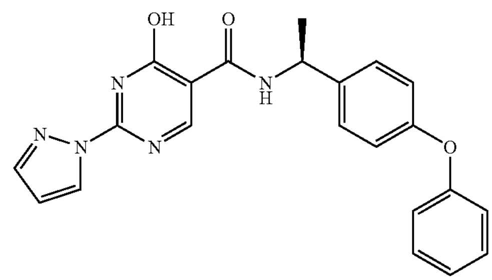 |
| Example 130 | 4-hydroxy-2-(1H-pyrazol-1-yl)-N-{[5-(trifluoromethyl)pyridin-2-yl]methyl}pyrimidine-5-carboxamide | 365.0 2.52 | 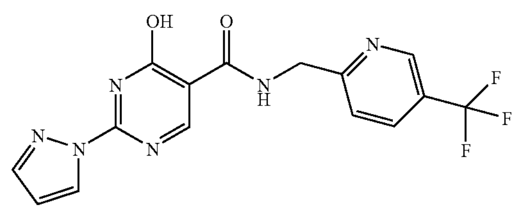 |
| Example 131 | 4-hydroxy-N-(2-methyl-1-phenylpropyl)-2-(1H-pyrazol-1-yl)pyrimidine-5-carboxamide | 338.1 3.00 | 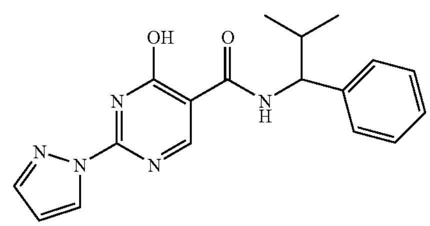 |
| Example 132 | N-[(1S)-1-(2,3-dihydro-1,4-benzodioxin-6-yl)ethyl]-4-hydroxy-2-(1H-pyrazol-1-yl)pyrimidine-5-carboxamide | 368.0 2.61 | 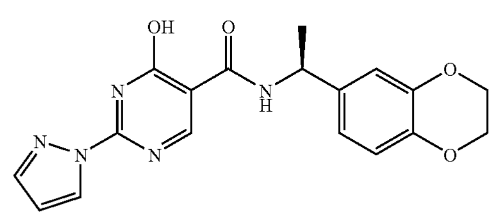 |

TABLE 4-continued

| Example | Name | HPLC/MS m/z (M + 1) R$_t$ (min) | Structure |
|---|---|---|---|
| Example 133 | 4-hydroxy-2-(4-methyl-1H-pyrazol-1-yl)-N-[(1S)-1-phenylpropyl]pyrimidine-5-carboxamide | 338.0 3.03 | 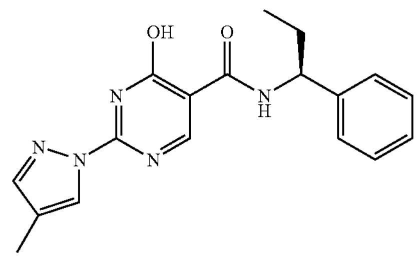 |
| Example 134 | 4-hydroxy-N-[(1S)-1-(4-methoxyphenyl)ethyl]-2-(4-methyl-1H-pyrazol-1-yl)pyrimidine-5-carboxamide | 354.1 2.86 | 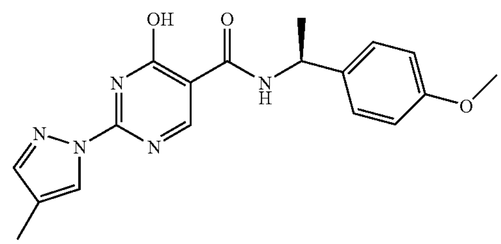 |
| Example 135 | N-cyclohexyl-4-hydroxy-2-(pyridazin-3-yl)pyrimidine-5-carboxamide | 300.2 0.89 (Basic) | 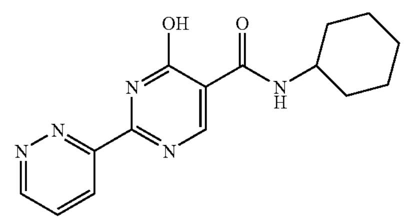 |
| Example 136 | 4-hydroxy-N-[phenyl(pyridin-2-yl)methyl]-2-pyridazin-3-ylpyrimidine-5-carboxamide trifluoroacetate (salt) | 385.0 2.07 | 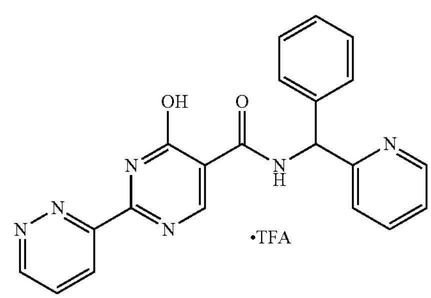 |
| Example 137 | 4-hydroxy-N-[(1S)-1-(4-phenoxyphenyl)ethyl]-2-(pyridazin-3-yl)pyrimidine-5-carboxamide | 414.0 3.11 | 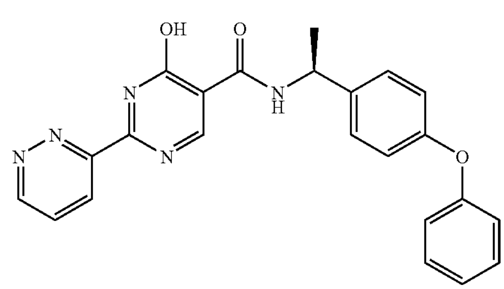 |

TABLE 4-continued

| Example | Name | HPLC/MS m/z (M + 1) R$_t$(min) | Structure |
|---|---|---|---|
| Example 138 | 4-hydroxy-N-[(1R,2S)-2-hydroxy-1,2-diphenylethyl]-2-pyridazin-3-yl)pyrimidine-5-carboxamide | 414.0 2.57 | 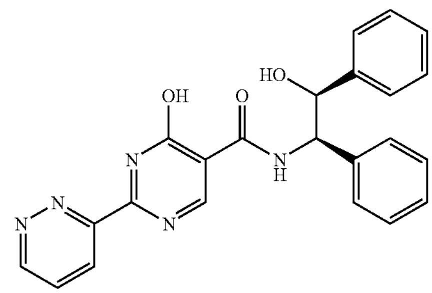 |
| Example 139 | 4-hydroxy-N-[(1R,2R)-2-hydroxy-1,2-diphenylethyl]-2-(pyridazin-3-yl)pyrimidine-5-carboxamide | 414.0 2.58 | 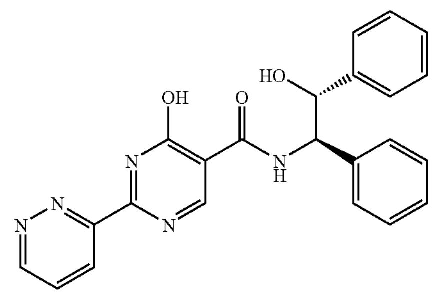 |
| Example 140 | N-[(1S)-1-(2,3-dihydro-1,4-benzodioxin-6-yl)ethyl]-4-hydroxy-2-(pyridazin-3-yl)pyrimidine-5-carboxamide | 380.0 3.79 | 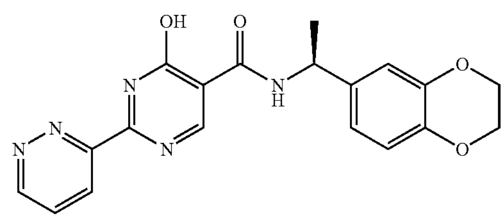 |

Using procedures similar to that described in Example 114, and procedures for making chiral amines similar to that described for Intermediate 14, Intermediate 15, Intermediate 16, Intermediate 17, Intermediate 18, Intermediate 19, Intermediate 20 and Intermediate 21, along with the appropriate starting materials the following compounds, Examples 141 through 164 were prepared as shown in Table 5. Asymmetric synthesis of diarylmethylamines has been described by Plobeck, N.; Powell, D. *Tetrahydron: Asymmetry,* 2002, 13, 303-310. The preparation of N-tert-butanesulfinimines from aldehydes and ketones which can in turn be converted to optically pure amines has been elegantly described by Lui, G.; Cogan, D. A.; Owens, T. D., Tang, T. P; Ellman, J. A. *J. Org. Chem,* 1999, 64, 1278-1284.

TABLE 5

| Example | Name | HPLC/MS m/z (M + 1) R$_t$(min) | Structure |
|---|---|---|---|
| Example 141 Enantiomer 1 | 4-hydroxy-2-(1H-pyrazol-1-yl)-N-{1-[6-(trifluoromethyl)pyridin-3-yl]ethyl}pyrimidine-5-carboxamide | 379.0 2.45 | 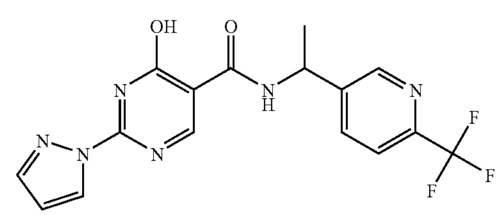 |

TABLE 5-continued

| Example | Name | HPLC/MS m/z (M + 1) R$_t$ (min) | Structure |
|---|---|---|---|
| Example 142 Enantiomer 1 Example 143 Enantiomer 2 | 4-hydroxy-N-{phenyl[6-(trifluoromethyl)pyridin-3-yl]methyl}-2-(1H-pyrazol-1-yl)pyrimidine-5-carboxamide | 440.9 3.14 | 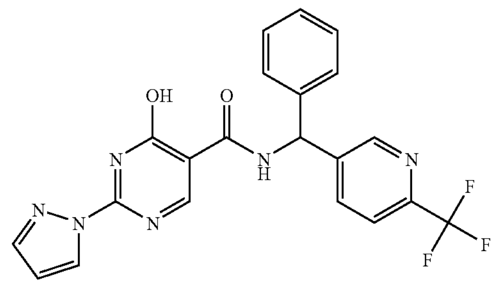 |
| Example 144 Enantiomer 1 Example 145 Enantiomer 2 | 4-hydroxy-N-[(4-methoxyphenyl)(4-methyl-1,3-thiazol-2-yl)methyl]-2-(pyridazin-3-yl)pyrimidine-5-carboxamide | 435.1 2.63 | 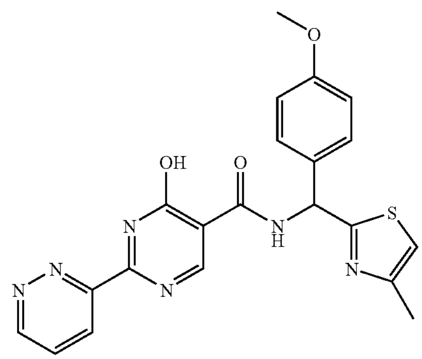 |
| Example 146 Enantiomer 1 | 4-hydroxy-N-[(4-methoxyphenyl)(6-methylpyridin-3-yl)methyl]-2-(pyridazin-3-yl)pyrimidine-5-carboxamide | 429.2 1.97 | 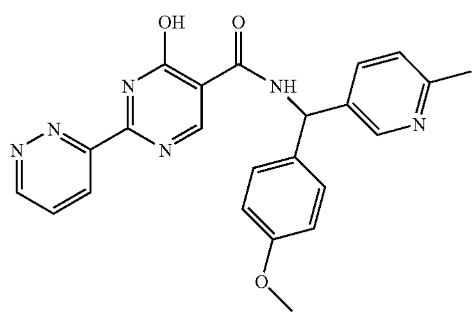 |
| Example 147 Enantiomer 1 Example 148 Enantiomer 2 | N-[(3-cyanophenyl)(4-methoxyphenyl)methyl]-4-hydroxy-2-(pyridazin-3-yl)pyrimidine-5-carboxamide | 439.2 2.76 | 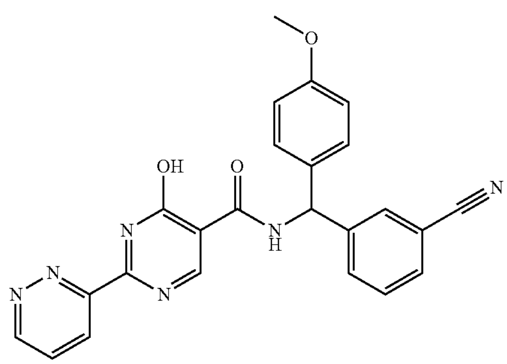 |

TABLE 5-continued

| Example | Name | HPLC/MS m/z (M + 1) R$_t$ (min) | Structure |
|---|---|---|---|
| Example 149 Enantiomer 1 | N-[(2,4-dimethoxyphenyl)(6-methylpyridin-2-yl)methyl]-4-hydroxy-2-(pyridazin-3-yl)pyrimidine-5-carboxamide | 459.2 2.08 | 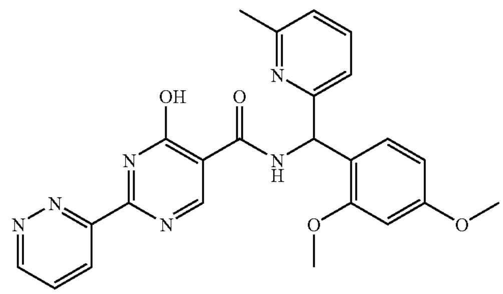 |
| Example 150 Enantiomer 1 Example 151 Enantiomer 2 | N-[(4-cyanophenyl)(4-methoxyphenyl)methyl]-4-hydroxy-2-(pyridazin-3-yl)pyrimidine-5-carboxamide | 439.1 3.11 3.15 | 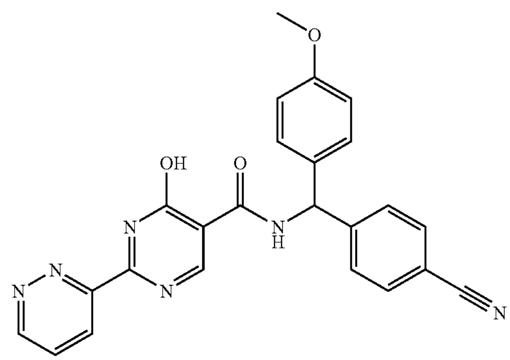 |
| Example 152 Enantiomer 1 Example 153 Enantiomer 2 | 4-hydroxy-N-{(4-methoxyphenyl)[4-(trifluoromethoxy)phenyl]methyl}-2-(pyradazin-3-yl)pyrimidine-5-carboxamide | 498.2 3.53 3.54 | 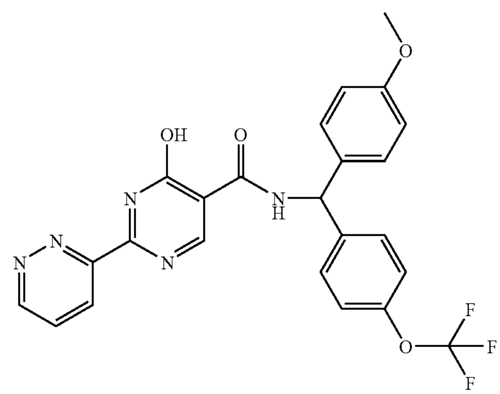 |
| Example 154 Enantiomer 1 Example 155 Enantiomer 2 | N-[(4-cyanophenyl)(2,4-dimethoxyphenyl)methyl]-4-hydroxy-2-(pyridazin-3-yl)pyrimidine-5-carboxamide | 469.4 2.80 2.84 | 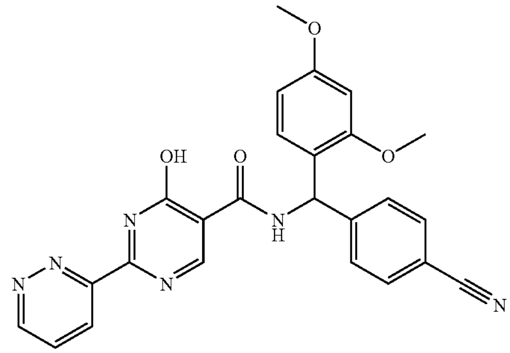 |

TABLE 5-continued

| Example | Name | HPLC/MS m/z (M + 1) R$_t$ (min) | Structure |
|---|---|---|---|
| Example 156 Enantiomer 1 Example 157 Enantiomer 2 | 4-hydroxy-N-[(4-hydroxyphenyl)(4-methoxyphenyl)methyl]-2-(pyridazin-3-yl)pyrimidine-5-carboxamide | 430.2 2.75 430.2 2.75 | 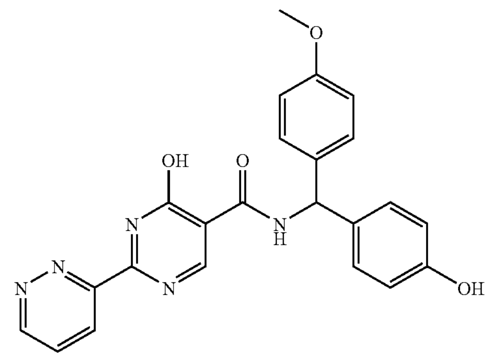 |
| Example 158 Enantiomer 1 Example 159 Enantiomer 2 | N-[1-(4-cyanophenyl)-3-methylbutyl]-4-hydroxy-2-(pyridazin-3-yl)pyrimidine-5-carboxamide | 389.1 2.88 | 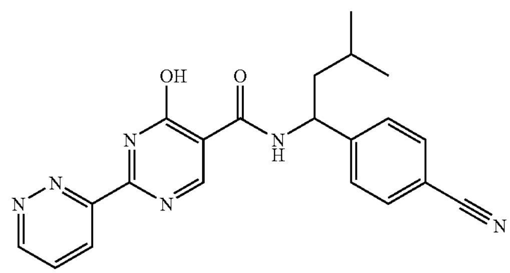 |
| Example 160 Enantiomer 1 Example 161 Enantiomer 2 | N-[1-(4-cyanophenyl)-2-(4-methoxyphenyl)ethyl]-4-hydroxy-2-(pyridazin-3-yl)pyrimidine-5-carboxamide | 453.1 2.84 | 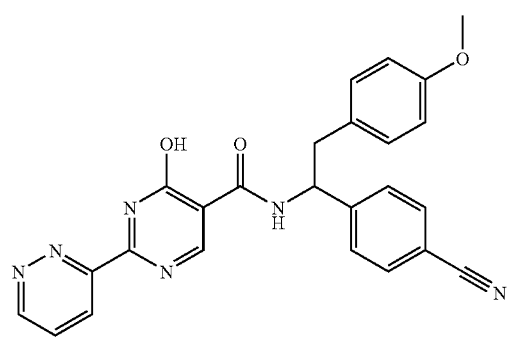 |
| Example 162 Enantiomer 1 Example 163 Enantiomer 2 | N-[(4-cyanophenyl)(cyclohexyl)methyl]-4-hydroxy-2-(pyridazin-3-yl)pyrimidine-5-carboxamide | 415.1 3.07 3.08 | 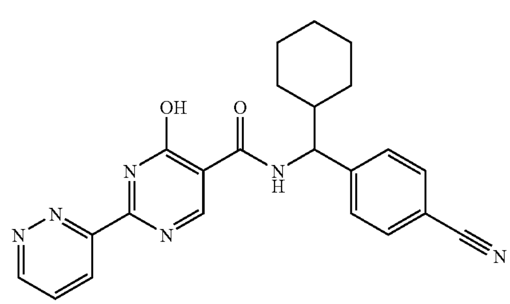 |

TABLE 5-continued

| Example | Name | HPLC/MS m/z (M + 1) $R_t$ (min) | Structure |
|---|---|---|---|
| Example 164 Enantiomer 1 | N-[2,3-dihydro-1-benzofuran-5-yl(4-methoxyphenyl)methyl]-4-hydroxy-2-(pyridazin-3-yl)pyrimidine-5-carboxamide | | 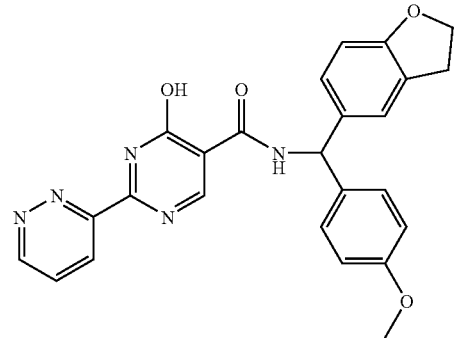 |

Using procedures similar to that described in Example 114 and procedures described for Intermediate 13, and Intermediate 21 and the appropriate starting materials the following compounds, Examples 165 through 179 were prepared as shown in Table 6. The preparation of homo and heterobiaryl-methylamines in racemic from has been described by Terrasson, V.; Marque, S.; Scarpacci, A.; Prim, D. *Synthesis*, 2006, 11, 1858-1862.

TABLE 6

| Example | Name | HPLC/MS m/z (M + 1) $R_t$ (min) | Structure |
|---|---|---|---|
| Example 165 | N-[1-(biphenyl-4-yl)butyl]-4-hydroxy-2-(1H-pyrazol-1-yl)pyrimidine-5-carboxamide | 414.0 3.61 | 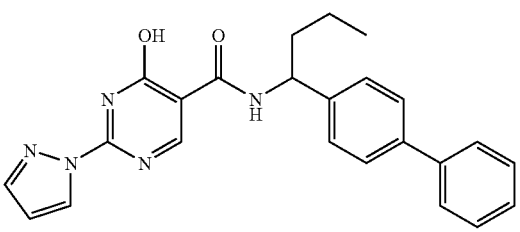 |
| Example 166 | 4-hydroxy-N-[(4-methoxyphenyl)(pyrazin-2-yl)methyl]-2-(1H-pyrazol-1-yl)pyrimidine-5-carboxamide | 404.1 2.48 | 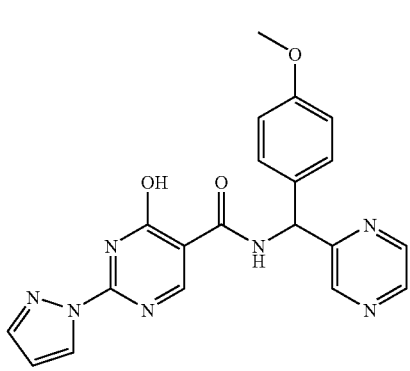 |

TABLE 6-continued

| Example | Name | HPLC/MS m/z (M + 1) R$_t$ (min) | Structure |
|---|---|---|---|
| Example 167 | 4-hydroxy-N-[(4-methoxyphenyl)(6-methoxypyridin-3-yl)methyl]-2-(1H-pyrazol-1-yl)pyrimidine-5-carboxamide trifluoroacetate (salt) | 433.0 2.77 | 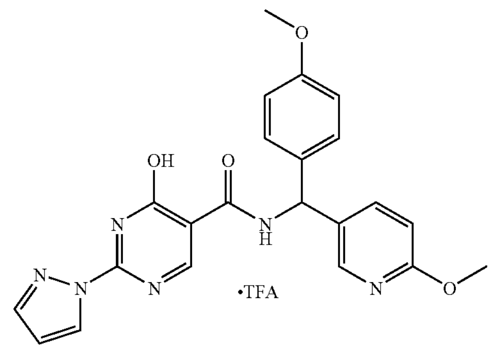 |
| Example 168 | 4-hydroxy-N-{(4-methoxyphenyl)[4-(methylsulfanyl)phenyl]methyl}-2-(1H-pyrazol-1-yl)pyrimidine-5-carboxamide | 448.1 3.23 | 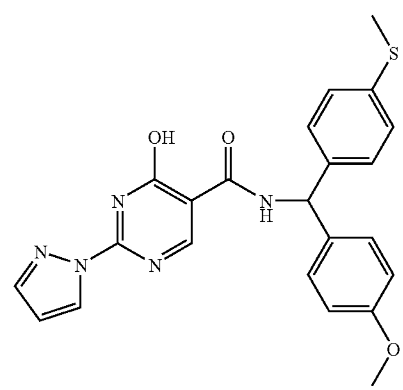 |
| Example 169 | N-[(6-chloropyridin-3-yl)(4-methoxyphenyl)methyl]-4-hydroxy-2-(pyridazin-3-yl)pyrimidin-5-carboxamide | 448.9 2.77 | 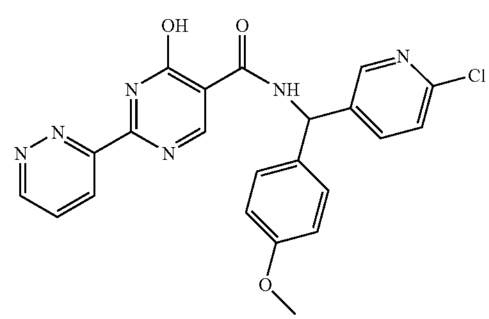 |
| Example 170 | 4-hydroxy-N-[(4-methoxyphenyl)(6-methoxypyridin-3-yl)methyl]-2-(pyridazin-3-yl)pyrimidine-5-carboxamide | 445.0 2.58 | 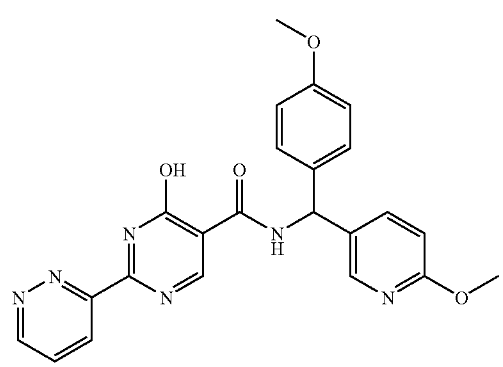 |

TABLE 6-continued

| Example | Name | HPLC/MS m/z (M + 1) R$_t$ (min) | Structure |
|---|---|---|---|
| Example 171 | 4-hydroxy-N-[(4-methoxyphenyl)(quinolin-2-yl)methyl]-2-(pyridazin-3-yl)pyrimidine-5-carboxamide | 465.0 2.66 | 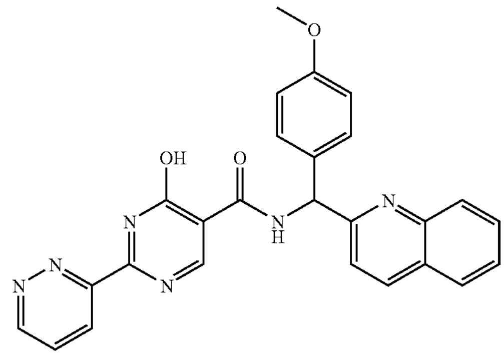 |
| Example 172 | 4-hydroxy-N-[(4-methoxyphenyl)(6-methoxyquinolin-2-yl)methyl]-2-(pyridazin-3-yl)pyrimidine-5-carboxamide | 495.0 2.66 | 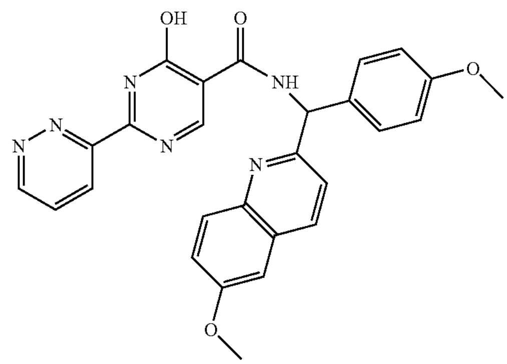 |
| Example 173 | N-[1,3-benzothiazol-2-yl(4-methoxyphenyl)methyl]-4-hydroxy-2-(pyridazin-3-yl)pyrimidine-5-carboxamide | 471.1 2.98 | 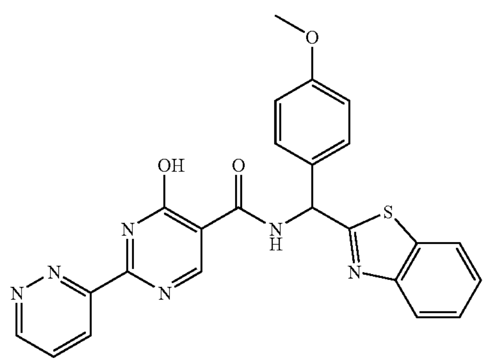 |
| Example 174 | N-[bis(2,4-dimethoxyphenyl)methyl]-4-hydroxy-2-(pyridazin-3-yl)pyrimidine-5-carboxamide | 504.2 3.16 | 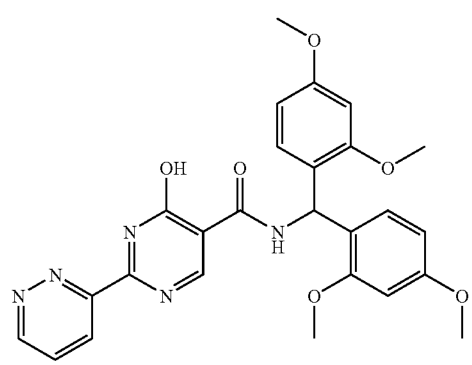 |

TABLE 6-continued

| Example | Name | HPLC/MS m/z (M + 1) R_t (min) | Structure |
|---|---|---|---|
| Example 175 | N-[bis(4-methoxy-2-methylphenyl)methyl]-4-hydroxy-2-(pyridazin-3-yl)pyrimidine-5-carboxamide | 472.1 3.09 | 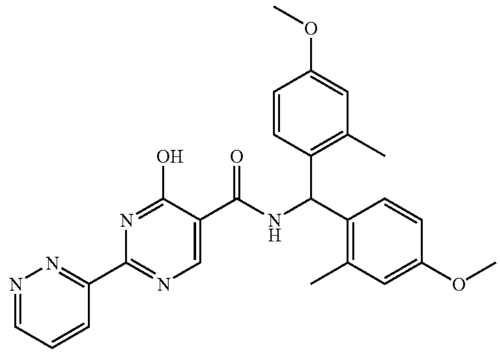 |
| Example 176 | N-[(2,4-dimethoxyphenyl)(4-fluorophenyl)methyl]-4-hydroxy-2-(pyridazin-3-yl)pyrimidine-5-carboxamide | 462.0 2.95 | 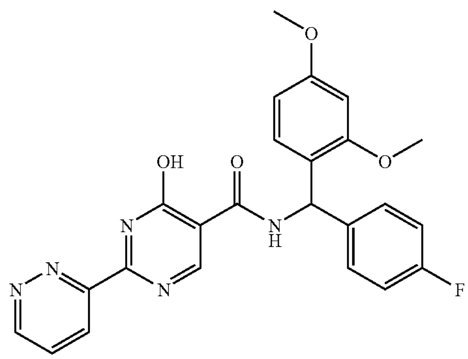 |
| Example 177 | N-[(2,6-dimethoxypyridin-3-yl)(4-fluorophenyl)methyl]-4-hydroxy-2-(pyridazin-3-yl)pyrimidine-5-carboxamide | 463.1 3.05 | 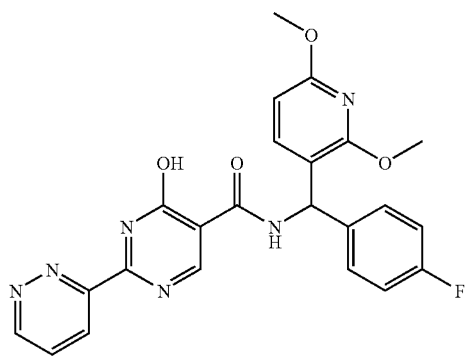 |
| Example 178 | 4-hydroxy-N-{(4-methoxyphenyl)[4-(methylsulfanyl)phenyl]methyl}-2-(pyridazin-3-yl)pyrimidine-5-carboxamide | 460.1 3.09 | 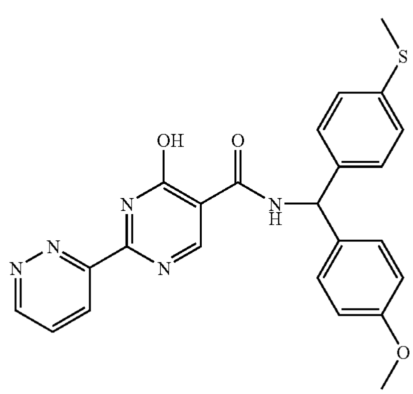 |

TABLE 6-continued

| Example | Name | HPLC/MS m/z (M + 1) R$_t$ (min) | Structure |
|---|---|---|---|
| Example 179 | N-{(4-chlorophenyl)[4-(1-hydroxyethyl)phenyl]methyl}-4-hydroxy-2-(pyridazin-3-yl)pyrimidine-5-carboxamide | 462.1<br>2.82 | 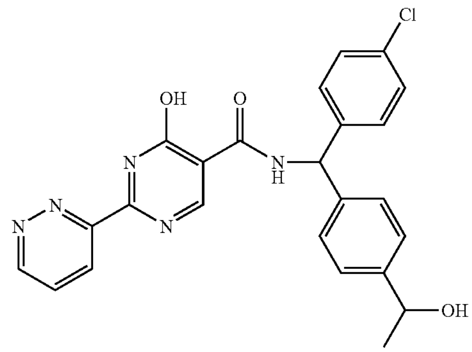 |

EXAMPLE 180

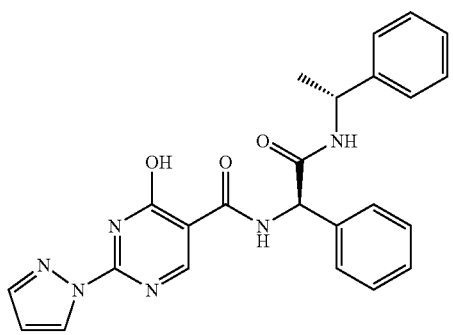

4-Hydroxy-N-((1R)-2-oxo-1-phenyl-2-{[(1R)-1-phenylethyl]amino}ethyl)-2-(1H-pyrazol-1-yl)pyrimidine-5-carboxamide To the product from Example 124 (100 mg, 0.3 mmol), DIPEA (57 g, 0.44 mmol), (1R)-1-phenylethanamine (36 mg, 0.3 mmol) and HOBt (45 mg, 0.3 mmol) in 1.4 ML DMF was added 1-ethyl-3-(3'-dimethylaminopropyl)carbodiimide hydrochloride (EDC) (59 mg, 0.31 mmol). The mixture aged for 2 days at rt. The reaction was diluted with EtOAc and washed with aq HCl (1 M) and water (2×). The organic portion was dried with Na$_2$SO$_4$, filtered and concentrated. The solids were suspended in EtOAc and hexane (6:4) and isolated via filtration. The product was washed with 10% EtOAc/hexane. HPLC/MS: 443.0 (M+1); R$_t$=2.90 min.

EXAMPLE 181

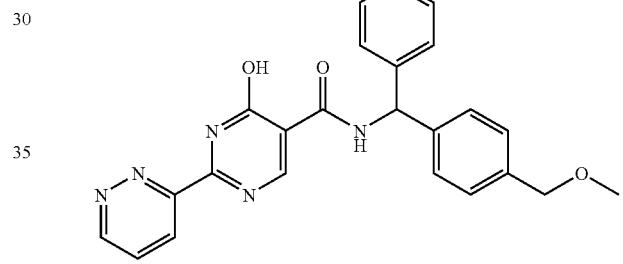

4-Hydroxy-N-[[4-(methoxymethylphenyl](4-methoxyphenyl)methyl]-2-pyridazin-3-ylpyrimidine-5-carboxamide. (racemic)

To the product of Intermediate 8 (0.200 g, 0.917 mmol) was added CDI (0.149 g; 0.917 mmol) and DMF (3 mL). The reaction was heated in a microwave for 10 min at 120° C. and subsequently cooled to rt. The racemic product of Intermediate 21 (0.212 g, 0.825 mmol) was added; the reaction was heated in a microwave for 10 min at 100° C., cooled to rt and partitioned between CHCl$_3$ and H$_2$O. The organic layer was separated, washed with H$_2$O (2×) and concentrated. The residue was crystallized using EtOAc to afford the title compound. HPLC/MS: 458.1 (M+1); R$_t$=2.82 min.

Using a procedure similar to that of Example 181 and the optically pure amines of Intermediate 21 the following two compounds, Examples 182 and 183 were prepared as shown in Table 7.

TABLE 7

| Example | Name | HPLC/MS m/z (M + 1) R$_t$ (min) | Structure |
|---|---|---|---|
| Example 122 Enantiomer 1 Example 183 Enantiomer 2 | 4-Hydroxy-N-[[4-(methoxymethyl)phenyl](4-methoxyphenyl)methyl]-2-pyridazin-3-ylpyrimidine-5-carboxamide | 458.0 2.84 458.1 2.82 | |

EXAMPLE 184

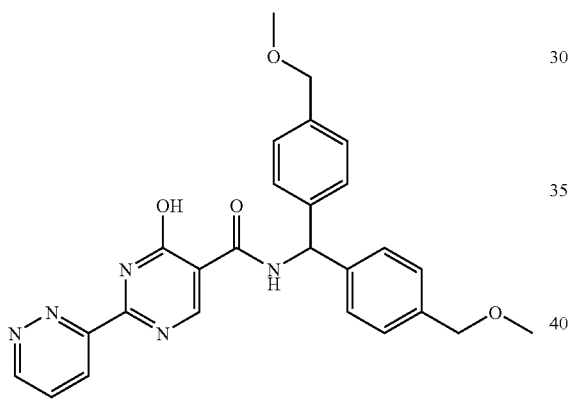

N-{bis[4-(methoxymethyl)phenyl]methyl}-4-hydroxy-2-pyridazin-3-ylpyrimidine-5-carboxamide To the product of Intermediate 8 (0.175 g, 0.802 mmol) was added CDI (0.130 g, 0.802 mmol) and DMF (2 mL). The reaction was heated in a microwave for 10 min at 120° C. and subsequently cooled to rt. The product of Intermediate 22 (0.202 g, 0.744 mmol) in DMF (2 mL) was added followed by NEt$_3$ (0.111 mL, 0.802 mmol, d=0.73 g/mL). The reaction was heated in a microwave for 10 min at 100° C., cooled to rt and partitioned between CHCl$_3$ and H$_2$O. The organic layer was separated, washed with H$_2$O (2×) and concentrated. The title compound was crystallized from the residue using EtOAc and hexane. The solid was isolated by filtration and rinsed with EtOAc followed by EtOH. HPLC/MS: 472.1 (M+1); R$_t$=2.81 min.

EXAMPLE 185

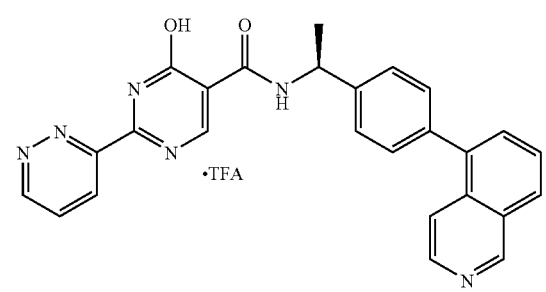

4-hydroxy-N-[(1S)-1-(4-isoquinolin-5-ylphenyl)ethyl]-2-pyridazin-3-ylpyrimidine-5-carboxamide A mixture of Example 25 (0.103 g, 0.257 mmol), 5-isoquinolineboronic acid (0.093 g, 0.540 mmol) and Tetrakis (0.030 g, 0.026 mmol) in NMP/IPA/H$_2$O (1.2/0.9/0.1 mL) was treated with aq Na$_2$CO$_3$ (0.257 mL, 0.515 mmol, 2.0 M) followed by evacuation of the atmosphere and replacement with N$_2$ (3×). The reaction was heated in a microwave for 30 min at 150° C., cooled to rt and diluted with MeCN/H$_2$O. The solution was purified on a reverse phase C-18 column with gradient elution 20-80% MeCN/H$_2$O+v 0.1% TFA. Concentration of the desired fractions afforded the title compound. HPLC/MS: 449.0 (M+1); R$_t$=2.15 min.

Using procedures similar to that described in Example 185 and the appropriate starting materials the following compounds, Examples 186 and 187 were prepared as shown in Table 8.

TABLE 8

| Example | Name | HPLC/MS m/z (M + 1) R_t (min) | Structure |
|---|---|---|---|
| Example 186 | N-{(1S)-1-[4-(6-fluoropyridin-3-yl)phenyl]ethyl}-4-hydroxy-2-pyridazin-3-ylpyrimidine-5-carboxamide trifluoroacetate (salt) | 417.0 2.72 | 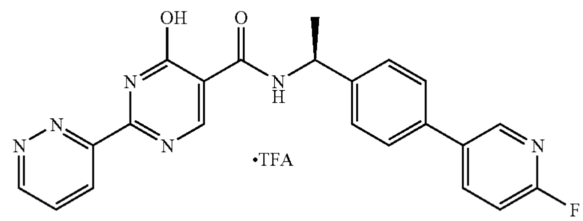 |
| Example 187 | 4-hydroxy-2-pyridazin-3-yl-N-[(1S)-1-(4-pyridin-3-ylphenyl)ethyl]pyrimidine-5-carboxamide trifluoroacetate (salt) | 399.0 1.72 | 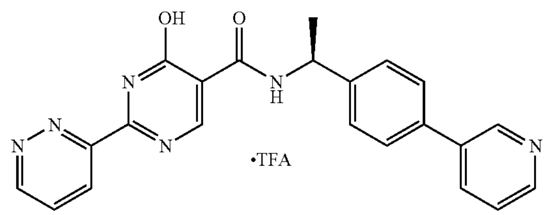 |

EXAMPLE 188

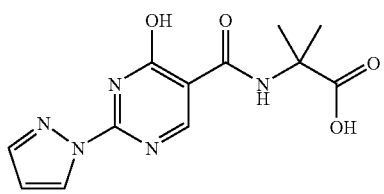

N-{[4-hydroxy-2-(1H-pyrazol-1-yl)pyrimidin-5-yl]carbonyl}-2-methylalanine

Step A: tert-butyl N-{[4-hydroxy-2-(1H-pyrazol-1-yl)pyrimidin-5-yl]carbonyl}-2-methylalaninate The product of Intermediate 10 (5.50 g, 26.7 mmol) was combined with CDI (5.13 g, 30.7 mmol) and DMF (90 mL). The reaction was aged at 110° C. for 30 min and cooled to about 45° C. Tert-butyl 2-methylalaninate (4.25 g, 26.7 mmol) and NEt₃ (11.16 mL, 80 mmol) were added and the reaction was aged at 55° C. for an additional 4 h. The reaction was concentrated and then diluted with DCM and washed with aq HCl (30 ml, 2 M) in water (400 mL). The aqueous portion was back extracted with DCM and the combined organic portions were washed with water. The organic portion was concentrated and suspended in EtOAc (50 mL) and then hexane (70 mL). The mixture was aged at 40° C. for about 15 min before hexane (about 250 mL) was added. The mixture was aged an additional 25 min at 40° C. and the product was isolated by filtration. The solid was then washed with 10% EtOAc/90% hexane followed by hexane to afford the product. HPLC/MS: 370.25 (M+Na)⁺; R_t=2.71 min.

Step B: N-{[4-hydroxy-2-(1H-pyrazol-1-yl)pyrimidin-5-yl]carbonyl}-2-methylalanine The product of Step A (3.0 g, 8.64 mmol) was combined with DCM (18 ml) and TFA (2.5 mL). The reaction was aged at reflux for about 5 h and then concentrated. The product was then treated with Et₂O, isolated by filtration, and washed with hexane to afford the title compound. HPLC/MS: 292.0 (M+1); R_t=1.42 min.

EXAMPLE 189

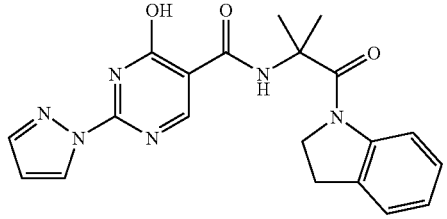

N-[1-(2,3-dihydro-1H-indol-1-yl)-2-methyl-1-oxopropan-2-yl]-4-hydroxy-2-(1H-pyrazol-1-yl)pyrimidine-5-carboxamide To the product of Example 188 (100 mg, 0.343 mmol), DIPEA (0.15 mL 0.86 mmol), 2,3-dihydro-1H-indole (0.04 ml, 0.36 mmol) and HOBt (55.2 mg, 0.36 mmol) in 1.4 mL DMF was added EDC (69.1 mg, 0.36 mmol). The reaction aged at rt for 3.5 h. The reaction was diluted with EtOAc and washed with aq HCl (2 M) and water. The organic portion was partially concentrated and the product was allowed to crystallize. The mixture was diluted with 80% EtOAc/20% hexane before the product was isolated by filtration. It was then washed with 80% EtOAc/20% hexane to afford the title compound. HPLC/MS: 393.0 (M+1); $R_t$=2.63 min.

EXAMPLE 190 Fast Eluting Enantiomer

EXAMPLE 191 Slow Eluting Enantiomer

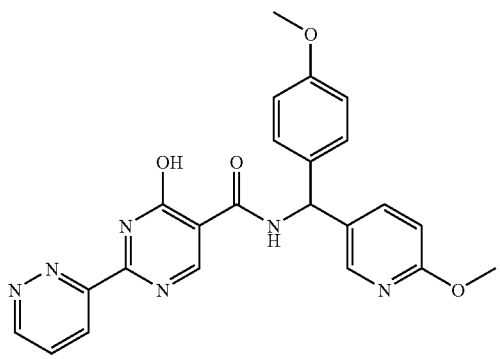

4-hydroxy-N-[(4-methoxyphenyl)(6-methoxypyridin-3-yl)methyl]-2-(pyridazin-3-yl)pyrimidine-5-carboxamide The racemic product of Example 170 was resolved into its separate enantiomers using a Berger SFC II preparative SFC with a ChiralPak AS-H 250×20 mm I. D. column eluting with 65:35 SFC $CO_2$: (2-propanol) @ 40 mL/min. The sample was dissolved in MeOH at 8 mg/mL. Injections of 1 mL per injection were used. Analytical SFC was carried out on a Thar analytical SFC utilizing a ChiralPak AS-H, 250×4.6 mm I. D. column eluting with 70% SFC $CO_2$ and 30% 2-Propanol containing 0.05% diethylamine at 2.4 mL/min detecting at 220 nm. Fast eluting enantiomer $R_t$=3.52 min and slow eluting enantiomer $R_t$=4.22 min.

INTERMEDIATE 24

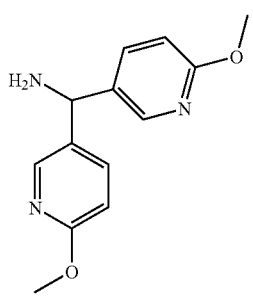

1,1-bis(6-methoxypyridin-3-yl)methanamine

To 5-bromo-2-methoxypyridine (1.00 g, 5.32 mmol) in THF (20 mL) at −78° C. was added n-butyllithium (3.13 mL, 7.83 mmol, 2.5 M in hexane). The reaction was aged at −78° C. for about 25 min at which point the cold bath was removed. 6-methoxypyridine-3-carbonitrile (1.00 g, 7.46 mmol) in THF (10 mL) was added and the reaction aged for about 40 min warming to rt at which point the reaction was concentrated. The residue was diluted with MeOH (20 mL) and $NaBH_4$ (0.282 g 7.46 mmol) was added. The reaction aged about 90 min at rt. The reaction was concentrated and diluted with EtOAc and aq HCl (15 mL, 2 M). The aq portion was extracted twice with EtOAc before adding aq NaOH (20 mL, 2M). The aq portion was then extracted three times with EtOAc. The combined organic portion was concentrated and the residue was purified by flash chromatography on silica gel gradient eluted with 0-100% EtOAc/hexane followed by 0-20% MeOH (containing 1.5% triethylamine)/EtOAc affording the title compound. HPLC/MS: 246 (M+1); $R_t$=1.61 min.

EXAMPLE 192

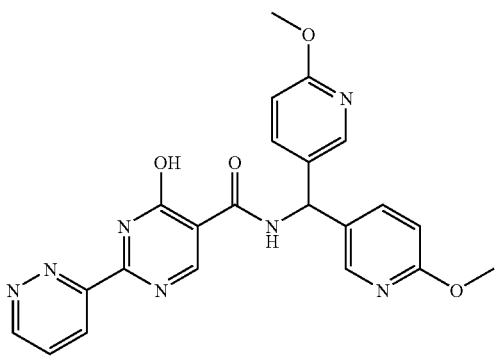

N-[bis(6-methoxypyridin-3-yl)methyl]-4-hydroxy-2-(pyridazin-3-yl)pyrimidine-5-carboxamide The product of Intermediate 8 (0.298 g, 1.367 mmol) was combined with CDI (0.286 g, 1.654 mmol) and DMF (4 mL). The reaction was aged at about 115° C. for 45 min and cooled to about 72° C. The product of Intermediate 24 (0.335 g, 1.37 mmol) and $NEt_3$ (0.286 mL, 2.05 mmol) were added and the reaction was age at 72° C. for about an additional 18 h. The reaction was diluted with $CHCl_3$ and washed with water and enough aq. HCl to adjust the pH to about 4-5. The aq portion was washed 3× with water. The organic portion was concentrated, treated with EtOAc and refluxed for a few minutes. The mixture was further diluted with 1/1 EtOAc/Hexane and the solid was isolated by filtration. The solid was then washed with 1/1 EtOAc/Hexane followed by EtOH. Additional purification was achieved by suspending the solid in EtOH and refluxing for a few minutes. The cooled mixture was then filtered to afford the title compound. HPLC/MS: 446.0 (M+1); $R_t$=2.30 min.

Biological Assays

The exemplified compounds, Examples 1 through 192 of the present invention, have been found to inhibit the interaction between PHD2 and a HIF peptide and exhibit $IC_{50}$ values ranging between 0.1 nanomolar to 10 micromolar. Non-limiting examples of assays that may be useful to detect favorable activity are disclosed in the following publications: Oehme, F., et al., *Anal. Biochem.* 330:74-80 (2004); Hirsilä, M, et al., *J. Bio. Chem.* 278 (33): 30772-30780 (2005); Hyunju, C., et al., *Biochem. Biophys. Res. Comm.* 330 (2005) 275-280; and Hewitson, K. S., et al., *Methods in Enzymology*, (Oxygen Biology and Hypoxia); Elsevier Publisher (2007), pg. 2542 (ISSN: 0076-6879).

The biological activity of the present compounds may be evaluated using assays described herein below:

To each well of a 96-well plate was added 1 μL of test compound in DMSO and 20 μl of assay buffer (50 mM Tris pH 7.4/0.01% Tween-20/0.1 mg/ml bovine serum albumin/10 μM ferrous sulfate/1 mM sodium ascorbate/20 μg/ml catalase) containing 0.15 μg/ml FLAG-tagged full length PHD2 expressed in and purified from baculovirus-infected Sf9 cells. After a 30 min preincubation at room temperature, the enzymatic reactions were initiated by the addition of 4 μL of substrates (final concentrations of 0.2 μM 2-oxoglutarate and 0.5 μM HIF-1α peptide biotinyl-DLDLEMLAPYIPMD-DDFQL). After 2 hr at room temperature, the reactions were terminated and signals were developed by the addition of a 25 μL quench/detection mix to a final concentration of 1 mM ortho-phenanthroline, 0.1 mM EDTA, 0.5 nM anti-(His)$_6$ LANCE reagent (Perkin-Elmer Life Sciences), 100 nM AF647-labeled streptavidin (Invitrogen), and 2 μg/ml (His)$_6$-VHL complex (S. Tan (2001) Protein Expr. Purif. 21, 224-234). The ratio of time resolved fluorescence signals at 665 and 620 nm was determined, and percent inhibition was calculated relative to an uninhibited control sample run in parallel.

Inhibition of the catalytic activity of HIF-PHD1 and HIF-PHD3 can be determined similarly.

Table 9 lists the PHD2 binding activity expressed as IC$_{50}$ (nM), for the compounds of the present invention disclosed in Example 1 through Example 192.

TABLE 9

PHD2 binding activity for the examples listed expressed as IC$_{50}$ (nM):
+ = ≦10
++ = >10 to ≦100
+++ = >100 nM to ≦1,000
++++ = >1,000 to ≦10,000

| Example | PHD2 Activity |
| --- | --- |
| 1 | ++ |
| 2 | + |
| 3 | ++ |
| 4 | ++ |
| 5 | + |
| 6 | + |
| 7 | +++ |
| 8 | + |
| 9 | + |
| 10 | ++ |
| 11 | ++++ |
| 12 | ++ |
| 13 | ++ |
| 14 | + |
| 15 | +++ |
| 16 | ++++ |
| 17 | +++ |
| 18 | +++ |
| 19 | ++ |
| 20 | ++ |
| 21 | ++++ |
| 22 | +++ |
| 23 | +++ |
| 24 | ++ |
| 25 | + |
| 26 | + |
| 27 | + |
| 28 | + |
| 29 | ++ |
| 30 | ++ |
| 31 | +++ |
| 32 | +++ |
| 33 | ++ |
| 34 | ++++ |
| 35 | ++ |
| 36 | ++ |

TABLE 9-continued

PHD2 binding activity for the examples listed expressed as IC$_{50}$ (nM):
+ = ≦10
++ = >10 to ≦100
+++ = >100 nM to ≦1,000
++++ = >1,000 to ≦10,000

| Example | PHD2 Activity |
| --- | --- |
| 37 | ++ |
| 38 | +++ |
| 39 | ++ |
| 40 | +++ |
| 41 | +++ |
| 42 | ++ |
| 43 | ++ |
| 44 | +++ |
| 45 | +++ |
| 46 | +++ |
| 47 | +++ |
| 48 | + |
| 49 | + |
| 50 | + |
| 51 | + |
| 52 | + |
| 53 | + |
| 54 | + |
| 55 | + |
| 56 | ++ |
| 57 | ++ |
| 58 | + |
| 59 | ++ |
| 60 | + |
| 61 | + |
| 62 | + |
| 63 | + |
| 64 | ++ |
| 65 | +++ |
| 66 | +++ |
| 67 | + |
| 68 | ++ |
| 69 | +++ |
| 70 | + |
| 71 | + |
| 72 | + |
| 73 | + |
| 74 | + |
| 75 | + |
| 76 | ++ |
| 77 | ++ |
| 78 | ++ |
| 79 | + |
| 80 | ++ |
| 81 | ++++ |
| 82 | ++ |
| 83 | +++ |
| 84 | ++ |
| 85 | ++ |
| 86 | + |
| 87 | + |
| 88 | + |
| 89 | + |
| 90 | ++ |
| 91 | + |
| 92 | + |
| 93 | + |
| 94 | + |
| 95 | + |
| 96 | + |
| 97 | + |
| 98 | + |
| 99 | + |
| 100 | + |
| 101 | + |
| 102 | + |
| 103 | ++ |
| 104 | ++++ |
| 105 | + |
| 106 | + |
| 107 | + |
| 108 | + |

TABLE 9-continued

PHD2 binding activity for the examples listed expressed as IC$_{50}$ (nM):
+ = ≦10
++ = >10 to ≦100
+++ = >100 nM to ≦1,000
++++ = >1,000 to ≦10,000

| Example | PHD2 Activity |
|---|---|
| 109 | ++ |
| 110 | ++ |
| 111 | + |
| 112 | + |
| 113 | + |
| 114 | + |
| 115 | + |
| 116 | + |
| 117 | + |
| 118 | ++ |
| 119 | ++ |
| 120 | + |
| 121 | + |
| 122 | ++ |
| 123 | + |
| 124 | + |
| 125 | + |
| 126 | + |
| 127 | + |
| 128 | + |
| 129 | + |
| 130 | ++ |
| 131 | + |
| 132 | + |
| 133 | + |
| 134 | + |
| 135 | ++ |
| 136 | + |
| 137 | + |
| 138 | + |
| 139 | + |
| 140 | + |
| 141 | + |
| 142 | + |
| 143 | + |
| 144 | + |
| 145 | + |
| 146 | + |
| 147 | + |
| 148 | + |
| 149 | + |
| 150 | + |
| 151 | + |
| 152 | + |
| 153 |   |
| 154 | + |
| 155 | + |
| 156 | + |
| 157 | + |
| 158 | + |
| 159 | ++ |
| 160 | ++ |
| 161 | + |
| 162 | +++ |
| 163 | + |
| 164 | + |
| 165 | + |
| 166 | + |
| 167 | + |
| 168 | + |
| 169 | + |
| 170 | + |
| 171 | + |
| 172 | + |
| 173 | + |
| 174 | + |
| 175 | + |
| 176 | + |
| 177 | + |
| 178 | + |
| 179 | + |
| 180 | ++ |
| 181 | + |
| 182 | + |
| 183 | + |
| 184 | + |
| 185 | + |
| 186 | + |
| 187 | + |
| 188 | +++ |
| 189 | + |
| 190 | + |
| 191 | + |
| 192 | + |

What is claimed is:

1. A compound of formula I and pharmaceutically acceptable salts thereof

I

A is a heterocyclyl, optionally substituted by one or more $R^9$ substituents;
$R^1$ is selected from —$C_{1-10}$ alkyl, —$C_{0-10}$ alkyl-$C_{3-10}$ cycloalkyl, —$C_{2-10}$ alkenyl, —$C_{0-10}$ alkyl-$C_{5-10}$ cycloalkenyl, —$C_{2-10}$ alkynyl, —$C_{0-10}$ alkylaryl, —$C_{0-10}$ alkylheterocyclyl; —$NR^bR^c$, and —$C_{0-10}$ alkyl $C_{3-10}$ heterocycloalkyl, wherein in $R^1$ said alkyl, alkenyl, alkynyl, cycloalkenyl, aryl, heterocycloalkyl, heterocyclyl, and cycloalkyl are each optionally substituted with one or more $R^8$ substituents, optionally two $R^8$ may join together to form a 3 to 8 member ring;
R2 is selected from hydrogen, —$C_{1-10}$ alkyl, —$OC_{1-10}$ alkylaryl, aryl, —$C_3$-$C_{10}$ cycloalkyl, and heterocyclyl, wherein $C_{1-10}$ alkyl, —$C_3$-$C_{10}$ cycloalkyl, aryl, and heterocyclyl are unsubstituted or substituted with one or more substituents selected from halo, hydroxyl, $C_{1-10}$ alkyl, and —$OC_{1-10}$ alkyl;
$R^3$ is selected from hydroxy;
$R^4$ is selected from hydrogen;
or $R^1$ and $R^2$, are linked together to form a ring of 5 to 8 atoms optionally substituted with one or more substituents $R^9$;
$R^8$ is selected from halogen, hydroxyl, —$C_{1-10}$ alkyl, —$C_{1-10}$ alkenyl, —$C_{1-10}$ alkynyl, —$OC_{1-10}$ alkylaryl, aryl, heterocyclyl, —$C_{3-10}$ cycloalkyl, —$C_{3-10}$ heterocycloalkyl, cyano, oxo, —$OC_{1-10}$ alkyl, $C_{2-6}$ alkylaminocarbonylamino, $C_{0-10}$ alkyloxycarbonylamino$C_{0-6}$alkyl, $C_{0-10}$ alkylcarbonylamino$C_{0-6}$ alkyl, $C_{2-6}$ alkylaminosulfonylamino$C_{0-4}$ alkyl, —$C_{2-6}$ alkylsulfonylamino$C_{0-4}$ alkyl, —$C_{1-4}$ alkylsulfonyl, arylsulfonyl, —$C_{1-10}$ alkylaminosulfonyl, $C_{1-10}$ alkylaminocarbonyl, —(C═O)N($C_{0-6}$ alkyl)$_2$, difluoromethoxy, trifluoromethoxy, trifluoroethoxy, —$SR^a$, and $NR^bR^c$ wherein said alkyl, alkenyl, alkynyl, aryl, heterocyclyl, cycloalkyl, heterocycloalkyl may optionally be substituted with one or more groups selected from hydroxyl, —$CO_2H$, halogen, —$OC_{1-10}$ alkyl, and $C_{1-6}$ alkyl;

$R^9$ is selected from halogen, hydroxy, oxo, aryl, heterocyclyl, —$C_{1-6}$ alkyl, —$C_{3-10}$ cycloalkyl, —$C_{3-10}$ heterocycloalkyl, —($C_{1-10}$ alkyl)aryl, —($C_{0-10}$ alkyl)heterocyclyl, —$C_{5-10}$ cycloalkenyl, —$C_{2-10}$ alkynyl, —$C_{1-6}$ alkoxy, aryloxy, heterocyclyloxy, —$CO_2R^a$, —$NR^bR^c$, —$CONR^bR^c$, —$OCO_2R^a$, —$OCONR^bR^c$, —$NR^dCO_2R^a$, —$NR^dCONR^bR^c$, —$SR^a$ and —$S(O)_nR^a$, wherein said aryl, heterocyclyl, alkoxy, aryloxy, heterocyclyloxy are optionally substituted by one or more substituents $R^{10}$;

$R^{10}$ is selected from aryl, heterocyclyl, halogen, —$C_{1-6}$ alkyl, —$C_{1-6}$ alkoxy, $CO_2R^a$, cyano, O(C=O) $C_{1-6}$ alkyl, $NO_2$, difluoromethoxy, trifluoromethoxy, trifluoroethoxy, —$O_{(0-1)}(C_{1-10})$perfluoroalkyl, $C_{0-10}$ alkylaminocarbonylamino, $C_{0-10}$ alkyloxycarbonylamino$C_{0-10}$ alkyl, $C_{0-10}$ alkylcarbonylamino$C_{0-10}$ alkyl, $C_{0-10}$ alkylaminocarbonyl, $C_{0-10}$ alkylaminosulfonylamino$C_{0-10}$ alkyl, $C_{0-10}$ alkylsulfonylamino$C_{0-10}$ alkyl, $C_{0-10}$ alkylsulfonyl, $C_{0-10}$ alkylaminosulfonyl, —(C=O)N($C_{0-6}$ alkyl)$_2$, —S($C_{0-6}$ alkyl), and $NH_2$; n is 1 or 2;

$R^a$ is chosen from hydrogen; —$C_{1-10}$ alkyl, —($C_{1-6}$ alkyl)$C_{3-8}$ cycloalkyl; and —($C_{1-6}$ alkyl)phenyl; and $R^b$, $R^c$, and $R^d$ are each independently chosen from hydrogen, —$C_{1-10}$ alkyl, —$C_{3-10}$ cycloalkyl, —$C_{3-10}$ heterocycloalkyl, aryl, and heterocyclyl, wherein said alkyl, cycloalkyl, aryl and heterocyclyl are optionally substituted by one or more substituents $R^{10}$.

2. A compound of claim 1 wherein $R^1$ is selected from —$C_{1-10}$ alkyl, —$C_{0-10}$ alkyl-$C_{3-10}$ cycloalkyl, $C_{0-10}$ alkylaryl, —$C_{0-10}$ alkylheterocyclyl; —$NR^bR^c$, and —$C_{0-10}$ alkyl$C_{3-10}$ heterocycloalkyl, wherein $R^1$ is optionally substituted with one or more $R^8$ substituents, and two $R^8$ may join together to form a 3 to 8 member ring.

3. A compound of claim 1 wherein $R^2$ is selected from hydrogen, —$C_{1-10}$ alkyl, aryl, and heterocyclyl, wherein $C_{1-10}$ alkyl, aryl, and heterocyclyl are unsubstituted or substituted with one or more substituents selected from halo, hydroxyl, $C_{1-10}$ alkyl, and —$OC_{1-10}$ alkyl.

4. A compound of claim 1, wherein in the heterocyclyl of A, optionally substituted by one or more $R^9$ substituents is selected from azabenzimidazole, benzo imidazolyl, benzofuryl, benzofurazanyl, benzopyrazolyl, benzothiazolyl, benzothienyl, benzotriazolyl, benzothiophenyl, benzoxazolyl, carbazolyl, carbolinyl, chromanyl, cinnolinyl, furanyl, imidazolyl, indolinyl, indolyl, indolazinyl, indazolyl, isobenzofuryl, isochromanyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridinyl, pyrimidyl, pyrrolyl, quinazolinyl, quinolyl, quinoxalinyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuryl, dihydrobenzothiophenyl, dihydrobenzoxazolyl, dihydrofuryl, dihydroimidazolyl, dihydroindolyl, dihydrosooxazolyl, dihydroisothiazolyl, dihydrooxadiazolyl, dihydrooxazolyl, dihydropyrazinyl, dihydropyrazolyl, dihydropyridinyl, tetrahydroquinolinyl, tetrahydroisoquinolinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuryl, tetrahydrothienyl, tetrahidroquinolinyl, 2,3-dihydrobenzofuryl, 2,3-dihydrobenzo-1,4-dioxinyl, imidazo(2,1-b)(1,3)thiazole, and benzo-1,3-dioxolyl.

5. A compound selected from:

2-(4-Bromopyridin-2-yl)-4-hydroxy-N-(1-methyl-1-phenylethyl)pyrimidine-5-carboxamide;

2-(4-Hydroxy-5-{[(1-methyl-1-phenyl)amino]carbonyl}pyrimidin-2-yl)isonicotinic acid;

6-(5-{[(4-Fluorobenzyl)amino]carbonyl}-4-hydroxypyrimidin-2-yl)nicotinic acid;

4-Hydroxy-N-(1-methyl-1-phenylethyl)-2-pyridazin-3-ylpyrimidine-5-carboxamide;

N-[bis(4-methoxyphenyl)methyl]-4-hydroxy-2-pyridazin-3-ylpyrimidine-5-carboxamide;

N-[bis(4-methoxyphenyl)methyl]-4-hydroxy-2-pyridazin-3-ylpyrimidine-5-carboxamide 1,3-dihydroxy-2-(hydroxymethyl)propan-2-ammonium salt;

N-[bis(4-methoxyphenyl)methyl]-4-hydroxy-2-pyridazin-3-ylpyrimidine-5-carboxamide potassium salt;

N-[bis(4-hydroxyphenyl)methyl]-4-hydroxy-2-pyridazin-3-ylpyrimidine-5-carboxamide;

N-(4-fluorobenzyl)-4-hydroxy-2-pyridin-2-ylpyrimidine-5-carboxamide;

4-Hydroxy-N-(1-methyl-1-phenylethyl)-2-(1H-pyrazol-1-yl)pyrimidine-5-carboxamide;

N-(4-bromobenzyl)-4-hydroxy-2-(1H-pyrazol-1-yl)pyrimidine-5-carboxamide;

4-Hydroxy-2-(1H-pyrazol-1-yl)-N-{[6-(trifluoromethyl)pyridin-3-yl]methyl}pyrimidine-5-carboxamide;

N-(4-fluorobenzyl)-4-hydroxy-2-[5-(trifluoromethyl)pyridin-2-yl]pyrimidine-5-carboxamide;

N-[1-(4-fluorophenyl)ethyl]-4-hydroxy-2-pyridin-2-ylpyrimidine-5-carboxamide;

4-Hydroxy-N-(1-methyl-1-phenylethyl)-2-pyridin-2-ylpyrimidine-5-carboxamide;

N-[bis(4-methoxyphenyl)methyl]-4-hydroxy-2-pyridin-2-ylpyrimidine-5-carboxamide;

N-(biphenyl-4-ylmethyl)-4-hydroxy-2-(6-methylpyridin-2-yl)pyrimidine-5-carboxamide;

N-(2-chloro-4-fluorophenyl)-4-hydroxy-2-(6-methylpyridin-2-yl)pyrimidine-5-carboxamide;

N-(2,4-dichlorobenzyl)-4-hydroxy-2-(6-methylpyridin-2-yl)pyrimidine-5-carboxamide;

N-(4-fluorobenzyl)-4-hydroxy-2-pyrazin-2-ylpyrimidine-5-carboxamide;

4-Hydroxy-N-(1-methyl-1-phenylethyl)-2-pyrazin-2-ylpyrimidine-5-carboxamide;

4-Hydroxy-2-pyrazin-2-yl-N-[4-(trifluoromethyl)benzyl]pyrimidine-5-carboxamide;

N-(4-fluorobenzyl)-4-hydroxy-2,2'-bipyrimidine-5-carboxamide;

4-Hydroxy-N-(1-methyl-1-phenylethyl)-2,2'-bipyrimidine-5-carboxamide;

4-Hydroxy-N-[4-(trifluoromethyl)benzyl]-2,2'-bipyrimidine-5- carboxamide;

N-(2-chlorobenzyl)-4-hydroxy-2-pyridazin-3-ylpyrimidine-5- carboxamide;

N-[(1S)-1-(4-bromophenyl)ethyl]-4-hydroxy-2-pyridazin-3-ylpyrimidine-5-carboxamide;

N-(diphenylmethyl)-4-hydroxy-2-pyridazin-3-ylpyrimidine-5-carboxamide;

4-hydroxy-N-(1-phenylcyclohexyl)-2-pyridazin-3-ylpyrimidine-5-carboxamide;

N-(biphenyl-4-ylmethyl)-4-hydroxy-2-pyridazin-3-ylpyrimidine-5-carboxamide;

4-Hydroxy-2-(2-methyl-1,3-thiazol-4-yl)-N-[4-(trifluoromethyl)benzyl]pyrimidine-5-carboxamide;
N-(biphenyl-4-ylmethyl)-4-hydroxy-2-(2-methyl-1,3-thiazol-4-yl)pyrimidine-5-carboxamide;
4-Hydroxy-2-(2-methyl-1,3-thiazol-4-yl)-N-[4-(trifluoromethoxy)benzyl]pyrimidine-5-carboxamide;
N-[2-(4-fluorophenyl)ethyl]-4-hydroxy-2-(2-methyl-1,3-thiazol-4-yl)pyrimidine-5-carboxamide;
4-Hydroxy-N-(1-methyl-1-phenylethyl)-2-(2-methyl-1,3-thiazol-4-yl)pyrimidine-5-carboxamide;
4-Hydroxy-2-(2-methyl-1,3-thiazol-4-yl)-N-[4-(trifluoromethyl)phenyl]pyrimidine-5-carboxamide;
4-Hydroxy-2-(2-methyl-1,3-thiazol-4-yl)-N-[(1S)-1-phenylpropyl]pyrimidine-5-carboxamide;
4-Hydroxy-2-(2-methyl-1,3-thiazol-4-yl)-N-[(1R)-1-phenylpropyl]pyrimidine-5-carboxamide;
N-(2,4-dichlorobenzyl)-4-hydroxy-2-(2-methyl-1,3-thiazol-4-yl)pyrimidine-5-carboxamide;
N-(2-chloro-4-fluorophenyl)-4-hydroxy-2-(2-methyl-1,3-thiazol-4-yl)pyrimidine-5-carboxamide;
N-(diphenylmethyl)-4-hydroxy-2-(2-methyl-1,3-thiazol-4-yl)pyrimidine-5-carboxamide;
N-(tert-butyl)-4-hydroxy-2-(2-methyl-1,3-thiazol-4-yl)pyrimidine-5-carboxamide;
4-Hydroxy-2-(4-methyl-1,3-thiazol-2-yl)-N-[(1S)-1-phenylpropyl]pyrimidine-5-carboxamide;
N-(biphenyl-3-ylmethyl)-4-hydroxy-2-(2-methyl -1,3-thiazol-4-yl)pyrimidine-5-carboxamide;
4-Hydroxy-N-(1-methyl-1-phenylethyl)-2-(1,3-thiazol-4-yl)pyrimidine-5-carboxamide;
2-(3,5-Dimethyl-1H-pyrazol-1-yl)-4-hydroxy-N-[4-(trifluoromethoxy)benzyl]pyrimidine-5-carboxamide;
N-(diphenylmethyl)-4-hydroxy-2-(1H-pyrrol-2-yl)pyrimidine-5- carboxamide;
N-(diphenylmethyl)-4hydroxy-2-(1H-1,2,4-triazol-1-yl)pyrimidine-5-carboxamide;
4-Hydroxy-N-(1-methyl-1-phenylethyl)-2-(1-methyl-1H-pyrazol-3-yl)pyrimidine-5-carboxamide;
4-Hydroxy-N-[(1S)-1-phenylpropyl]-2-(1H-pyrazol-1-yl) pyrimidine-5-carboxamide;
N-(biphenyl-4-ylmethyl)-4-hydroxy-2(1H-pyrazol-1-yl)pyrimidine-5-carboxamide;
4-Hydroxy-2-(1H-pyrazol-1-yl)-N-[4-(trifluoromethoxy)benzyl]pyrimidine-5-carboxamide;
N-(2,4-dichlorobenzyl)-4-hydroxy-2-(1H-pyrazol-1-yl)pyrimidine-5-carboxamide;
N-(diphenylmethyl)-4-hydroxy-2-(1H-pyrazol-1-yl)pyrimidine-5-carboxamide;
N-(biphenyl-3-ylmethyl)-4-hydroxy-2-(1H-pyrazol-1-yl)pyrimidine-5-carboxamide;
4-Hydroxy-2-(1H-pyrazol-1-yl)-N-[4-(trifluoromethyl)benzyl]pyrimidine-5-carboxamide;
N-(1,3-benzothiazol-2-ylmethyl)-4-hydroxy-2-(1H-pyrazol-1-yl)pyrimidine-5-carboxamide;
4-Hydroxy-N-(1-naphthylmethyl)-2(1H-pyrazol-1-yl)pyrimidine-5-carboxamide;
N-(2,3-dihydro-1H-inden-1-yl)-4-hydroxy-2-(1H-pyrazol-1-yl)pyrimidine-5-carboxamide;
4-Hydroxy-N-[phenyl(pyridin-4-yl)methyl]-2-(1H-pyrazol-1-yl)pyrimidine-5-carboxamide;
N-[(6-chloropyridin-3-yl)methyl]-4-hydroxy-2-(1H-pyrazol-1-yl)pyrimidine-5-carboxamide;
4-Hydroxy-N-[(1S)-1-phenylethyl]-2-(1H-pyrazol-1-yl)pyrimidine-5-carboxamide;
4-hydroxy-N-[(1R)-1-phenylethyl]-2-(1H-pyrazol-1-yl)pyrimidine-5-carboxamide;
N-[(2'-chlorobiphenyl-4-yl)methyl]-4-hydroxy-2-(1H-pyrazol-1-yl)pyrimidine-5-carboxamide;
N-[(4'-fluorobiphenyl-4-yl)methyl]-4-hydroxy-2-(1H-pyrazol-1-yl)pyrimidine-5-carboxamide;
N-[(5-chloropyrazin-2-yl)methyl]-4-hydroxy-2-(1H-pyrazol-1-yl)pyrimidine-5-carboxamide;
N-[3,5-bis(trifluoromethyl)benzyl]-4-hydroxy-2-(1H-pyrazol-1-yl)pyrimidine-5-carboxamide;
4-Hydroxy-N-[(5-methylpyrazin-2-yl)methyl]-2-(1H-pyrazol-1-yl)pyrimidine-5-carboxamide;
N-(1,2-diphenylethyl)-4-hydroxy-2-(1H-pyrazol-1-yl)pyrimidine-5-carboxamide;
N-[2-fluoro-4-(trifluoromethyl)benzyl]-4-hydroxy-2-(1H-pyrazol-1-yl)pyrimidine-5-carboxamide;
N-(cyclopropylmethyl)-4-hydroxy-2-(1H-pyrazol-1-yl)pyrimidine-5-carboxamide;
N-[1-(4-fluorophenyl)ethyl]-4-hydroxy-2-(1H-pyrazol-1-yl)pyrimidine-5-carboxamide;
N-[(1S)-1-(4-fluorophenyl)ethyl]-4-hydroxy-2-(1H-pyrazol-1-yl)pyrimidine-5-carboxamide;
N-[(1R)-1-(4-fluorophenyl)ethyl]-4-hydroxy-2-(1H-pyrazol-1-yl)pyrimidine-5-carboxamide;
N-[1-(4-fluorophenyl)-1-methylethyl]-4-hydroxy-2-(1H-pyrazol-1-yl)pyrimidine-5-carboxamide;
4-Hydroxy-N- {1-methyl-1-[6-(trifluoromethyl)pyridin-3-yl]ethyl}-2-(1H-pyrazol-1-yl) pyrimidine-carboxamide;
N-(4-chlorobenzyl)-4-hydroxy-2-(1H-pyrazol-1-yl)pyrimidine-5-carboxamide;
N'-Ethyl-4-hydroxy-N'-phenyl-2-(1H-pyrazol-1-yl)pyrimidine-5-carbohydrazide trifluoroacetate;
4-Hydroxy-N-(4-methylbenzyl)-2-(1H-pyrazol-1-yl)pyrimidine-5-carboxamide ;
4-Hydroxy-N-[(1R)-1-(4-methylphenyl)ethyl]-2-(1H-pyrazol-1-yl)pyrimidine-5-carboxamide;
4-Hydroxy-N-[(1S)-1-(4-methylphenyl)ethyl]-2-(1H-pyrazol-1-yl)pyrimidine-5-carboxamide;
4-hydroxy-N-piperidin-1-yl-2-(1H-pyrazol-1-yl)pyrimidine-5-carboxamide trifluoroacetate;
5-(Piperidin-1-ylcarbonyl)-2-(1H-pyrazol-1-yl)pyrimidin-4-ol;
N-(4-tert-butylcyclohexyl)-4-hydroxy-2-(1H-pyrazol-1-yl)pyrimidine-5-carboxamide;
4-Hydroxy-N-[(4R)-3-oxoisoxazolidin-4-yl]-2-(1H-pyrazol-1-yl)pyrimidine-5-carboxamide;
N-[(1R)-1-cyclohexylethyl]-4-hydroxy-2-(1H-pyrazol-1-yl)pyrimidine-5-carboxamide;
N-[(1S)-1-cyclohexylethyl]-4-hydroxy-2-(1H-pyrazol-1-yl)pyrimidine-5-carboxamide;
4-hydroxy-2-(1H-pyrazol-1-yl)-N-(1-pyridin-4-ylethyl) pyrimidine-5-carboxamide trifluoroacetate;
4-Hydroxy-N-(1-phenylcyclopropyl)-2-(1H-pyrazol-1-yl)pyrimidine-5-carboxamide;
4-hydroxy-N',N'-diphenyl-2-(1H-pyrazol-1-yl)pyrimidine-5- carbohydrazide trifluoroacetate;
N-[1-(3,4-difluorophenyl)-1-methylethyl]-4-hydroxy-2-(1H-pyrazol-1-yl)pyrimidine-5-carboxamide;
N-{(1R)-1-[(3S,5S,7S)-1-adamantyl]ethyl}-4-hydroxy-2-(1H-pyrazol-1-yl)pyrimidine-5-carboxamide;
N-[(1S)-1-(4-bromophenyl)ethyl]-4-hydroxy-2-(1H-pyrazol-1-yl)pyrimidine-5-carboxamide;
N-{[4-hydroxy-2-(1H-pyrazol-1-yl)pyrimidin-5-yl]carbonyl}glycine;
4-Hydroxy-N-[(6-phenylpyridin-3-yl)methyl]-2-(1H-pyrazol-1-yl)pyrimidine-5-carboxamide;
N-{[6-(2-fluorophenyl)pyridin-3-yl]methyl}-4-hydroxy-2-(1H-pyrazol-1-yl)pyrimidine-5-carboxamide;

N-{[6-(3-fluorophenyl)pyridin-3-yl]methyl}-4-hydroxy-2-(1H-pyrazol-1-yl)pyrimidine-5-carboxamide trifluoroacetate;

N-{[6-(4-fluorophenyl)pyridin-3-yl]methyl}-4-hydroxy-2-(1H-pyrazol-1-yl)pyrimidine-5-carboxamide;

N-{[5-(4-fluorophenyl)pyrazin-2-yl]methyl}-4-hydroxy-2-(1H-pyrazol-1-yl)pyrimidine-5-carboxamide;

N-[(6-cyanopyridin-3-yl)methyl]-4-hydroxy-2-(1H-pyrazol-1-yl)pyrimidine-5-carboxamide;

1-(4-Hydroxy-5-{[(1-methyl-1-phenylethyl)amino]carbonyl}pyrimidin-2-yl)-1H-pyrazole-4-carboxylic acid;

N-[1-(4-bromophenyl)-1-methylethyl]-4-hydroxy-2-(1H-pyrazol-1-yl)pyrimidine-5-carboxamide;

4-hydroxy-N-(4-phenoxybenzyl)-2-(1H-pyrazol-1-yl)pyrimidine-5-carboxamide;

4-hydroxy-N-(1-phenylcyclohexyl)-2-(1H-pyrazol-1-yl)pyrimidine-5-carboxamide;

N-(4-benzoylbenzyl)-4-hydroxy-2-(1H-pyrazol-1-yl)pyrimidine-5-carboxamide;

N-[bis(4-methoxyphenyl)methyl]-4-hydroxy-2-(1H-pyrazol-1-yl)pyrimidine-5-carboxamide;

4-hydroxy-N-[4-(4-methylphenoxy)benzyl]-2-(1H-pyrazol-1-yl)pyrimidine-5-carboxamide;

N-(1-ethyl-1-phenylpropyl)-4-hydroxy-2-(1H-pyrazol-1-yl)pyrimidine-5-carboxamide;

N-[4-(4-fluorophenoxy)benzyl]-4-hydroxy-2-(1H-pyrazol-1-yl)pyrimidine-5-carboxamide;

4-hydroxy-N-[4-(2-methylphenoxy)benzyl]-2-(1H-pyrazol-1-yl)pyrimidine-5-carboxamide;

N-(2,3-dihydro-1-benzofuran-5-ylmethyl)-4-hydroxy-2-(1H-pyrazol-1-yl)pyrimidine-5-carboxamide;

N-9H-fluoren-9-yl-4-hydroxy-2-(1H-pyrazol-1-yl)pyrimidine-5-carboxamide;

methyl 4-[({[4-hydroxy-2-(1H-pyrazol-1-yl)pyrimidin-5-yl]carbonyl}amino)methyl]benzoate;

N-[(6-cyanopyridin-3-yl)(4-methoxyphenyl)methyl]-4-hydroxy-2-pyridazin-3-ylpyrimidine-5-carboxamide;

N-[(1S)-1-(4-cyanophenyl)ethyl]-4-hydroxy-2-(1H-pyrazol-1-yl)pyrimidine-5-carboxamide;

4-Hydroxy-N-[(4-methoxyphenyl)(6-methylpyridin-3-yl)methyl]-2-pyridazin-3-ylpyrimidine-5-carboxamide;

N-[(2,4-Dimethoxyphenyl)(6-methylpyridin-2-yl)methyl]-4-hydroxy-2-pyridazin-3-ylpyrimidine-5-carboxamide;

4-hydroxy-N-[(1S)-1-(4-methoxyphenyl)ethyl]1-2-(1H-pyrazol-1-yl)pyrimidine-5-carboxamide;

4-hydroxy-N-[1-(4-methyl-1,3-thiazol-2-yl)ethyl]-2-(1H-pyrazol-1-yl)pyrimidine-5-carboxamide hydrochloride;

4-hydroxy-2-(1H-pyrazol-1-yl)-N-[1-(pyridin-2-yl)ethyl]pyrimidine-5-carboxamide;

N-[(1S)-2,3-dihydro-1H-inden-1-yl]-4-hydroxy-2-(1H-pyrazol-1-yl)pyrimidine-5-carboxamide;

4-hydroxy-N-[(1R,2S)-2-hydroxy-1,2-diphenylethyl]-2-(1H-pyrazol-1-yl)pyrimidine-5-carboxamide;

4-hydroxy-N-[(1S)-1-(naphthalen-2-yl)ethyl]-2-(1H-pyrazol-1-yl)pyrimidine-5-carboxamide;

4-hydroxy-N-[(1S)-2-hydroxy-1-phenylethyl]-2-(1H-pyrazol-1-yl)pyrimidine-5-carboxamide;

4-hydroxy-N-[(1R)-2-hydroxy-1-phenylethyl]-2-(1H-pyrazol-1-yl)pyrimidine-5-carboxamide;

(2R)-({[4-hydroxy-2-(1H-pyrazol-1-yl)pyrimidin-5-yl]carbonyl}amino)(phenyl)ethanoic acid;

4-hydroxy-N-[phenyl(pyridin-2-yl)methyl]-2-(1H-pyrazol-1-yl)pyrimidine-5-carboxamide trifluoroacetate;

4-hydroxy-N-[(1S)-1-(3-methoxyphenyl)ethyl]-2-(1H-pyrazol-1-yl)pyrimidine-5-carboxamide;

4-hydroxy-N-[(1R,2R)-2-hydroxy-1,2-diphenylethyl]-2-(1H-pyrazol-1-yl)pyrimidine-5-carboxamide;

4-hydroxy-N-[(1R)-2-hydroxy-2-methyl-1-phenylpropyl]-2-(1H-pyrazol-1-yl)pyrimidine-5-carboxamide;

4-hydroxy-N-[(1S)-1-(4-phenoxyphenyl)ethyl]-2H-pyrazol-1-yl)pyrimidine-5-carboxamide;

4-hydroxy-2-(1H-pyrazol-1-yl)-N-{[5-(trifluoromethyl)pyridin-2-yl]methyl}pyrimidine-5-carboxamide;

4-hydroxy-N-(2-methyl-1-phenylpropyl)-2-(1H-pyrazol-1-yl)pyrimidine-5-carboxamide;

N-[(1S)-1-(2,3-dihydro-1,4-benzodioxin-6-yl)ethyl]-4-hydroxy-2H-pyrazol-1-yl)pyrimidine-5-carboxamide;

4-hydroxy-2-(4-methyl-1H-pyrazol-1-yl)-N-[(1S)-1-phenylpropyl]pyrimidine-5-carboxamide;

4-hydroxy-N-[(1S)-1-(4-methoxyphenyl)ethyl]-2-(4-methyl-1H-pyrazol-1-yl)pyrimidine-5-carboxamide;

N-cyclohexyl-4-hydroxy-2-(pyridazin-3-yl)pyrimidine-5-carboxamide;

4-hydroxy-N-[phenyl(pyridin-2-yl)methyl]-2-pyridazin-3-ylpyrimidine-5-carboxamide trifluoroacetate;

4-hydroxy-N-[(1S)-1-(4-phenoxyphenyl)ethyl]-2-(pyridazin-3-yl)pyrimidine-5-carboxamide;

4-hydroxy-N-[(1R,2S)-2-hydroxy-1,2-diphenylethyl]-2-(pyridazin-3-yl)pyrimidine-5-carboxamide;

4-hydroxy-N-[(1R,2R)-2-hydroxy-1,2-diphenylethyl]-2-(pyridazin-3-yl)pyrimidine-5-carboxamide ;

N-[(1S)-1-(2,3-dihydro-1,4-benzodioxin-6-yl)ethyl]-4-hydroxy-2-(pyridazin-3-yl)pyrimidine-5-carboxamide ;

4-hydroxy-2-(1H-pyrazol-1-yl)-N-{(1S)-1-[6-(trifluoromethyl)pyridin-3-yl]ethyl}pyrimidine-5-carboxamide;

4-hydroxy-2-(1H-pyrazol-1-yl)-N-{(1R)-1-[6-(trifluoromethyl)pyridin-3-yl]ethyl}pyrimidine-5-carboxamide;

4-hydroxy-2-(1H-pyrazol-1-yl)-N-{1[6-(trifluoromethyl)pyridin-3-yl]ethyl}pyrimidine-5-carboxamide;

4-hydroxy-N-{phenyl[6-(trifluoromethyl)pyridin-3-yl]methyl}-2-(1H-pyrazol-1-yl)pyrimidine-5-carboxamide;

4-hydroxy-N-{(S)-phenyl[6-(trifluoromethyl)pyridin-3-yl]methyl}-2-(1H-pyrazol-1-yl)pyrimidine-5-carboxamide;

4-hydroxy-N-{(R)-phenyl[6-(trifluoromethyl)pyridin-3-yl]methyl}-2-(1H-pyrazol-1-yl)pyrimidine-5-carboxamide;

4-hydroxy-N-[(4-methoxyphenyl)(4-methyl-1,3-thiazol-2-yl)methyl]-2-(pyridazin-3-yl)pyrimidine-5-carboxamide;

4-hydroxy-N-[(S)-(4-methoxyphenyl)(4-methyl-1,3-thiazol-2-yl)methyl]-2-(pyridazin-3-yl)pyrimidine-5-carboxamide;

4-hydroxy-N-[(R)-(4-methoxyphenyl)(4-methyl-1,3-thiazol-2-yl)methyl]-2-(pyridazin-3-yl)pyrimidine-5-carboxamide;

4-hydroxy-N-[(4-methoxyphenyl)(6-methylpyridin-3-yl)methyl]-2-(pyridazin-3-yl)pyrimidine-5-carboxamide;

4-hydroxy-N-[(S)-(4-methoxyphenyl)(6-methylpyridin-3-yl)methyl]-2-(pyridazin-3-yl)pyrimidine-5-carboxamide;

4-hydroxy-N-[(R)-(4-methoxyphenyl)(6-methylpyridin-3-yl)methyl]-2-(pyridazin-3-yl)pyrimidine-5-carboxamide;

N-[(3-cyanophenyl)(4-methoxyphenyl)methyl]-4-hydroxy-2-(pyridazin-3-yl)pyrimidine-5-carboxamide;

N-[(S)-(3-cyanophenyl)(4-methoxyphenyl)methyl]-4-hydroxy-2-(pyridazin-3-yl)pyrimidine-5-carboxamide;
N-[(R)-(3-cyanophenyl)(4-methoxyphenyl)methyl]-4-hydroxy-2-(pyridazin-3-yl)pyrimidine-5-carboxamide;
N-[(2,4-dimethoxyphenyl)(6-methylpyridin-2-yl)methyl]-4-hydroxy-2-(pyridazin-3-yl)pyrimidine-5-carboxamide;
N-[(S)-(2,4-dimethoxyphenyl)(6-methylpyridin-2-yl)methyl]-4-hydroxy-2-(pyridazin-3-yl)pyrimidine-5-carboxamide;
N-[(R)-(2,4-dimethoxyphenyl)(6-methylpyridin-2-yl)methyl]-4-hydroxy-2-(pyridazin-3-yl)pyrimidine-5-carboxamide;
N-[(4-cyanophenyl)(4-methoxyphenyl)methyl]-4-hydroxy-2-(pyridazin-3-yl)pyrimidine-5-carboxamide;
N-[(S)-(4-cyanophenyl)(4-methoxyphenyl)methyl]-4-hydroxy-2-(pyridazin-3-yl)pyrimidine-5-carboxamide;
N-[(R)-(4-cyanophenyl)(4-methoxyphenyl)methyl]-4-hydroxy-2-(pyridazin-3-yl)pyrimidine-5-carboxamide;
4-hydroxy-N-{(4-methoxyphenyl)[4-(trifluoromethoxy)phenyl]methyl}-2-(pyridazin-3-yl)pyrimidine-5-carboxamide;
4-hydroxy-N-{(S)-(4-methoxyphenyl)[4-(trifluoromethoxy)phenyl]methyl}-2-(pyridazin-3-yl)pyrimidine-5-carboxamide;
4-hydroxy-N-{(R)-(4-methoxyphenyl)[4-(trifluoromethoxy)phenyl]methyl}-2-(pyridazin-3-yl)pyrimidine-5-carboxamide;
N-[(4-cyanophenyl)(2,4-dimethoxyphenyl)methyl]-4-hydroxy-2-(pyridazin-3-yl)pyrimidine-5-carboxamide;
N-[(S)-(4-cyanophenyl)(2,4-dimethoxyphenyl)methyl]-4-hydroxy-2-(pyridazin-3-yl)pyrimidine-5-carboxamide;
N-[(R)-(4-cyanophenyl)(2,4-dimethoxyphenyl)methyl]-4-hydroxy-2-(pyridazin-3-yl)pyrimidine-5-carboxamide;
4-hydroxy-N-[(4-hydroxyphenyl)(4-methoxyphenyl)methyl]-2-(pyridazin-3-yl)pyrimidine-5-carboxamide;
4-hydroxy-N-[(S)-(4-hydroxyphenyl)(4-methoxyphenyl)methyl]-2-(pyridazin-3-yl)pyrimidine-5-carboxamide;
4-hydroxy-N-[(R)-(4-hydroxyphenyl)(4-methoxyphenyl)methyl]-2-(pyridazin-3-yl)pyrimidine-5-carboxamide;
N-[1-(4-cyanophenyl)-3-methylbutyl]-4-hydroxy-2-(pyridazin-3-yl)pyrimidine-5-carboxamide;
N-[(S)-1-(4-cyanophenyl)-3-methylbutyl]-4-hydroxy-2-(pyridazin-3-yl)pyrimidine-5-carboxamide;
N-[(R)-1-(4-cyanophenyl)-3-methylbutyl]-4-hydroxy-2-(pyridazin-3-yl)pyrimidine-5-carboxamide;
N-[1-(4-cyanophenyl)-2-(4-methoxyphenyl)ethyl]-4-hydroxy-2-(pyridazin-3-yl)pyrimidine-5-carboxamide;
N-[(S)-1-(4-cyanophenyl)-2-(4-methoxyphenyl)ethyl]-4-hydroxy-2-(pyridazin-3-yl)pyrimidine-5-carboxamide;
N-[(R)-1-(4-cyanophenyl)-2-(4-methoxyphenyl)ethyl]-4-hydroxy-2-(pyridazin-3-yl)pyrimidine-5-carboxamide;
N-[(4-cyanophenyl)(cyclohexyl)methyl]-4-hydroxy-2-(pyridazin-3-yl)pyrimidine-5-carboxamide;
N-[(S)-(4-cyanophenyl)(cyclohexyl)methyl]-4-hydroxy-2-(pyridazin-3-yl)pyrimidine-5-carboxamide;
N-[(R)-(4-cyanophenyl)(cyclohexyl)methyl]-4-hydroxy-2-(pyridazin-3-yl)pyrimidine-5-carboxamide;
N-[2,3-dihydro-1-benzofuran-5-yl(4-methoxyphenyl)methyl]-4-hydroxy-2-(pyridazin-3-yl) pyrimidine-5-carboxamide;
N-[(S)-2,3-dihydro-1-benzofuran-5-yl(4-methoxyphenyl)methyl]-4-hydroxy-2-(pyridazin-3-yl)pyrimidine-5-carboxamide;
N-[(R)-2,3-dihydro-1-benzofuran-5-yl(4-methoxyphenyl)methyl]-4-hydroxy-2-(pyridazin-3-yl)pyrimidine-5-carboxamide;
N-[1-(biphenyl-4-yl)butyl]-4-hydroxy-2-(1H-pyrazol-1-yl)pyrimidine-5-carboxamide;
4-hydroxy-N-[(4-methoxyphenyl)(pyrazin-2-yl)methyl]-2(1H-pyrazol-1-yl)pyrimidine-5-carboxamide;
4-hydroxy-N-[(4-methoxyphenyl)(6-methoxypyridin-3-yl)methyl]-2-(1H-pyrazol-1-yl)pyrimidine-5-carboxamide trifluoroacetate;
4-hydroxy-N-{(4-methoxyphenyl)[4-(methylsulfanyl)phenyl]methyl}-2-(1H-pyrazol-1-yl)pyrimidine-5-carboxamide;
N-[(6-chloropyridin-3-yl)(4-methoxyphenyl)methyl]-4-hydroxy-2-(pyridazin-3-yl)pyrimidine-5-carboxamide;
4-hydroxy-N-[(4-methoxyphenyl)(6-methoxypyridin-3-yl)methyl]-2-(pyridazin-3-yl)pyrimidine-5-carboxamide;
4-hydroxy-N-[(4-methoxyphenyl)(quinolin-2-yl)methyl]-2-(pyridazin-3yl)pyrimidine-5-carboxamide;
4-hydroxy-N-[(4-methoxyphenyl)(6-methoxyquinolin-2-yl)methyl]-2-(pyridazin-3-yl)pyrimidine-5-carboxamide;
N-[1,3-benzothiazol-2-yl(4-methoxyphenyl)methyl]-4-hydroxy-2-(pyridazin-3-yl)pyrimidine-5-carboxamide;
N-[bis(2,4-dimethoxyphenyl)methyl]-4-hydroxy-2-(pyridazin-3-yl)pyrimidine-5-carboxamide;
N-[bis(4-methoxy-2-methylphenyl)methyl]-4-hydroxy-2-(pyridazin-3-yl)pyrimidine-5-carboxamide;
N-[(2,4-dimethoxyphenyl)(4-fluorophenyl)methyl]-4-hydroxy-2-(pyridazin-3-yl)pyrimidine-5-carboxamide;
N-[(2,6-dimethoxypyridin-3-yl)(4-fluorophenyl)methyl]-4-hydroxy-2-(pyridazin-3-yl)pyrimidine-5-carboxamide;
4-hydroxy-N-{(4-methoxyphenyl)[4-(methylsulfanyl)phenyl]methyl}-2-(pyridazin-3-yl)pyrimidine-5-carboxamide;
N-{(4-chlorophenyl)[4-hydroxyethyl)phenyl]methyl}-4-hydroxy-2-(pyridazin-3-yl)pyrimidine-5-carboxamide;
4-Hydroxy-N-((1R)-2-oxo-1-phenyl-2-{[(1R)-1-phenylethyl]amino}ethyl)-2-(1H-pyrazol-1-yl)pyrimidine-5-carboxamide;
4-Hydroxy-N-[[4-(methoxymethyl)phenyl](4-methoxyphenyl)methyl]-2-pyridazin-3-ylpyrimidine-5-carboxamide;
4-Hydroxy-N-[[(S)-4-(methoxymethyl)phenyl](4-methoxyphenyl)methyl]-2-pyridazin-3-ylpyrimidine-5-carboxamide;
4-Hydroxy-N-[[(R)-4-(methoxymethyl)phenyl](4-methoxyphenyl)methyl]-2-pyridazin-3-ylpyrimidine-5-carboxamide;
N-{bis[4-(methoxymethyl)phenyl]methyl}-4-hydroxy-2-pyridazin-3-ylpyrimidine-5-carboxamide;
4-hydroxy-N-[(1S)-1-(4-isoquinolin-5-ylphenyl)ethyl]-2-pyridazin-3-ylpyrimidine-5-carboxamide
N-{(1S)-1-[4-(6-fluoropyridin-3-yl)phenyl]ethyl}-4-hydroxy-2-pyridazin-3-ylpyrimidine-5-carboxamide trifluoroacetate;
4-hydroxy-2-pyridazin-3-yl-N-[(1S)-1-(4-pyridin-3-ylphenyl)ethyl]pyrimidine-5-carboxamide trifluoroacetate;
N-{[4-hydroxy-2-(1H-pyrazol-1-yl)pyrimidin-5-yl]carbonyl}-2-methylalanine ;
N-[1-(2,3-dihydro-1H-indol-1-yl)-2-methyl-1-oxopropan-2-yl]-4-hydroxy-2-(1H-pyrazol-1-yl)pyrimidine-5-carboxamide;

4-hydroxy-N-[(S)-(4-methoxyphenyl)(6-methoxypyridin-3-yl)methyl]-2-(pyridazin-3-yl)pyrimidine-5-carboxamide;

4-hydroxy-N-[(R)-(4-methoxyphenyl)(6-methoxypyridin-3-yl)methyl]-2-(pyridazin-3-yl)pyrimidine-5-carboxamide;

N-[bis(6-methoxypyridin-3-yl)methyl]-4-hydroxy-2-(pyridazin-3-yl)pyrimidine-5-carboxamide;

and pharmaceutically acceptable salts thereof.

6. A compound according to claim 5 selected from:

2-(4-Bromopyridin-2-yl)-4-hydroxy-N-(1-methyl-1-phenylethyl)pyrimidine-5-carboxamide;

2-(4-Hydroxy-5-{[(1-methyl-1-phenylethyl)amino]carbonyl}pyrimidin-2-yl)isonicotinic acid;

6-(5-{[(4-Fluorobenzyl)amino]carbonyl}-4-hydroxypyrimidin-2-yl)nicotinic acid;

4-Hydroxy-N-(1-methyl-1-phenylethyl)-2-pyridazin-3-ylpyrimidine-5-carboxamide;

N-[bis(4-methoxyphenyl)methyl]-4-hydroxy-2-pyridazin-3-ylpyrimidine-5-carboxamide;

N-[bis(4-methoxyphenyl)methyl]-4-hydroxy-2-pyridazin-3-ylpyrimidine-5-carboxamide 1,3-dihydroxy-2-(hydroxymethyl)propan-2-ammonium salt;

N-[bis(4-methoxyphenyl)methyl]-4-hydroxy-2-pyridazin-3-ylpyrimidine-5-carboxamide potassium salt;

N-[bis(4-hydroxyphenyl)methyl]-4-hydroxy-2-pyridazin-3-ylpyrimidine-5-carboxamide;

N-(4-fluorobenzyl)-4-hydroxy-2-pyridin-2-ylpyrimidine-5-carboxamide; and pharmaceutically acceptable salts thereof.

7. A compound according to claim 6 selected from:

N-[bis(4-methoxyphenyl)methyl]-4-hydroxy-2-pyridazin-3-ylpyrimidine-5-carboxamide;

N-[bis(4-methoxyphenyl)methyl]-4-hydroxy-2-pyridazin-3-ylpyrimidine-5-carboxamide 1,3-dihydroxy-2-(hydroxymethyl) propan-2-ammonium salt;

N-[4bis(4-methoxyphenyl)methyl]-4-hydroxy-2-pyridazin-3-ylpyrimidine-5-carboxamide potassium salt;

N-[bis(4-hydroxyphenyl)methyl]-4-hydroxy-2-pyridazin-3-ylpyrimidine-5-carboxamide;

and pharmaceutically acceptable salts thereof.

8. A compound selected from: N-[bis(4-hydroxyphenyl)methyl]-4-hydroxy-2-pyridazin-3-ylpyrimidine-5- carboxamide and pharmaceutically acceptable salts thereof.

9. A compound according to claim 8 selected from:

N-[bis(4-methoxyphenyl)methyl]-4-hydroxy-2-pyridazin-3-ylpyrimidine-5-carboxamide; N-[bis(4-methoxyphenyl)methyl]-4-hydroxy-2-pyridazin-3-ylpyrimidine-5-carboxamide 1,3-dihydroxy-2-(hydroxymethyl)propan-2-ammonium salt; and N-[bis(4-methoxyphenyl)methyl]-4-hydroxy-2-pyridazin-3-ylpyrimidine-5-carboxamide potassium salt.

10. A compound according to claim 6 selected from:

2-(4-Bromopyridin-2-yl)-4-hydroxy-N-(1-methyl-1-phenylethyl)pyrimidine-5-carboxamide;

2-(4-Hydroxy-5-{[(1-methyl-1-phenylethyl)amino]carbonyl}pyrimidin-2-yl)isonicotinic acid;

6-(5-{[(4-Fluorobenzypamino]carbonyl]-4-hydroxypyrimidin-2-yl)nicotinic acid;

4-Hydroxy-N-(1-methyl-1-phenylethyl)-2-pyridazin-3-ylpyrimidine-5-carboxamide;

N-(4-fluorobenzyl)-4-hydroxy-2-pyridin-2-ylpyrimidine-5-carboxamide; and pharmaceutically acceptable salts thereof.

11. A compound according to claim 10 selected from:

2-(4-Hydroxy-5-{[(1-methyl-1-phenylethyl)amino]carbonyl}pyrimidin-2-yl)isonicotinic acid; and 6-(5-{[(4-Fluorobenzyl)amino]carbonyl}-4-hydroxypyrimidin-2-yl)nicotinic acid;

and pharmaceutically acceptable salts thereof.

12. A compound according to claim 11 selected from:

2-(4-Hydroxy-5-{[(1-methyl-1-phenylethyl)amino]carbonyl}pyrimidin-2-yl)isonicotinic acid;

and pharmaceutically acceptable salts thereof.

13. A pharmaceutical composition comprising a compound of claim 1 and pharmaceutically acceptable carrier.

14. A pharmaceutical composition comprising a compound of claim 5 and a pharmaceutically acceptable carrier.

15. A compound according to claim 4, wherein A is chosen from:

pyridazinyl, pyrimidyl, pyrrolyl, thiazolyl, triazolyl, quinolyl, pyrazolyl, pyrazinyl, and pyridinyl and A is optionally substituted with one or more $R^9$ substituents.

16. A compound selected from N-[bis(4-methoxyphenyl)methyl]-4-hydroxy-2-pyridazin-3-ylpyrimidine-5-carboxamide and pharmaceutically acceptable salts thereof.

17. A pharmaceutical composition comprising a compound of claim 16 and a pharmaceutically acceptable carrier.

* * * * *